(12) United States Patent
Kijlstra et al.

(10) Patent No.: US 9,745,597 B2
(45) Date of Patent: Aug. 29, 2017

(54) COMPOSITIONS AND METHODS FOR CONTROLLING FUNGAL AND BACTERIAL DISEASES IN PLANTS

(71) Applicant: Bayer CropScience LP, Research Triangle Park, NC (US)

(72) Inventors: Johan Kijlstra, Monheim (DE); James Sirikit Namnath, Davis, CA (US); Rolf Pontzen, Monheim (DE); Ulrike Wachendorff-Neumann, Monheim (DE); Carrie Waterman, West Sacramento, CA (US)

(73) Assignee: Bayer CropScience LP, Research Triangle Park, NC (US)

( * ) Notice: Subject to any disclaimer, the term of this patent is extended or adjusted under 35 U.S.C. 154(b) by 38 days.

(21) Appl. No.: 14/724,698

(22) Filed: May 28, 2015

(65) Prior Publication Data
US 2015/0344905 A1 Dec. 3, 2015

Related U.S. Application Data

(60) Provisional application No. 62/004,064, filed on May 28, 2014, provisional application No. 62/004,089, filed on May 28, 2014, provisional application No. 62/156,814, filed on May 4, 2015.

(51) Int. Cl.
*A01N 63/00* (2006.01)
*C12N 15/82* (2006.01)
*A01N 41/04* (2006.01)
*A01N 63/02* (2006.01)

(52) U.S. Cl.
CPC ......... *C12N 15/8282* (2013.01); *A01N 41/04* (2013.01); *A01N 63/00* (2013.01); *A01N 63/02* (2013.01)

(58) Field of Classification Search
None
See application file for complete search history.

(56) References Cited

U.S. PATENT DOCUMENTS

| | | | |
|---|---|---|---|
| 2010/0279388 A1 | 11/2010 | Sakamoto et al. | |
| 2016/0278384 A1 | 9/2016 | Jabs et al. | |

FOREIGN PATENT DOCUMENTS

| | | | |
|---|---|---|---|
| CN | 1853489 | A | 11/2006 |
| CN | 101475882 | A | 7/2009 |
| CN | 101508941 | A | 8/2009 |
| CN | 102154152 | A | 8/2011 |
| CN | 103271092 | A | 9/2013 |
| CN | 102550607 | B | 5/2014 |
| EP | 0503346 | A2 | 9/1992 |
| EP | 2311936 | A1 | 4/2011 |
| EP | 2759590 | A1 | 7/2014 |
| JP | 2002-226893 | A | 8/2002 |
| RU | 2287335 | C1 | 11/2006 |
| WO | 2009/061380 | A2 | 5/2009 |
| WO | 2009/158617 | A1 | 12/2009 |
| WO | 2010/128003 | A2 | 11/2010 |
| WO | 2011/084599 | A1 | 7/2011 |
| WO | 2014/178032 | A1 | 11/2014 |

OTHER PUBLICATIONS

"Evaluation Report: Bacillus subtilis strain QST 713, Serenade MAX, Serenade ASO, Rhapsody ASO, Serenade Garden Concentrate, Serenade Garden Ready to Use", Oct. 22, 2007, pp. 1-79, Pest Management Regulatory Agency, Health Canada, Retrieved from the Internet: URL:http://publications.gc.ca/collections/collection_2007/pmra-arla/H113-26-2007-6E.pdf, [retrieved Aug. 11, 2015].

"Notice of Pesticide Registration: Serenade", May 15, 2007, pp. 1-37, U.S. Environmental Protection Agency, Retrieved from the Internet: URL: http://www.epa.gov/pesticides/chem_search/ppls/069592-00007-20070515.pdf, [retrieved on Aug. 11, 2015].

Furuya, S., et al., "Isolation and Characterization of Bacillus subtilis KS1 for the Biocontrol of Grapevine Fungal Diseases", Biocontrol Science and Technology, Jun. 1, 2011, pp. 705-720, vol. 21, No. 6.

Goes, A.P., et al., "Research Note: Effect of Surfactants on Alpha-Amylase Production in a Solid Substrate Fermentation Process", J. Chem. Technol. and Biotechnol., Jul. 1, 1999, pp. 709-712, vol. 74, No. 7.

Grochowalski, A.R., et al., "Effect of Surfactants on Plasticizer Biodegradation by Bacillus subtilis ATCC 6633", Biodegradation, Nov. 2, 2006, pp. 283-293, vol. 18, No. 3.

Highland, H.B., "The Use of SERNADE MAX® to Control Summer Diseases of Apples in the Eastern U.S.", Apr. 4, 2006, p. 1, Fifth National IPM Symposium, "Delivering on a Promise," St. Louis, MO, U.S.A., Retrieved from the Internet: URL: http://www.ipmcenters.org/IPMSymposiumV/posters/068.pdf, [retrieved on Aug. 11, 2015].

Hiraoka, H., et al., "Characterization of Bacillus subtilis RB14, Coproducer of Peptide Antibiotics Iturin A and Surfactin," J. Gen. Appl. Microbiol., Jan. 1, 1992, pp. 635-640, vol. 38, No. 6.

(Continued)

*Primary Examiner* — Alton Pryor
(74) *Attorney, Agent, or Firm* — Adam L. Lunceford; Michelle L. Samonek

(57) ABSTRACT

The present invention provides a fungicidal composition comprising a strain of *Bacillus subtilis* or *Bacillus amyloliquefaciens* and one of several compounds in a synergistically effective amount. Also provided are methods of controlling fungal harmful organisms and/or bacterial harmful organisms in a plant, the method comprising applying an effective amount of a fungicidal composition to the plant, to a part of the plant and/or to a locus on which the plant or plant part grows.

27 Claims, 7 Drawing Sheets

(56) References Cited

OTHER PUBLICATIONS

Woo, I-S, et al., "Differential Damage in Bacterial Cells by Microwave Radiation on the Basis of Cell Wall Structure", Applied and Environmental Microbiology, May 1, 2000, pp. 2243-2247, vol. 66, No. 5.
International Search Report and Written Opinion of the International Searching Authority, PCT International Patent Application No. PCT/US2015/033031, issued Aug. 25, 2015, 20 pages.

COMPOSITIONS AND METHODS FOR CONTROLLING FUNGAL AND BACTERIAL DISEASES IN PLANTS

CROSS-REFERENCE TO RELATED APPLICATIONS

The present application claims priority to U.S. Provisional Application No. 62/004,064, filed May 28, 2014, U.S. Provisional Application No. 62/004,089, filed May 28, 2014, and U.S. Provisional Application No. 62/156,814, filed May 4, 2015, the contents of which are hereby incorporated by reference in their entirety.

TECHNICAL FIELD

The present invention relates to synergistic combinations of a lipopeptide and one of several compounds. The present invention also provides methods of controlling fungal diseases and bacterial diseases with synergistic compositions.

BACKGROUND

Fungicides have myriad uses, including for crop protection; as food, feed, and cosmetics preservatives; and as therapeutic agents for both human and veterinary applications. Crop yield reduction, foodborne diseases and fungal infections of both humans and animals are a problem in both developed and developing countries.

Non-ribosomal peptides, including cyclic amphiphilic lipopeptides such as surfactins, iturins and fengycins, are well-recognized for their antimicrobial properties and have been used in the field of crop protection. Because of their mode of action, they also have potential uses in biopharmaceutical and other biotechnology applications. Lipopeptides may be obtained through fermentation of various soil bacteria, including *Bacillus subtilis* and *Bacillus amyloliquefaciens*. Lipopeptides kill fungi by disrupting cell membranes. The potential for the development of fungal resistance to these compounds is expected to be very low since they act directly upon membrane lipids and not on a single site protein target. Further, lipopeptides are of low risk to workers and consumers; in fact, crops treated with *Bacillus*-based products may be harvested on the day of treatment.

Due to their hydrophobic nature, the lipopeptides produced by *Bacillus subtilis* and *Bacillus amyloliquefaciens* may have limited bioavailability when applied to plants, plant parts, or soil. Compounds that enhance the bioavailability of these lipopeptides could increase their antifungal activity. As shown below in Examples 28 and 29, an enhanced ability to disperse in an aqueous supernatant rather than to remain in a cell pellet may indicate increased lipopeptide bioavailability (see FIG. 5 and FIG. 6).

There is a need for improved formulations of lipopeptide-producing strains of *Bacillus subtilis* and *Bacillus amyloliquefaciens* with increased antifungal activity. Improvements to the efficacy of *Bacillus*-based products, especially those that are not susceptible to development of fungal resistance, are highly desirable. There exists a continuing need in the art for such improvements to *Bacillus*-based fungicidal formulations.

SUMMARY

The present invention relates to enhanced formulations of a lipopeptide-producing strain of *Bacillus subtilis* or *Bacillus amyloliquefaciens* and one or more of several compounds combined in a synergistically effective amount. The present invention also provides compositions with synergistic antibacterial activity. In addition, novel antifungal compositions and methods of using these compositions are provided.

In some embodiments, the present invention provides a fungicidal composition comprising a lipopeptide-producing strain of *Bacillus subtilis* or *Bacillus amyloliquefaciens*; and a compound of formula (I):

$$H_3C-(\phantom{x})_m-(Z^1)-(\phantom{x})_n-R^1 \quad (I)$$

wherein
m is an integer between 1 and 20;
n is an integer between 1 and 10;
$Z^1$ is at least one of $CH_2$, S, O, and NH; and
$R^1$ is a sulfate, sulfonate, phosphate, or carboxylate;
or a geometrical isomer, optical isomer, enantiomer, diastereoisomer, tautomer, or an agriculturally acceptable salt, metal complex or metalloid complex thereof;
in a synergistically effective amount.

In certain aspects, the lipopeptide-producing strain of *Bacillus subtilis* or *Bacillus amyloliquefaciens* is *Bacillus subtilis* QST713, *Bacillus amyloliquefaciens* strain D747, *Bacillus subtilis* MBI600, *Bacillus subtilis* var. *amyloliquefaciens* FZB24, or a mutant thereof having all the identifying characteristics of the respective strain.

In one embodiment, $R^1$ is a sulfate. In another aspect, $Z^1$ is O. In certain aspects, n is an integer between 1 and 5. In other aspects, m is an integer between 8 and 16.

In another embodiment, the compound is a lauryl ether sulfate with the formula:

$$H_3C-(\text{chain})-(O)_o-O-S(=O)_2-O^-$$

wherein o is an integer between 1 and 5;
or an agriculturally acceptable salt, metal complex or metalloid complex thereof.

In some aspects, the compound is 3,6-dioxaoctadecylsulfate with the formula:

$$H_3C-(\text{chain})-O-(\text{chain})-O-(\text{chain})-O-S(=O)_2-O^-;$$

or an agriculturally acceptable salt, metal complex or metalloid complex thereof.

In other aspects, the compound is 3,6-dioxaeicosylsulfate with the formula:

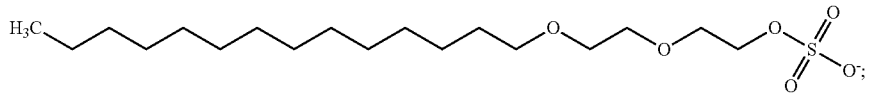

or an agriculturally acceptable salt, metal complex or metalloid complex thereof.

In some embodiments, the weight to weight ratio of the lipopeptide-producing strain of *Bacillus subtilis* or *Bacillus amyloliquefaciens* and the compound of formula (I) is about 1000:1 to about 1:1000, about 500:1 to about 1:500, about 100:1 to about 1:100, about 75:1 to about 1:75, about 50:1 to about 1:50, about 25:1 to about 1:25, about 20:1 to about 1:20, about 10:1 to about 1:10, about 5:1 to about 1:5, or about 3:1 to about 1:3.

In another aspect, the present invention provides a fungicidal composition comprising: a lipopeptide-producing strain of *Bacillus subtilis* or *Bacillus amyloliquefaciens*; and a polyalkylene compound with a sulfate, a sulfonate, a phosphate, or a carboxylate functional group; or an agriculturally acceptable salt, metal complex or metalloid complex thereof in a synergistically effective amount.

The lipopeptide-producing strain of *Bacillus subtilis* or *Bacillus amyloliquefaciens* may be *Bacillus subtilis* QST713, *Bacillus amyloliquefaciens* strain D747, *Bacillus subtilis* MBI600, *Bacillus subtilis* var. *amyloliquefaciens* FZB24, or a mutant thereof having all the identifying characteristics of the respective strain.

In one embodiment, the functional group is a sulfate. In another embodiment, the polyalkylene compound is a $C_2$-$C_{20}$ alkyl sulfate or an agriculturally acceptable salt, metal complex or metalloid complex thereof. In certain aspects, the polyalkylene compound is lauryl sulfate, myristyl sulfate, palmityl sulfate, stearyl sulfate or an agriculturally acceptable salt, metal complex or metalloid complex thereof. In one aspect, the polyalkylene compound is a lauryl ether sulfate with the formula:

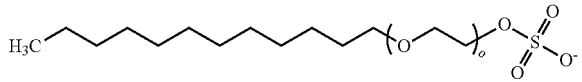

wherein o is an integer between 1 and 5;

or an agriculturally acceptable salt, metal complex or metalloid complex thereof.

In yet another embodiment, the compound is 3,6-dioxaoctadecylsulfate with the formula:

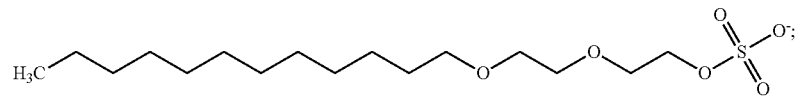

or an agriculturally acceptable salt, metal complex or metalloid complex thereof.

In another aspect, the compound is 3,6-dioxaeicosylsulfate with the formula:

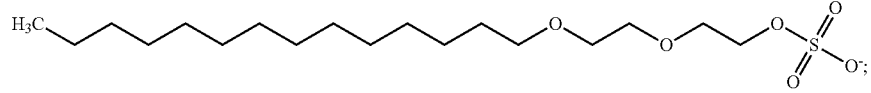

or an agriculturally acceptable salt, metal complex or metalloid complex thereof.

In some embodiments, the weight to weight ratio of the lipopeptide-producing strain of *Bacillus subtilis* or *Bacillus amyloliquefaciens* and the polyalkylene compound is about 1000:1 to about 1:1000, about 500:1 to about 1:500, about 100:1 to about 1:100, about 75:1 to about 1:75, about 50:1 to about 1:50, about 25:1 to about 1:25, about 20:1 to about 1:20, about 10:1 to about 1:10, about 5:1 to about 1:5, or about 3:1 to about 1:3.

In another aspect, the present invention relates to a fungicidal composition comprising: a lipopeptide-producing strain of *Bacillus subtilis* or *Bacillus amyloliquefaciens*; and a sulfonate or an agriculturally acceptable salt, metal complex or metalloid complex thereof in a synergistically effective amount.

In some aspects, the lipopeptide-producing strain of *Bacillus subtilis* or *Bacillus amyloliquefaciens* is *Bacillus subtilis* QST713, *Bacillus amyloliquefaciens* strain D747, *Bacillus subtilis* MBI600, *Bacillus subtilis* var. *amyloliquefaciens* FZB24, or a mutant thereof having all the identifying characteristics of the respective strain.

In other aspects the sulfonate is an aliphatic sulfonate ester or an agriculturally acceptable salt, metal complex or metalloid complex thereof. In one aspect, the aliphatic sulfonate ester has a $C_{1-20}$ alkyl or a $C_{2-20}$ alkene. In another aspect, the sulfonate is an alpha olefin sulfonate or $Li^+$, $Na^+$, $K^+$ or $(C_{1-8}$ alkyl$)_4N^+$ salt thereof.

In certain embodiments, the alpha olefin sulfonate is of formula (IV):

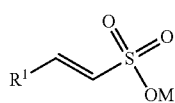
(IV)

wherein

R¹ is a linear or branched $C_{1-20}$ alkyl or a linear or branched $C_{2-20}$ alkene; and M is $H^+$, $Li^+$, $Na^+$, $K^+$ or $(C_{1-8}\ alkyl)_4N^+$.

In some embodiments, R¹ is a linear $C_{8-16}$ alkyl. In other embodiments, the alpha olefin sulfonate is tetradecene sulfonate, hexadecene sulfonate, or a $Li^+$, $Na^+$, $K^+$ or $(C_{1-8}\ alkyl)_4N^+$ salt thereof.

In one aspect, the sulfonate is a compound of formula (V):

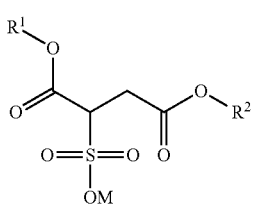
(V)

wherein

R¹ and R² are independently a linear or branched $C_{1-20}$ alkyl or a linear or branched $C_{2-20}$ alkene; and M is $H^+$, $Li^+$, $Na^+$, $K^+$ or $(C_{1-8}\ alkyl)_4N^+$.

In some embodiments, $R_1$ and $R_2$ are independently linear or branched $C_8$ alkyl. In other embodiments, the sulfonate is dioctyl sulfosuccinate; 1,4-bis(2-ethylhexoxy)-1,4-dioxobutane-2-sulfonate; or a $Li^+$, $Na^+$, $K^+$ or $(C_{1-8}\ alkyl)_4N^+$ salt thereof.

In certain aspects, the weight to weight ratio of the lipopeptide-producing strain of *Bacillus subtilis* or *Bacillus amyloliquefaciens* and the sulfonate is about 1000:1 to about 1:1000, about 500:1 to about 1:500, about 100:1 to about 1:100, about 75:1 to about 1:75, about 50:1 to about 1:50, about 25:1 to about 1:25, about 20:1 to about 1:20, about 10:1 to about 1:10, about 5:1 to about 1:5, or about 3:1 to about 1:3.

In another aspect, the present invention provides a fungicidal composition comprising: a lipopeptide-producing strain of *Bacillus subtilis* or *Bacillus amyloliquefaciens*; and a compound of formula (VI):

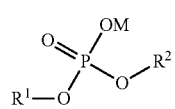
(VI)

wherein each of R¹ and R² is independently $H^+$, $Li^+$, $Na^+$, $K^+$, $(C_{1-8}\ alkyl)_4N^+$, a linear or branched $C_{1-20}$ alkyl, a linear or branched $C_{2-20}$ alkene, or

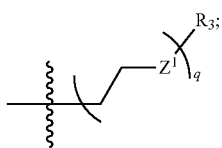

q is an integer between 1 and 10;

$Z^1$ is at least one of $CH_2$, S, O, and NH;

R³ is H, linear or branched $C_{1-20}$ alkyl; and

M is $H^+$, $Li^+$, $Na^+$, $K^+$ or $(C_{1-8}\ alkyl)_4N^+$;

with the proviso that R¹ and R² are not both $H^+$, $Li^+$, $Na^+$, $K^+$, or $(C_{1-8}\ alkyl)_4N^+$ in a synergistically effective amount.

In some embodiments, the lipopeptide-producing strain of *Bacillus subtilis* or *Bacillus amyloliquefaciens* is *Bacillus subtilis* QST713, *Bacillus amyloliquefaciens* strain D747, *Bacillus subtilis* MBI600, *Bacillus subtilis* var. *amyloliquefaciens* FZB24, or a mutant thereof having all the identifying characteristics of the respective strain.

In certain aspects, R¹ and/or R² is

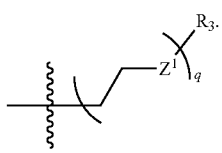

In other aspects, $Z^1$ is O. In yet other aspects, R³ is a branched $C_{1-20}$ alkyl.

In one embodiment the compound is

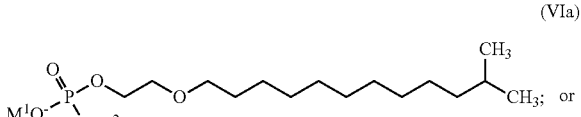
(VIa)

or

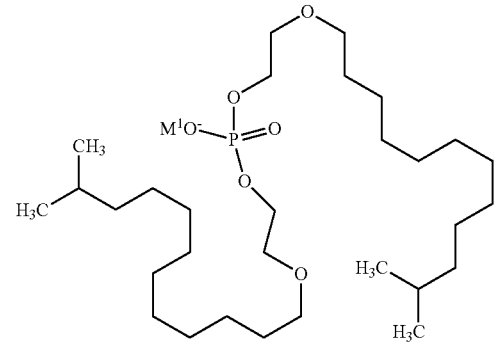
(VIb)

wherein $M^1$ and $M^2$ when they are present are each independently $H^+$, $Li^+$, $Na^+$, $K^+$, or $(C_{1-8}\ alkyl)_4N^+$.

In yet other embodiments, the weight to weight ratio of the lipopeptide-producing strain of *Bacillus subtilis* or *Bacillus amyloliquefaciens* and the compound of formula (VI) is about 1000:1 to about 1:1000, about 500:1 to about 1:500, about 100:1 to about 1:100, about 75:1 to about 1:75, about 50:1 to about 1:50, about 25:1 to about 1:25, about 20:1 to about 1:20, about 10:1 to about 1:10, about 5:1 to about 1:5, or about 3:1 to about 1:3.

In another embodiment, the present invention provides a fungicidal composition comprising: a lipopeptide-producing strain of *Bacillus subtilis* or *Bacillus amyloliquefaciens*; and a zwitterionic compound with a quaternary amine and a carboxylate; or an agriculturally acceptable salt, metal complex or metalloid complex thereof in a synergistically effective amount.

In some aspects, the lipopeptide-producing strain of *Bacillus subtilis* or *Bacillus amyloliquefaciens* is *Bacillus subtilis* QST713, *Bacillus amyloliquefaciens* strain D747, *Bacillus subtilis* MBI600, *Bacillus subtilis* var. *amyloliquefaciens* FZB24, or a mutant thereof having all the identifying characteristics of the respective strain.

In other aspects, the zwitterionic compound is of formula (VII):

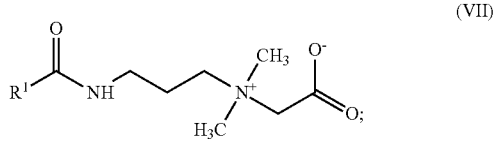

(VII)

wherein $R^1$ is a linear or branched $C_{1-20}$ alkyl or a linear or branched $C_{2-20}$ alkene; or an agriculturally acceptable salt, metal complex or metalloid complex thereof.

In one embodiment, $R^1$ is a linear $C_{1-20}$ alkyl. In another embodiment, the compound is

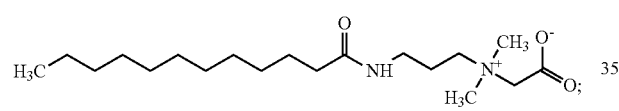

(VIIa)

or an agriculturally acceptable salt, metal complex or metalloid complex thereof.

In certain aspects, the weight to weight ratio of the lipopeptide-producing strain of *Bacillus subtilis* or *Bacillus amyloliquefaciens* and the zwitterionic compound is about 1000:1 to about 1:1000, about 500:1 to about 1:500, about 100:1 to about 1:100, about 75:1 to about 1:75, about 50:1 to about 1:50, about 25:1 to about 1:25, about 20:1 to about 1:20, about 10:1 to about 1:10, about 5:1 to about 1:5, or about 3:1 to about 1:3.

In yet another embodiment, the present invention relates to a fungicidal composition comprising: a lipopeptide-producing strain of *Bacillus subtilis* or *Bacillus amyloliquefaciens*; and a trisiloxane of formula (VIII)

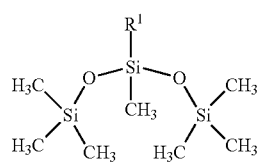

(VIII)

wherein $R^1$ is a linear or branched $C_{1-20}$ alkyl, a linear or branched $C_{2-20}$ alkene,

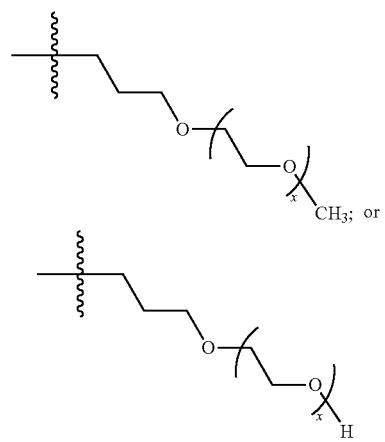

and x is an integer between 1 and 12;

or an agriculturally acceptable salt, metal complex or metalloid complex thereof in a synergistically effective amount.

In one embodiment, the lipopeptide-producing strain of *Bacillus subtilis* or *Bacillus amyloliquefaciens* is *Bacillus subtilis* QST713, *Bacillus amyloliquefaciens* strain D747, *Bacillus subtilis* MBI600, *Bacillus subtilis* var. *amyloliquefaciens* FZB24, or a mutant thereof having all the identifying characteristics of the respective strain.

In some aspects, $R^1$ is

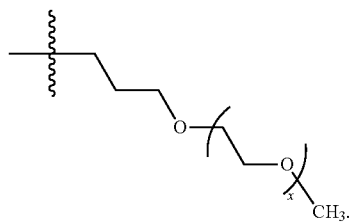

In other aspects, x is 8. In yet other aspects, $R^1$ is

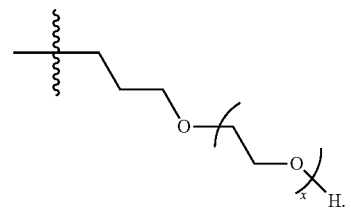

In one embodiment, x is 8.

In certain embodiments, the weight to weight ratio of the lipopeptide-producing strain of *Bacillus subtilis* or *Bacillus amyloliquefaciens* and the trisiloxane of formula (VIII) is about 1000:1 to about 1:1000, about 500:1 to about 1:500, about 100:1 to about 1:100, about 75:1 to about 1:75, about 50:1 to about 1:50, about 25:1 to about 1:25, about 20:1 to about 1:20, about 10:1 to about 1:10, about 5:1 to about 1:5, or about 3:1 to about 1:3.

In certain aspects, the mutant has a genomic sequence with greater than about 90% sequence identity to the respective strain.

In other embodiments, the strain of *Bacillus subtilis* or *Bacillus amyloliquefaciens* is part of fermentation product. In some aspects, the concentration of lipopeptides in the fermentation product is at least 1 mg/g, at least 2 mg/g, at least 3 mg/g, at least 4 mg/g, at least 5 mg/g, at least 6 mg/g, at least 7 mg/g, at least 8 mg/g, at least 9 mg/g, at least 10 mg/g, at least 11 mg/g, at least 12 mg/g, at least 13 mg/g, at least 14 mg/g, or at least 15 mg/g.

In some embodiments, the lipopeptide from the lipopeptide-producing strain of *Bacillus subtilis* or *Bacillus amyloliquefaciens* is an iturin-type compound, a surfactin-type compound, a fengycin-type compound, or a combination thereof. In one aspect, the lipopeptide is a combination of an iturin-type compound, a surfactin-type compound, and a fengycin-type compound. In another aspect, the lipopeptide is a combination of an iturin-type compound and a surfactin-type compound; a combination of an iturin-type compound and a fengycin-type compound; or a combination of a surfactin-type compound and a fengycin-type compound. In some embodiments, the total concentration of the lipopeptide described above is at least 1 mg/g, at least 2 mg/g, at least 3 mg/g, at least 4 mg/g, at least 5 mg/g, at least 6 mg/g, at least 7 mg/g, at least 8 mg/g, at least 9 mg/g, at least 10 mg/g, at least 11 mg/g, at least 12 mg/g, at least 13 mg/g, at least 14 mg/g, or at least 15 mg/g in the fermentation product of the strain of *Bacillus subtilis* or *Bacillus amyloliquefaciens*.

In one aspect, the lipopeptide is an iturin-type compound. The iturin-type compound may be bacillomycin D, bacillomycin F, bacillomycin L, bacillomycin LC (bacillopeptin), mycosubtilin, iturin A, iturin $A_L$, or iturin C. In another aspect, the lipopeptide is a fengycin-type compound. The fengycin-type compound may be fengycin A, fengycin B, plipastatin A, plipastatin B, or an agrastatin. In yet another aspect, the lipopeptide is a surfactin-type compound. The surfactin-type compound may be esperin, lichenysin, pumilacidin, or surfactin.

In some embodiments, the fungicidal composition is a suspension concentrate (SC), an oil dispersion (OD), or water-dispersible granules (WG). In one aspect, the fungicidal composition comprises a fermentation product of a strain of *Bacillus subtilis* or *Bacillus amyloliquefaciens*.

In other embodiments, the present invention provides a method of controlling fungal harmful organisms and/or bacterial harmful organisms in a plant, the method comprising applying an effective amount of the fungicidal composition of any one of the preceding claims to the plant, to a part of the plant and/or to a locus on which the plant or plant part grows or is to be planted.

In certain aspects, the fungal harmful organisms are *Phytophthora infestans* and/or *Botrytis cinerea* and/or *Plasmopara viticola* and/or *Sphaerotheca fuliginea* and/or *Venturia inaequalis* and/or *Alternaria solani* and/or *Uromyces appendiculatus* and/or *Phakopsora pachyrhizi*.

In other aspects, the bacterial harmful organisms are *Acidovorax avenae*, *Burkholderia glumae* and/or *Xanthomonas campestris* pv. *oryzae* in rice, *Candidatus Liberibacter* spec. and/or *Xanthomonas axonopodis* pv. *citri* and/or *Xanthomonas campestris* pv. *vesicatoria* and/or *Xylella fastidiosa* in citrus, *Pseudomonas syringae* pv. *actinidae* in Kiwi, *Xanthomonas campestris* and/or *Xanthomonas campestris* pv. *pruni* in peaches, *Pseudomonas syringae* pv. *glycinea* and/or *Xanthomonas axonopodis* pv. *glycines* in soybeans, *Burkholderia* spec. and/or *Xanthomonas transluscens* in cereals, *Pseudomonas syringae*, *Pseudomonas syringae* pv. *tomato* and/or *Xanthomonas campestris* in tomatoes, *Pseudomonas syringae* and/or *Pseudomonas syringae* pv. *lachrymans* in cucumbers, *Erwinia atroseptica*, *Erwinia carotovora* and/or *Streptomyces scabies* in potatoes.

In yet other aspects, the plant is apples, bananas, citrus, kiwi, melons, peaches, pears, pineapple, pome fruit, pomegranate, cabbage, cauliflower, cucumbers, cucurbits, tomatoes, potatoes, wheat, rice and soybeans.

In some embodiments, the fungicidal composition is applied as a foliar treatment. In other embodiments, the fungicidal composition is applied as a soil treatment.

In certain aspects, the fungicidal composition is applied as a suspension concentrate (SC), an oil dispersion (OD), or water-dispersible granules (WG).

The present invention also provides a method for treating powdery mildew, rust, leaf blotch diseases, leaf wilt diseases, root and stem diseases, ear and panicle diseases, smut fungi diseases, fruit rot, seed and soilborne decay, mould, wilt, rot and damping-off diseases, cancers galls and witches' broom, wilt diseases, leaf blister or leaf curl diseases, the method comprising applying to a plant or plant part a fungicidal composition disclosed herein.

In other aspects, the present invention relates to a method of making a fungicidal composition disclosed herein, comprising mixing the strain of *Bacillus subtilis* or *Bacillus amyloliquefaciens* and the compound; and allowing the mixture to equilibrate for at least 4 hours, 8 hours, 12 hours, or 24 hours.

In some aspects, the method further comprises heating the strain of *Bacillus subtilis* or *Bacillus amyloliquefaciens* and the compound to at least 30 degrees C., at least 40 degrees C., at least 50 degrees C., at least 60 degrees C., at least 70 degrees C., or at least 80 degrees C. after or during mixing.

In one embodiment, the present invention provides a plant or plant part coated with a fungicidal composition disclosed herein. In another embodiment, the present invention relates to a seed treated with a fungicidal composition disclosed herein.

DETAILED DESCRIPTION

Figure 1:
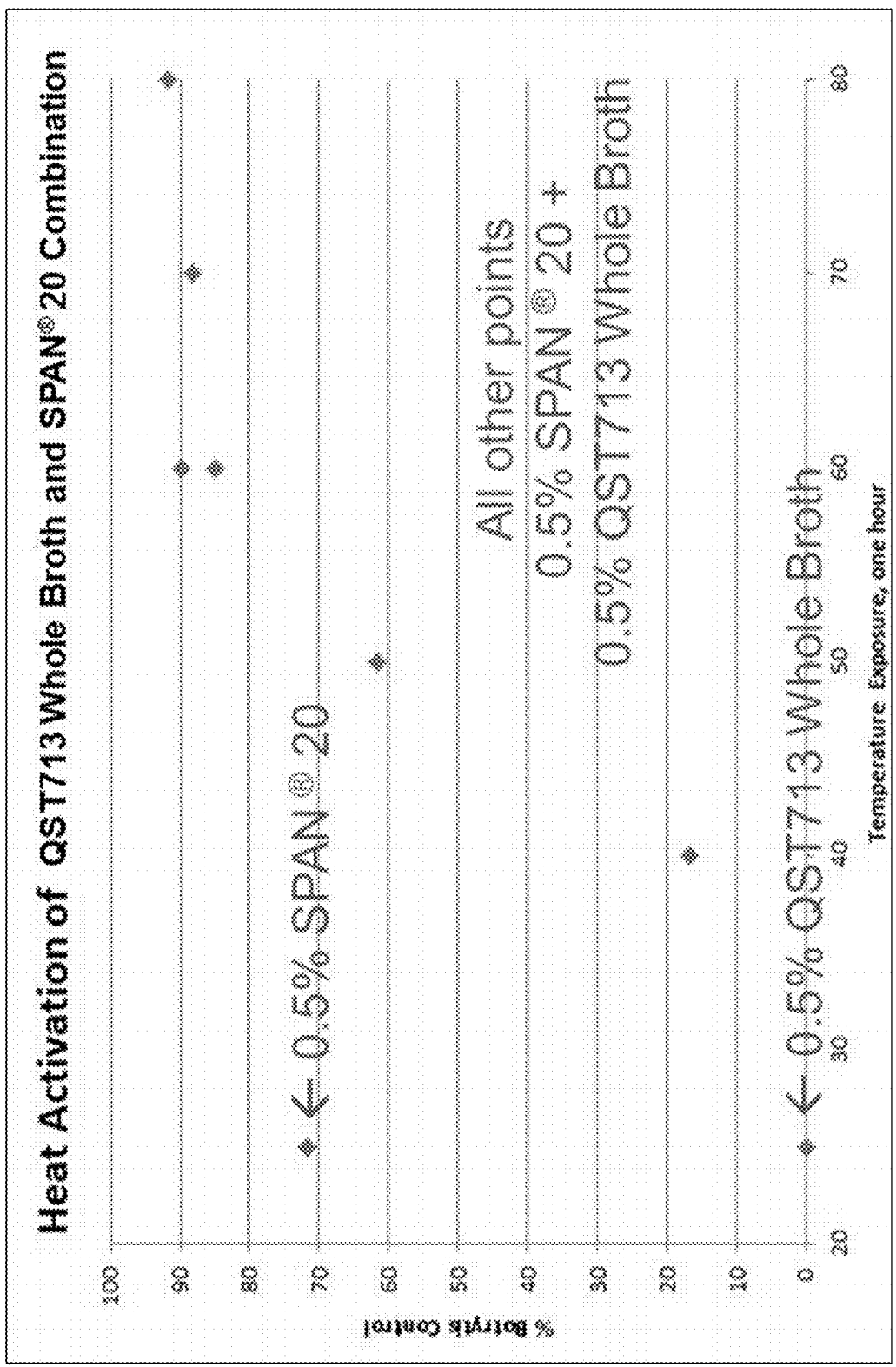
FIG. 1 depicts percent control of *Botrytis cinerea* in infected plants resulting from application of *Bacillus subtilis* QST713 Whole Broth ("QST713 Whole Broth"), SPAN® 20 (sorbitan monolaurate), and combinations of QST713 Whole Broth and SPAN® 20 heated to various temperatures (° C.).

It should be understood that any numerical range recited herein is intended to include all sub-ranges subsumed therein. For example, a range of 1 to 10 is intended to include all sub-ranges between and including the recited minimum value of 1 and the recited maximum value of 10, that is, having a minimum value equal to or greater than 1 and a maximum value of equal to or less than 10. Plural encompasses singular and vice versa; e.g., the singular forms "a," "an," and "the" include plural referents unless expressly and unequivocally limited to one referent.

As used herein, the term "fungal disease" is a disease caused by a fungus or a fungus-like microorganism (e.g., an oomycete).

"Crude extract," as used herein, refers broadly to organic extracts of fermentation broth, including but not limited to ethyl acetate extracts, in which the extract is enriched for lipopeptides. Strains and methods for obtaining an extract of lipopeptides are also described herein.

"Fermentation broth," as used herein, refers broadly to the culture medium resulting after fermentation of a microorganism and encompasses the microorganism and its component parts, unused raw substrates, and metabolites produced by the microorganism during fermentation, among other things.

"Fermentation product," as used herein, refers to fermentation broth and/or fermentation solids.

"Fermentation solid," as used herein, refers to concentrated and/or dried fermentation broth.

"Lipopeptides," as used herein, refers to lipopeptides that are part of a fermentation product and to lipopeptides that are purified to at least some extent, whether chemically synthesized or biologically produced. Lipopeptides include but are not limited to amphiphilic cyclic lipopeptides.

The trade name "GENAPOL® LRO", as used herein, is synonymous with the terms "sodium laureth sulfate" and "sodium lauryl ether sulfate" ("SLES").

The present invention provides a method of treating a plant to control a fungal disease, wherein the method comprises applying to the plant, to a part of the plant and/or to a locus of the plant a composition comprising a compound of formula (I):

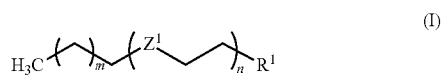

or a salt thereof, wherein
m is an integer between 1 and 18;
n is an integer between 1 and 10;
$Z^1$ is $CH_2$, S, O, or NH;
and $R^1$ is a sulfate, sulfonate, phosphate, or carboxylate.

In one aspect, $R^1$ is a sulfate. In another aspect $Z^1$ is O. In still other aspects, m is an integer between 8 and 16. The compound of formula (I) may be 3,6-dioxaeicosylsulfate with the formula:

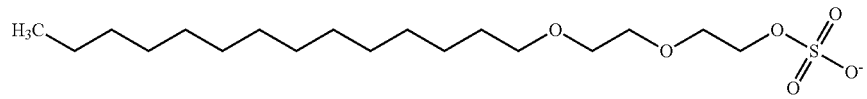 [SMILES: CCCCCCCCCCCCCCOCCOCCOS(=O)(=O)[O-]]

3,6-dioxaoctadecylsulfate with the formula:

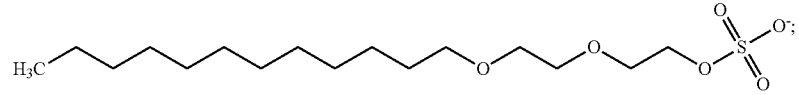

lauryl ether sulfate with the formula:

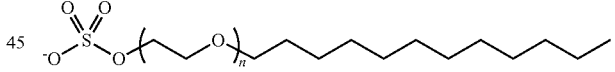

wherein n is an integer between 1 and 5; or a salt thereof.

In another embodiment, the present invention provides a method of treating a plant to control a fungal disease, wherein the method comprises applying to the plant, to a part of the plant and/or to a locus of the plant a composition comprising a compound of formula (II):

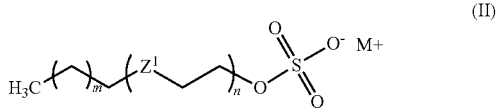

wherein
m is an integer between 0 and 18;
n is an integer between 1 and 10;
$Z^1$ is $CH_2$, S, O, or NH; and when it is present, M+ is selected from the group consisting of H+, Li+, Na+, K+, and $NH_4$+.

In certain aspects, $Z^1$ is O. In other aspects, m is an integer between 8 and 16.

In some embodiments, the compositions of the present invention comprise a compound of formula (III):

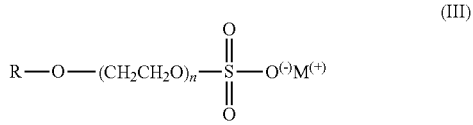

(III)

wherein

R is an alkyl group;

n is an integer of 1 to 10 and means the number of ethyleneoxy units in the (poly)ethyleneoxy bridge; and $M^{(+)}$ is a cation, preferably $H^{(+)}$ or a metal ion or an ammonium ion. A non-limiting list of compounds of formula III is shown below in Table 1, wherein R and n of each compound are specifically indicated in the respective compound name.

TABLE 1

| Non-Limiting Examples of Compounds of Formula (III) |
| --- |
| methyl ethylene glycol ether sulfate, |
| methyl diethylene glycol ether sulfate, |
| methyl triethylene glycol ether sulfate, |
| methyl tetraethylene glycol ether sulfate, |
| methyl pentaethylene glycol ether sulfate, |
| methyl hexaethylene glycol ether sulfate, |
| methyl heptaethylene glycol ether sulfate, |
| methyl octaethylene glycol ether sulfate, |
| methyl nonaethylene glycol ether sulfate, |
| methyl decaethylene glycol ether sulfate, |
| ethyl ethylene glycol ether sulfate, |
| ethyl diethylene glycol ether sulfate, |
| ethyl triethylene glycol ether sulfate, |
| ethyl tetraethylene glycol ether sulfate, |
| ethyl pentaethylene glycol ether sulfate, |
| ethyl hexaethylene glycol ether sulfate, |
| ethyl heptaethylene glycol ether sulfate, |
| ethyl octaethylene glycol ether sulfate, |
| ethyl nonaethylene glycol ether sulfate, |
| ethyl decaethylene glycol ether sulfate, |
| n-propyl ethylene glycol ether sulfate, |
| n-propyl diethylene glycol ether sulfate, |
| n-propyl triethylene glycol ether sulfate, |
| n-propyl tetraethylene glycol ether sulfate, |
| n-propyl pentaethylene glycol ether sulfate, |
| n-propyl hexaethylene glycol ether sulfate, |
| n-propyl heptaethylene glycol ether sulfate, |
| n-propyl octaethylene glycol ether sulfate, |
| n-propyl nonaethylene glycol ether sulfate, |
| n-propyl decaethylene glycol ether sulfate, |
| isopropyl ethylene glycol ether sulfate, |
| isopropyl diethylene glycol ether sulfate, |
| isopropyl triethylene glycol ether sulfate, |
| isopropyl tetraethylene glycol ether sulfate, |
| isopropyl pentaethylene glycol ether sulfate, |
| isopropyl hexaethylene glycol ether sulfate, |
| isopropyl heptaethylene glycol ether sulfate, |
| isopropyl octaethylene glycol ether sulfate, |
| isopropyl nonaethylene glycol ether sulfate, |
| isopropyl decaethylene glycol ether sulfate, |
| n-butyl ethylene glycol ether sulfate, |
| n-butyl diethylene glycol ether sulfate, |
| n-butyl triethylene glycol ether sulfate, |
| n-butyl tetraethylene glycol ether sulfate, |
| n-butyl pentaethylene glycol ether sulfate, |
| n-butyl hexaethylene glycol ether sulfate, |
| n-butyl heptaethylene glycol ether sulfate, |
| n-butyl octaethylene glycol ether sulfate, |
| n-butyl nonaethylene glycol ether sulfate, |
| n-butyl decaethylene glycol ether sulfate, |

TABLE 1-continued

| Non-Limiting Examples of Compounds of Formula (III) |
| --- |
| isobutyl ethylene glycol ether sulfate, |
| isobutyl diethylene glycol ether sulfate, |
| isobutyl triethylene glycol ether sulfate, |
| isobutyl tetraethylene glycol ether sulfate, |
| isobutyl pentaethylene glycol ether sulfate, |
| isobutyl hexaethylene glycol ether sulfate, |
| isobutyl heptaethylene glycol ether sulfate, |
| isobutyl octaethylene glycol ether sulfate, |
| isobutyl nonaethylene glycol ether sulfate, |
| isobutyl decaethylene glycol ether sulfate, |
| sec-butyl ethylene glycol ether sulfate, |
| sec-butyl diethylene glycol ether sulfate, |
| sec-butyl triethylene glycol ether sulfate, |
| sec-butyl tetraethylene glycol ether sulfate, |
| sec-butyl pentaethylene glycol ether sulfate, |
| sec-butyl hexaethylene glycol ether sulfate, |
| sec-butyl heptaethylene glycol ether sulfate, |
| sec-butyl octaethylene glycol ether sulfate, |
| sec-butyl nonaethylene glycol ether sulfate, |
| sec-butyl decaethylene glycol ether sulfate, |
| tert-butyl ethylene glycol ether sulfate, |
| tert-butyl diethylene glycol ether sulfate, |
| tert-butyl triethylene glycol ether sulfate, |
| tert-butyl tetraethylene glycol ether sulfate, |
| tert-butyl pentaethylene glycol ether sulfate, |
| tert-butyl hexaethylene glycol ether sulfate, |
| tert-butyl heptaethylene glycol ether sulfate, |
| tert-butyl octaethylene glycol ether sulfate, |
| tert-butyl nonaethylene glycol ether sulfate, |
| tert-butyl decaethylene glycol ether sulfate, |
| n-pentyl ethylene glycol ether sulfate, |
| n-pentyl diethylene glycol ether sulfate, |
| n-pentyl triethylene glycol ether sulfate, |
| n-pentyl tetraethylene glycol ether sulfate, |
| n-pentyl pentaethylene glycol ether sulfate, |
| n-pentyl hexaethylene glycol ether sulfate, |
| n-pentyl heptaethylene glycol ether sulfate, |
| n-pentyl octaethylene glycol ether sulfate, |
| n-pentyl nonaethylene glycol ether sulfate, |
| n-pentyl decaethylene glycol ether sulfate, |
| isopentyl ethylene glycol ether sulfate, |
| isopentyl diethylene glycol ether sulfate, |
| isopentyl triethylene glycol ether sulfate, |
| isopentyl tetraethylene glycol ether sulfate, |
| isopentyl pentaethylene glycol ether sulfate, |
| isopentyl hexaethylene glycol ether sulfate, |
| isopentyl heptaethylene glycol ether sulfate, |
| isopentyl octaethylene glycol ether sulfate, |
| isopentyl nonaethylene glycol ether sulfate, |
| isopentyl decaethylene glycol ether sulfate, |
| n-hexyl ethylene glycol ether sulfate, |
| n-hexyl diethylene glycol ether sulfate, |
| n-hexyl triethylene glycol ether sulfate, |
| n-hexyl tetraethylene glycol ether sulfate, |
| n-hexyl pentaethylene glycol ether sulfate, |
| n-hexyl hexaethylene glycol ether sulfate, |
| n-hexyl heptaethylene glycol ether sulfate, |
| n-hexyl octaethylene glycol ether sulfate, |
| n-hexyl nonaethylene glycol ether sulfate, |
| n-hexyl decaethylene glycol ether sulfate, |
| n-heptyl ethylene glycol ether sulfate, |
| n-heptyl diethylene glycol ether sulfate, |
| n-heptyl triethylene glycol ether sulfate, |
| n-heptyl tetraethylene glycol ether sulfate, |
| n-heptyl pentaethylene glycol ether sulfate, |
| n-heptyl hexaethylene glycol ether sulfate, |
| n-heptyl heptaethylene glycol ether sulfate, |
| n-heptyl octaethylene glycol ether sulfate, |
| n-heptyl nonaethylene glycol ether sulfate, |
| n-heptyl decaethylene glycol ether sulfate, |
| n-octyl ethylene glycol ether sulfate, |
| n-octyl diethylene glycol ether sulfate, |
| n-octyl triethylene glycol ether sulfate, |
| n-octyl tetraethylene glycol ether sulfate, |
| n-octyl pentaethylene glycol ether sulfate, |

TABLE 1-continued

Non-Limiting Examples of Compounds of Formula (III)

n-octyl hexaethylene glycol ether sulfate,
n-octyl heptaethylene glycol ether sulfate,
n-octyl octaethylene glycol ether sulfate,
n-octyl nonaethylene glycol ether sulfate,
n-octyl decaethylene glycol ether sulfate,
2-ethylhexyl ethylene glycol ether sulfate,
2-ethylhexyl diethylene glycol ether sulfate,
2-ethylhexyl triethylene glycol ether sulfate,
2-ethylhexyl tetraethylene glycol ether sulfate,
2-ethylhexyl pentaethylene glycol ether sulfate,
2-ethylhexyl hexaethylene glycol ether sulfate,
2-ethylhexyl heptaethylene glycol ether sulfate,
2-ethylhexyl octaethylene glycol ether sulfate,
2-ethylhexyl nonaethylene glycol ether sulfate,
2-ethylhexyl decaethylene glycol ether sulfate,
n-nonyl ethylene glycol ether sulfate,
n-nonyl diethylene glycol ether sulfate,
n-nonyl triethylene glycol ether sulfate,
n-nonyl tetraethylene glycol ether sulfate,
n-nonyl pentaethylene glycol ether sulfate,
n-nonyl hexaethylene glycol ether sulfate,
n-nonyl heptaethylene glycol ether sulfate,
n-nonyl octaethylene glycol ether sulfate,
n-nonyl nonaethylene glycol ether sulfate,
n-nonyl decaethylene glycol ether sulfate, wherein in each case any salts and mixtures thereof may be used including alkali metal salts having $M^{(+)}$=an alkali metal cation as counter ion or ammonium salts having $M^{(+)}=NH_4^+$ as counter ion and wherein their sodium salts, potassium salts or ammonium salts are preferred in some aspects.

As used herein, the term "sorbitan" refers to a compound or substituent of a compound having the following structure:

wherein each of the —OH groups may form an ester or ether bond.

The present invention provides a method of treating a plant to control a fungal disease, wherein the method comprises applying to the plant, to a part of the plant and/or to a locus of the plant a composition comprising a compound of formula (I):

(I)

or a stereoisomer thereof, wherein
o is an integer between 0 and 10;
p is an integer between 0 and 2;
q is an integer between 0 and 10;
$X^1$ is an ester bond or a glycosidic bond with an —OH on $R^1$; and
$R^1$ is a pentose, a hexose, or a sorbitan substituent, optionally substituted with a pentose, hexose, sorbitan, $C_1$ to $C_{18}$ alkyl, or $C_1$ to $C_{18}$ alkenyl substituent.

In some embodiments, $R^1$ is optionally substituted with one and only one pentose, hexose, sorbitan, $C_1$ to $C_{18}$ alkyl, or $C_1$ to $C_{18}$ alkenyl substituent. In other embodiments, the sum of o, p, and q is an integer between 8 and 18.

In certain aspects, the compound of formula (I) is a sorbitan ester. The alkyl chain on the sorbitan ester may be saturated or unsaturated. In one aspect, the composition of the present invention comprises:

(Ia)

a stereoisomer thereof, or combinations thereof.

In another aspect, the sorbitan ester has an alkyl chain with at least one double bond. In the compound of formula (I) o may be 7 and p may be 1. In certain aspects, the composition of the present invention comprises:

(Ib)

a stereoisomer thereof, or combinations thereof.

In other embodiments, $X^1$ is a glycosidic bond in the compound of formula (I). In certain aspects, $R^1$ is a hexose substituent or a glucose substituent in the compound of formula (I). In yet other aspects, the composition of the present invention comprises a compound of formula (II):

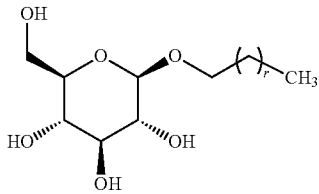

(II)

wherein r is an integer between 6 and 20. In some embodiments, the compound of formula (II) is selected from the group consisting of:

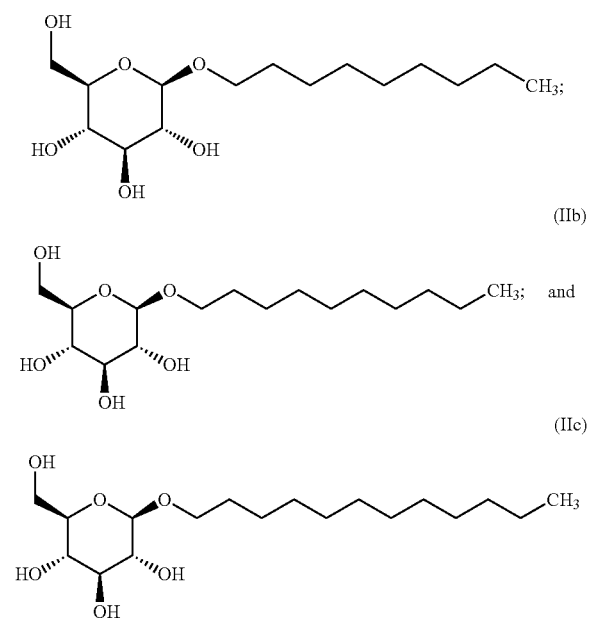

(IIa)

(IIb)

(IIc)

In yet other embodiments, $R^1$ in the compound of formula (I) is substituted with one and only one pentose, hexose, or sorbitan substituent. The compound may contain a disaccharide substituent. In certain aspects, this disaccharide substituent is a sucrose substituent. The composition of the present invention may comprise

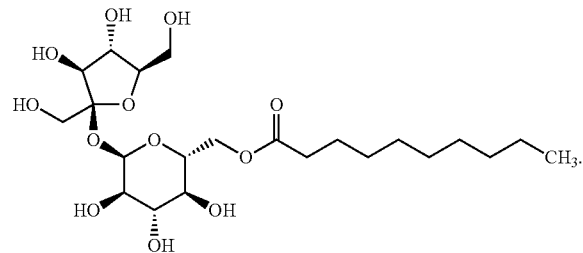

(IId)

In some embodiments, the compounds of the present invention may be combined with or used in combination with a lipopeptide. For example, the method of treating a plant to control a fungal disease may further comprise simultaneously or sequentially applying to the plant, to the part of the plant and/or to the locus of the plant a lipopeptide.

The lipopeptide may be part of or an extract of a fungicidal lipopeptide-producing fermentation product. In certain aspects, lipopeptide-producing fermentation product is a *Bacillus* sp. such as, for example, *Bacillus subtilis* QST713 or its variants; *Bacillus amyloliquefaciens* strain D747; *Bacillus subtilis* MBI600; *Bacillus subtilis* Y1336; *Bacillus amyloliquefaciens* strain FZB42; or *Bacillus subtilis* var. *amyloliquefaciens* FZB24.

Typically, the lipopeptide-producing fermentation product when applied to a seed is applied at a rate of about $1 \times 10^2$ to about $1 \times 10^7$ cfu/seed, depending on the size of the seed. In some embodiments, the application rate is about $1 \times 10^3$ to about $1 \times 10^6$ cfu per seed.

When used as a soil treatment, lipopeptide-producing fermentation product can be applied as a soil surface drench, shanked-in, injected and/or applied in-furrow or by mixture with irrigation water. The rate of application for drench soil treatments, which may be applied at planting, during or after seeding, or after transplanting and at any stage of plant growth, is typically about $4 \times 10^{11}$ to about $8 \times 10^{12}$ cfu per acre. In some embodiments, the rate of application is about $1 \times 10^{12}$ to about $6 \times 10^{12}$ cfu per acre. In some embodiments, the rate of application is about $6 \times 10^{12}$ to about $8 \times 10^{12}$ cfu per acre. The rate of application for in-furrow treatments, applied at planting, is about $2.5 \times 10^{10}$ to about $5 \times 10^{11}$ cfu per 1000 row feet. In some embodiments, the rate of application is about $6 \times 10^{10}$ to about $4 \times 10^{11}$ cfu per 1000 row feet. In other embodiments, the rate of application is about $3.5 \times 10^{11}$ cfu per 1000 row feet to about $5 \times 10^{11}$ cfu per 1000 row feet.

The present invention provides a method of treating a plant to control a fungal disease, wherein the method comprises applying to the plant, to a part of the plant and/or to a locus of the plant a composition comprising a compound of formula (I):

(I)

or a stereoisomer thereof, wherein
o is an integer between 0 and 10;
p is an integer between 0 and 2;
q is an integer between 0 and 10;
$X^1$ is an ester bond or a glycosidic bond with an —OH on $R^1$; and
$R^1$ is a pentose, a hexose, or a sorbitan substituent, optionally substituted with a pentose, hexose, sorbitan, $C_1$ to $C_{18}$ alkyl, or $C_1$ to $C_{18}$ alkenyl substituent.

In certain embodiments, the method of the present invention comprises applying to the plant, to a part of the plant and/or to a locus of the plant a composition comprising a compound of formula (II):

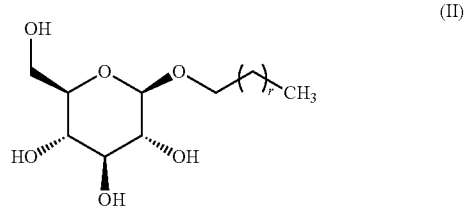

(II)

wherein r is an integer between 6 and 20.

In other embodiments, the composition comprises a sorbitan ester such as, for example, sorbitan monolaurate, In another embodiment, the compound is 3,6-dioxaoctadecylsulfate with the formula:

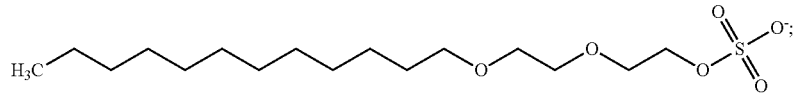

sorbitan monopalmitate, sorbitan sesquioleate, sorbitan monostearate, or combinations thereof. In some embodiments, the composition comprises SPAN® 20 (sorbitan monolaurate) and/or TWEEN® 20 (polyethylene glycol sorbitan monolaurate).

In yet other embodiments, the present invention provides a synergistic fungicidal combination of a lipopeptide and a compound of formula (I) or a stereoisomer thereof, wherein
o is an integer between 0 and 10;
p is an integer between 0 and 2;
q is an integer between 0 and 10;
$X^1$ is an ester bond or a glycosidic bond with an —OH from $R^1$; and
$R^1$ is a pentose, a hexose, or a sorbitan substituent, optionally substituted with a pentose, hexose, sorbitan, $C_1$ to $C_{18}$ alkyl, or $C_1$ to $C_{18}$ alkenyl substituent.

The present invention is directed to a synergistic composition comprising: a) a lipopeptide; and b) a compound of formula (I):

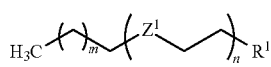

(I)

wherein
m is an integer between 1 and 20;
n is an integer between 1 and 10;
$Z^1$ is $CH_2$, S, O, or NH; and
$R^1$ is a sulfate, sulfonate, phosphate, or carboxylate;
or a geometrical isomer, optical isomer, enantiomer, diastereoisomer, tautomer, or an agriculturally acceptable salt, metal complex or metalloid complex thereof. Agriculturally acceptable salts include but are not limited to lithium salts, sodium salts, potassium salts, and tetraalkylammonium salts.

In some embodiments, $R^1$ is a sulfate. In other embodiments, $Z^1$ is O. In certain aspects, n is an integer between 1 and 5. In yet other aspects, m is an integer between 8 and 16.

In one embodiment, the compound is a lauryl ether sulfate with the formula:

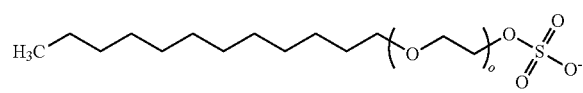

wherein o is an integer between 1 and 5; or an agriculturally acceptable salt, metal complex or metalloid complex thereof.

or an agriculturally acceptable salt, metal complex or metalloid complex thereof.

In some aspects, the compound is 3,6-dioxaeicosylsulfate with the formula:

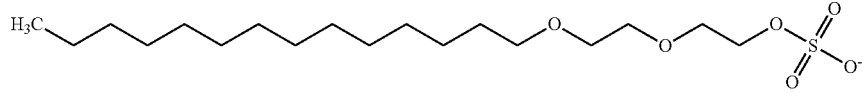 [SMILES: CCCCCCCCCCCCCCOCCOCCOS(=O)(=O)[O-]]

or an agriculturally acceptable salt, metal complex or metalloid complex thereof. In one aspect, the compound is GENAPOL® LRO (sodium $C_{12}/C_{14}$-fatty alcohol diglycol ether sulfate).

In yet other embodiments, the present invention is directed to a synergistic composition comprising: a) a lipopeptide; and b) a polyalkylene compound with a functional group selected from the group consisting of a sulfate, a sulfonate, a phosphate, and a carboxylate; or an agriculturally acceptable salt, metal complex or metalloid complex thereof.

In some aspects, the functional group is a sulfate. In other aspects, the polyalkylene compound is a $C_2$-$C_{20}$ alkyl sulfate or an agriculturally acceptable salt, metal complex or metalloid complex thereof. In yet other aspects, the polyalkylene compound is lauryl sulfate, myristyl sulfate, palmityl sulfate, stearyl sulfate or an agriculturally acceptable salt, metal complex or metalloid complex thereof. In some embodiments, the polyalkylene compound is a lauryl sulfate. In one embodiment, the lauryl sulfate is sodium lauryl sulfate. In some embodiments, the sodium lauryl sulfate is LOXANOL® K12P (sodium lauryl sulfate) or TEAXAPON® K12 (sodium lauryl sulfate).

In one embodiment, the polyalkylene compound is a lauryl ether sulfate with the formula:

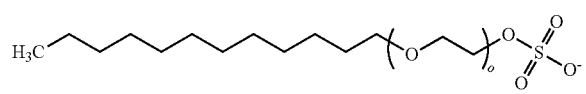

wherein o is an integer between 1 and 5; or an agriculturally acceptable salt, metal complex or metalloid complex thereof.

In another embodiment, the compound is 3,6-dioxaoctadecylsulfate with the formula:

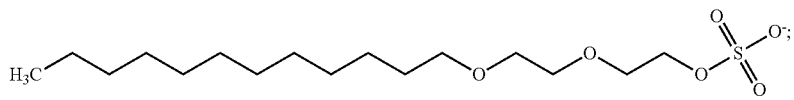

or an agriculturally acceptable salt, metal complex or metalloid complex thereof.

In other aspects, the compound is 3,6-dioxaeicosylsulfate with the formula:

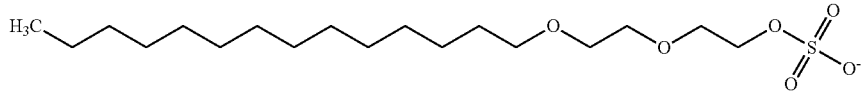 [SMILES: CCCCCCCCCCCCCCOCCOCCOS(=O)(=O)[O-]]

or an agriculturally acceptable salt, metal complex or metalloid complex thereof. In one aspect, the compound is GENAPOL® LRO (sodium $C_{12}/C_{14}$-fatty alcohol diglycol ether sulfate).

In another aspect, the present invention is directed to a synergistic composition comprising: a) a lipopeptide; and b) a sulfonate or an agriculturally acceptable salt, metal complex or metalloid complex thereof. In one embodiment, the sulfonate is an aliphatic sulfonate ester or an agriculturally acceptable salt, metal complex or metalloid complex thereof. In another embodiment, the aliphatic sulfonate ester has a $C_{1-20}$ alkyl or a $C_{2-20}$ alkene.

In certain aspects, the sulfonate is an alpha olefin sulfonate or $Li^+$, $Na^+$, $K^+$ or $(C_{1-8}$ alkyl$)_4N^+$ salt thereof. In one aspect, the alpha olefin sulfonate is of formula (IV):

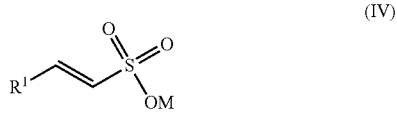

(IV)

wherein $R^1$ is a linear or branched $C_{1-20}$ alkyl or a linear or branched $C_{2-20}$ alkene; and M is $H^+$, $Li^+$, $Na^+$, $K^+$ or $(C_{1-8}$ alkyl$)_4N^+$.

In certain embodiments, $R^1$ is a linear $C_{8-16}$ alkyl. In one aspect, the alpha olefin sulfonate is tetradecene sulfonate, hexadecene sulfonate, or a $Li^+$, $Na^+$, $K^+$ or $(C_{1-8}$ alkyl$)_4N^+$ salt thereof. In one embodiment, the sulfonate is TERWET® 1004 (alpha olefin sulphonate).

In another aspect, the sulfonate is a compound of formula (V):

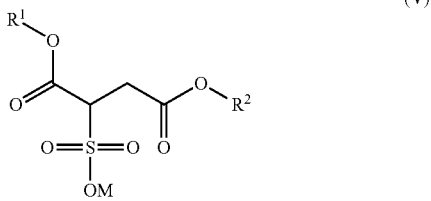

(V)

wherein $R^1$ and $R^2$ are independently a linear or branched $C_{1-20}$ alkyl or a linear or branched $C_{2-20}$ alkene; and M is selected from the group consisting of $H^+$, $Li^+$, $Na^+$, $K^+$ and $(C_{1-8}$ alkyl$)_4N^+$.

In some embodiments, $R_1$ and $R_2$ are independently linear or branched $C_8$ alkyl. In one aspect, the sulfonate is dioctyl sulfosuccinate; 1,4-bis(2-ethylhexoxy)-1,4-dioxobutane-2-sulfonate; or a $Li^+$, $Na^+$, $K^+$ or $(C_{1-8}$ alkyl$)_4N^+$ salt thereof. In certain embodiments, the sulfonate is MONAWET™ MO-75E (sodium dioctyl sulphosuccinate); MULTIWET™ MO-70R (sodium dioctyl sulphosuccinate); or GEROPON® DOS-PG (sodium-2-ethylhexylsulfosuccinate).

In other embodiments, the present invention is directed to a synergistic composition comprising: a) a lipopeptide; and b) a phosphoric ester compound.

In some embodiments, the phosphoric ester is a compound of formula (VI):

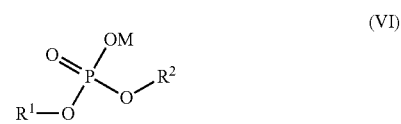

(VI)

wherein each of $R^1$ and $R^2$ is independently $H^+$, $Li^+$, $Na^+$, $K^+$, $(C_{1-8}$ alkyl$)_4N^+$, a linear or branched $C_{1-20}$ alkyl, a linear or branched $C_{2-20}$ alkene, or

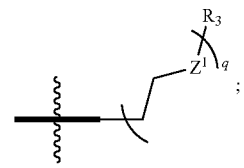

q is an integer between 1 and 10;
$Z^1$ is $CH_2$, S, O, or NH;
$R^3$ is H, linear or branched $C_{1-20}$ alkyl; and
M is $H^+$, $Li^+$, $Na^+$, $K^+$ or $(C_{1-8}$ alkyl$)_4N^+$;
with the proviso that $R^1$ and $R^2$ are not both $H^+$, $Li^+$, $Na^+$, $K^+$, or $(C_{1-8}$ alkyl$)_4N^+$.

In certain aspects, $R^1$ and/or $R^2$ is

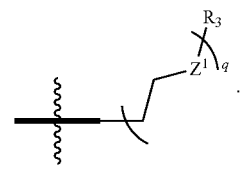

In other aspects, $Z^1$ is O. In yet other aspects, $R^3$ is a branched $C_{1-20}$ alkyl.

In one embodiment, the compound is

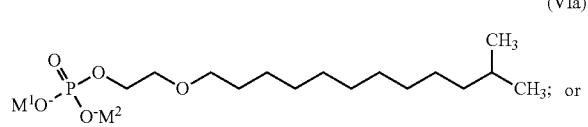

(VIa)

or

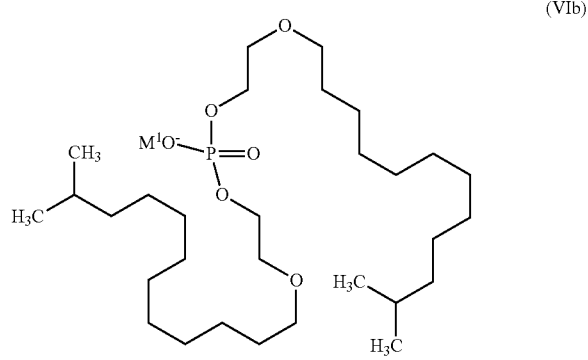

(VIb)

wherein $M^1$ and $M^2$ when they are present are each independently $H^+$, $Li^+$, $Na^+$, $K^+$, or $(C_{1-8}\ alkyl)_4N^+$. In one aspect, the compound of formula (VI) is HORDAPHOS® 1306 (alkyl polyethylene glycol ether phosphoric acid mono/diester), HOSTAPHAT® 1306 (alkyl polyethylene glycol ether phosphoric acid mono/diester), or MULTI-TROPE™ 1214 (PEG-4 decyl phosphate poly(oxy-1,2-ethanediyl), α-hydro-ω-hydroxy-, mono-C8-10-alkyl ethers, phosphates).

The present invention is also directed to a synergistic composition comprising: a) a lipopeptide; and b) a zwitterionic compound with a quaternary amine and a carboxylate; or an agriculturally acceptable salt, metal complex or metalloid complex thereof. In some aspects, the zwitterionic compound is of formula (VII):

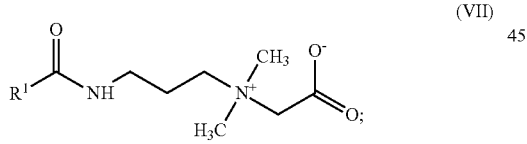

(VII)

wherein $R^1$ is a linear or branched $C_{1-20}$ alkyl or a linear or branched $C_{2-20}$ alkene;
or an agriculturally acceptable salt, metal complex or metalloid complex thereof.

In one embodiment, $R^1$ is a linear $C_{1-20}$ alkyl. In another embodiment, the compound is

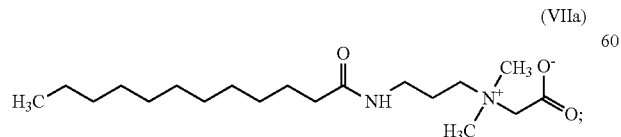

(VIIa)

or an agriculturally acceptable salt, metal complex or metalloid complex thereof. In certain aspects, the compound is GENAGEN® CAB 818 (cocoamidopropyl betaine (C8-C18)) or GENAGEN® KB (C12-C14 lauryl dimethyl betaine).

In another embodiment, the present invention provides a synergistic composition comprising: a) a lipopeptide; and b) a trisiloxane. The trisiloxane can be a compound of formula (VIII)

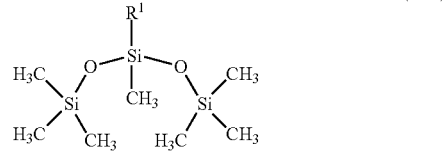

(VIII)

wherein
$R^1$ is a linear or branched $C_{1-20}$ alkyl, a linear or branched $C_{2-20}$ alkene, or

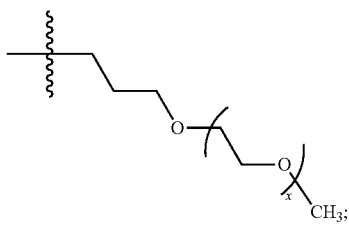

and
x is an integer between 1 and 12;
or an agriculturally acceptable salt, metal complex or metalloid complex thereof.

In some aspects, $R^1$ is

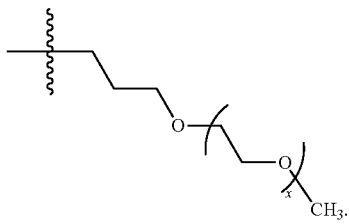

In some embodiments, the compound of formula (VIII) is a trisiloxane ethoxylate. In one embodiment, x is 8. In another embodiment, the compound is SILWET® L-77 (polyalkyleneoxide modified heptamethyltrisiloxane).

In another embodiment, $R^1$ is

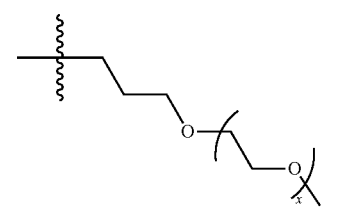

In some embodiments, the compound of formula (VII) is a trisiloxane alkoxylate. In one embodiment, x is 8. In another embodiment, the compound is SILWET® 408 (trisiloxane alkoxylate), SILWET® 618 (trisiloxane alkoxylate), or SILWET® 625 (trisiloxane alkoxylate).

In some embodiments, the lipopeptide is part of or an extract of a fungicidal lipopeptide-producing fermentation product. The lipopeptide-producing fermentation product may be a *Bacillus* sp. In one aspect, the *Bacillus* sp. is *Bacillus subtilis* or *Bacillus amyloliquefaciens*. In another aspect, the *Bacillus* sp. is *Bacillus subtilis* QST713 or a fungicidal mutant strain derived therefrom. In one embodiment, the fungicidal mutant strain has a genomic sequence with greater than about 90% sequence identity to *Bacillus subtilis* QST713.

In other aspects, the *Bacillus* sp. is *Bacillus amyloliquefaciens* strain D747; *Bacillus subtilis* MBI600; *Bacillus subtilis* Y1336; *Bacillus amyloliquefaciens* strain FZB42; or *Bacillus subtilis* var. *amyloliquefaciens* FZB24.

In some embodiments, the lipopeptide is an iturin-type compound, a surfactin-type compound, a fengycin-type compound, a fusaricidin, or a combination thereof. In one aspect, the lipopeptide is an iturin-type compound. The iturin-type compound may be bacillomycin D, bacillomycin F, bacillomycin L, bacillomycin LC (bacillopeptin), mycosubtilin, iturin A, iturin $A_L$, or iturin C.

In another aspect, the lipopeptide is a fengycin-type compound. The fengycin-type compound may be fengycin A, fengycin B, plipastatin A, plipastatin B, or an agrastatin.

In yet another aspect, the lipopeptide is a surfactin-type compound. The surfactin-type compound may be esperin, lichenysin, pumilacidin, or surfactin.

In some embodiments, the present invention is directed to a method of controlling fungal harmful organisms and/or bacterial harmful organisms in a plant, the method comprising applying an effective amount of a synergistic composition described herein to the plant, to a part of the plant and/or to a locus on which the plant or plant part grows.

In some aspects, the fungal harmful organisms are *Phytophthora infestans* and/or *Botrytis cinerea* and/or *Plasmopara viticola* and/or *Sphaerotheca fuliginea* and/or *Venturia inaequalis* and/or *Alternaria solani* and/or *Uromyces appendiculatus* and/or *Phakopsora pachyrhizi*.

In other aspects, the bacterial harmful organisms are *Acidovorax avenae*, *Burkholderia glumae* and/or *Xanthomonas campestris* pv. *oryzae* in rice, *Candidatus Liberibacter* spec. and/or *Xanthomonas axonopodis* pv. *citri* and/or *Xanthomonas campestris* pv. *vesicatoria* and/or *Xylella fastidiosa* in citrus, *Pseudomonas syringae* pv. *actinidae* in Kiwi, *Xanthomonas campestris* and/or *Xanthomonas campestris* pv. *pruni* in peaches, *Pseudomonas syringae* pv. *glycinea* and/or *Xanthomonas axonopodis* pv. *glycines* in soybeans, *Burkholderia* spec. and/or *Xanthomonas transluscens* in cereals, *Pseudomonas syringae*, *Pseudomonas syringae* pv. *tomato* and/or *Xanthomonas campestris* in tomatoes, *Pseudomonas syringae* and/or *Pseudomonas syringae* pv. *lachrymans* in cucumbers, *Erwinia atroseptica*, *Erwinia carotovora* and/or *Streptomyces scabies* in potatoes.

In yet other aspects, the plant is selected from the group consisting of apples, bananas, citrus, kiwi, melons, peaches, pears, pineapple, pome fruit, pomegranate, cabbage, cauliflower, cucumbers, cucurbits, tomatoes, potatoes, wheat, rice and soybeans.

The present invention also provides a method of treating a plant to control a fungal disease, wherein the method comprises applying to the plant, to a part of the plant and/or to a locus of the plant a composition comprising a compound of formula (I):

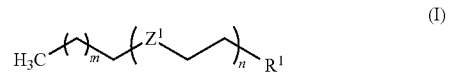

or a salt thereof, wherein
m is an integer between 0 and 18;
n is an integer between 1 and 10;
$Z^1$ is $CH_2$, S, O, or NH;
and $R^1$ is a sulfate, sulfonate, phosphate, or carboxylate.

In another aspect, the present invention is directed to a method of treating a plant to control a fungal disease, wherein the method comprises applying to the plant, to a part of the plant and/or to a locus of the plant a composition comprising a compound of formula (II):

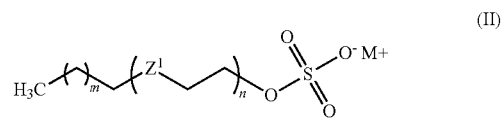

wherein
m is an integer between 0 and 18;
n is an integer between 1 and 10;
$Z^1$ is $CH_2$, S, O, or NH; and
when it is present, M+ is selected from the group consisting of H+, Li+, Na+, K+, and $NH_4$+.

In some embodiments, the method further comprises simultaneously or sequentially applying to the plant, to the part of the plant and/or to the locus of the plant a lipopeptide.

In one embodiment, the lipopeptide is part of or is an extract of a fermentation product from *Bacillus* species bacteria, such as those described herein. In another instance of this embodiment, prior to making the combination, a lipopeptide-producing bacteria is selected, such as a *Bacillus* species strain or *Paenibacillus* species strain, and a fermentation product containing lipopeptides is produced using this lipopeptide-producing bacteria, and such fermentation product or an extract thereof is used to make the combination. In one embodiment, such fermentation product would include one or more of the following lipopeptides: surfactin-type compounds, fengycin-type compounds, iturin-type compounds and/or fusaricidin. In a more particular embodiment, such fermentation product would include one or more of the following lipopeptides: surfactin, plipastatin, fengycin, iturin and/or bacillomycin.

In certain aspects, the methods disclosed herein are used to control a fungal disease wherein the fungal disease is Grey Mould caused by *Botrytis cinerea*, Late Blight caused by *Phytophthora infestans*, Downy Mildew caused by *Plasmopara viticola*, Powdery Mildew caused by *Sphaerotheca fuliginea*, Apple Scab caused by *Venturia inaequalis*, Bean Rust caused by *Uromyces appendiculatus*, or Soybean Rust caused by *Phakopsora pachyrhizi*.

In certain aspects, the lipopeptide is part of or is an extract of a fermentation product from *Bacillus* species bacteria, such as those described herein. In another instance of this embodiment, prior to making the combination, a lipopeptide-producing bacteria is selected, such as a *Bacillus* species strain or *Paenibacillus* species strain, and a fermentation product containing lipopeptides is produced using this lipopeptide-producing bacteria, and such fermentation product or an extract thereof is used to make the combination. In one embodiment, such fermentation product would include one or more of the following lipopeptides: surfactin-type compounds, fengycin-type compounds, iturin-type compounds and/or fusaricidin. In a more particular embodiment, such fermentation product would include one or more of the following lipopeptides: surfactin, plipastatin, fengycin, iturin and/or bacillomycin.

In other aspects, the fungicidal compositions of the present invention comprise a lipopeptide-producing strain of *Bacillus subtilis* or *Bacillus amyloliquefaciens*. The strain of *Bacillus subtilis* or *Bacillus amyloliquefaciens* may be part of fermentation product. In one embodiment, the lipopeptide from the lipopeptide-producing strain of *Bacillus subtilis* or *Bacillus amyloliquefaciens* is an iturin-type compound, a surfactin-type compound, a fengycin-type compound, or a combination thereof.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondite, P. triticina, P. graminis* or *P. striiformis* or *P. hordei*; *Uromyces* species, for example *Uromyces appendiculatus*;

diseases caused by pathogens from the group of the Oomycetes, for example *Albugo* species, for example *Algubo candida*; *Bremia* species, for example *Bremia lactucae*; *Peronospora* species, for example *Peronospora pisi, P. parasitica* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladosporium* species, for example *Cladosporium cucumerinum*; *Cochliobolus* species, for example *Cochliobolus sativus* (conidia form: *Drechslera*, Syn: *Helminthosporium*), *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans, Leptosphaeria nodorum*; *Magnaporthe* species, for example *Magnaporthe grisea*; *Microdochium* species, for example *Microdochium nivale*; *Mycosphaerella* species, for example *Mycosphaerella graminicola, M. arachidicola* and *M. fifiensis*; *Phaeosphaeria* species, for example *Phaeosphaeria nodorum*; *Pyrenophora* species, for example *Pyrenophora teres, Pyrenophora tritici repentis*; *Ramularia* species, for example *Ramularia collo-cygni, Ramularia areola*; *Rhynchosporium* species, for example *Rhynchosporium secalis*; *Septoria* species, for example *Septoria apii, Septoria lycopersii*; *Typhula* species, for example *Typhula incarnata*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*;

seed and soilborne decay, mould, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma lingam*; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani*; *Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnata*; *Verticillium* species, caused for example by *Verticillium dahliae*;

cancers, galls and witches' broom caused, for example, by *Nectria* species, for example *Nectria galligena*;

wilt diseases caused, for example, by *Monilinia* species, for example *Monilinia laxa*;

leaf blister or leaf curl diseases caused, for example, by *Exobasidium* species, for example *Exobasidium vexans*;

*Taphrina* species, for example *Taphrina deformans*;

decline diseases of wooden plants caused, for example, by Esca disease, caused for example by *Phaemoniella clamydospora, Phaeoacremonium aleophilum* and *Fomitiporia mediterranea; Eutypa* dyeback, caused for example by *Eutypa lata; Ganoderma* diseases caused for example by *Ganoderma boninense; Rigidoporus* diseases caused for example by *Rigidoporus lignosus;* diseases of flowers and seeds caused, for example, by *Botrytis* species, for example *Botrytis cinerea;* diseases of plant tubers caused, for example, by *Rhizoctonia* species, for example *Rhizoctonia solani; Helminthosporium* species, for example *Helminthosporium solani;*

Club root caused, for example, by *Plasmodiophora* species, for example *Plamodiophora brassicae;* diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora.*

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), *cercospora* leaf spot and blight (*Cercospora kikuchii*), *choanephora* leaf blight (*Choanephora infundibulifera trispora* (Syn.)), *dactuliophora* leaf spot (*Dactuliophora glycines*), downy mildew (*Peronospora manshurica*), *drechslera* blight (*Drechslera glycini*), frogeye leaf spot (*Cercospora sojina*), *leptosphaerulina* leaf spot (*Leptosphaerulina trifolii*), phyllostica leaf spot (*Phyllosticta sojaecola*), pod and stem blight (*Phomopsis sojae*), powdery mildew (*Microsphaera diffusa*), *pyrenochaeta* leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), *stemphylium* leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive compositions can be used for curative or protective/preventive control of phytopathogenic fungi. The invention therefore also relates to curative and protective methods for controlling phytopathogenic fungi by the use of the inventive composition, which is applied to the seed, the plant or plant parts, the fruit or the soil in which the plants grow.

Compositions of the present invention are useful in various fungal control applications. The above-described compositions may be used to control fungal phytopathogens, post-harvest fungal pathogens, fungal pathogens of food or feed and human fungal pathogens.

In one embodiment, any of the above-described compositions are used to control target pathogens such as *Fusarium* species, *Botrytis* species, *Verticillium* species, *Rhizoctonia* species, *Trichoderma* species and *Pythium* species by applying the composition to plants, the area surrounding plants, or edible cultivated mushrooms, mushroom spawn or mushroom compost.

In another embodiment, compositions of the present invention are used to control post-harvest pathogens such as *Penicillium, Geotrichum, Aspergillus niger,* and *Colletotrichum* species.

In yet another embodiment, compositions of the present invention are used to control fungal pathogens that occur in food or feed, such as *Penicillium* species, *Aspergillus* species and *Fusarium* species.

The combinations according to the present invention are particularly suitable in the use for controlling bacterial harmful organisms. According to the present invention bacterial harmful organisms include inter alia bacteria causing damage to plants or to a part of a plant.

Bacteria include inter alia Actinobacteria and Proteobacteria and are selected from the families of the Burkholderiaceae, Xanthomonadaceae, Pseudomonadaceae, Enterobacteriaceae, Microbacteriaceae, and Rhizobiaceae.

According to the present invention the bacterial harmful organisms are particularly selected from the group consisting of:

*Acidovorax avenae* (=*Pseudomonas avenae, Pseudomonas avenae* subsp. *avenae, Pseudomonas rubrilineans*), including e.g., *Acidovorax avenae* subsp. *avenae* (=*Pseudomonas avenae* subsp. *avenae*), *Acidovorax avenae* subsp. *cattleyae* (=*Pseudomonas cattleyae*), *Acidovorax avenae* subsp. *citrulli* (=*Pseudomonas pseudoalcaligenes* subsp. *citrulli, Pseudomonas avenae* subsp. *citrulli*));

*Burkholderia* spec., including e.g., *Burkholderia andropogonis* (=*Pseudomonas andropogonis, Pseudomonas woodsii*), *Burkholderia caryophylli* (=*Pseudomonas caryophylli*), *Burkholderia cepacia* (=*Pseudomonas cepacia*), *Burkholderia gladioli* (=*Pseudomonas gladioli*), *Burkholderia gladioli* pv. *agaricicola* (=*Pseudomnas gladioli* pv. *agaricicola*), *Burkholderia gladioli* pv. *alliicola* (=*Pseusomonas gladioli* pv. *alliicola*), *Burkholderia gladioli* pv. *gladioli* (=*Pseudomonas gladioli, Pseudomonas gladioli* pv. *gladioli*), *Burkholderia glumae* (=*Pseudomonas glumae*), *Burkholderia plantarii* (=*Pseudomonas plantarii*) *Burkholderia solanacearum* (=*Ralstonia solanacearum*), and *Ralstonia* spp.;

*Liberibacter* spp., including *Candidatus Liberibacter* spec., including e.g., *Liberibacter africanus* (Laf), *Liberibacter americanus* (Lam), *Liberibacter asiaticus* (Las), *Liberibacter europaeus* (Leu), *Liberibacter psyllaurous, Liberibacter solanacearum* (Lso);

*Corynebacterium*, including e.g., *Corynebacterium fascians, Corynebacterium flaccumfaciens* pv. *flaccumfaciens, Corynebacterium michiganensis, Corynebacterium michiganense* pv. *tritici, Corynebacterium michiganense* pv. *nebraskense, Corynebacterium sepedonicum;*

*Erwinia* spec. including e.g., *Erwinia amylovora, Erwinia ananas, Erwinia carotovora* (=*Pectobacterium carotovorum*), *Erwinia carotovora* subsp. *atroseptica, Erwinia carotovora* subsp. *carotovora, Erwinia chrysanthemi, Erwinia chrysanthemi* pv. *zeae, Erwinia dissolvens, Erwinia herbicola, Erwinia rhapontic, Erwinia stewartiii, Erwinia tracheiphila, Erwinia uredovora;*

*Pseudomonas syringae*, including e.g., *Pseudomonas syringae* pv. *actinidiae* (Psa), *Pseudomonas syringae* pv. *atrofaciens, Pseudomonas syringae* pv. *coronafaciens,*

*Pseudomonas syringae* pv. *glycinea, Pseudomonas syringae* pv. *lachrymans, Pseudomonas syringae* pv. *maculicola Pseudomonas syringae* pv. *papulans, Pseudomonas syringae* pv. *striafaciens, Pseudomonas syringae* pv. *syringae, Pseudomonas syringae* pv. *tomato, Pseudomonas syringae* pv. *tabaci;*

*Streptomyces* spp., including e.g., *Streptomyces acidiscabies, Streptomyces albidoflavus, Streptomyces candidus* (=*Actinomyces candidus*), *Streptomyces caviscabies, Streptomyces collinus, Streptomyces europaeiscabiei, Streptomyces intermedius, Streptomyces ipomoeae, Streptomyces luridiscabiei, Streptomyces niveiscabiei, Streptomyces puniciscabiei, Streptomyces retuculiscabiei, Streptomyces scabiei, Streptomyces scabies, Streptomyces setonii, Streptomyces steliiscabiei, Streptomyces turgidiscabies, Streptomyces wedmorensis;*

*Xanthomonas axonopodis*, including e.g., *Xanthomonas axonopodis* pv. *alfalfae* (=*Xanthomonas alfalfae*), *Xanthomonas axonopodis* pv. *aurantifolii* (=*Xanthomonas fuscans* subsp. *aurantifolii*), *Xanthomonas axonopodis* pv. *allii* (=*Xanthomonas campestris* pv. *allii*), *Xanthomonas axonopodis* pv. *axonopodis, Xanthomonas axonopodis* pv. *bauhiniae* (=*Xanthomonas campestris* pv. *bauhiniae*), *Xanthomonas axonopodis* pv. *begoniae* (=*Xanthomonas campestris* pv. *begoniae*), *Xanthomonas axonopodis* pv. *betlicola* (=*Xanthomonas campestris* pv. *betlicola*), *Xanthomonas axonopodis* pv. *biophyti* (=*Xanthomonas campestris* pv. *biophyti*), *Xanthomonas axonopodis* pv. *cajani* (=*Xanthomonas campestris* pv. *cajani*), *Xanthomonas axonopodis* pv. *cassavae* (=*Xanthomonas cassavae, Xanthomonas campestris* pv. *cassavae*), *Xanthomonas axonopodis* pv. *cassiae* (=*Xanthomonas campestris* pv. *cassiae*), *Xanthomonas axonopodis* pv. *citri* (=*Xanthomonas citri*), *Xanthomonas axonopodis* pv. *citrumelo* (=*Xanthomonas alfalfae* subsp. *citrumelonis*), *Xanthomonas axonopodis* pv. *clitoriae* (=*Xanthomonas campestris* pv. *clitoriae*), *Xanthomonas axonopodis* pv. *coracanae* (=*Xanthomonas campestris* pv. *coracanae*), *Xanthomonas axonopodis* pv. *cyamopsidis* (=*Xanthomonas campestris* pv. *cyamopsidis*), *Xanthomonas axonopodis* pv. *desmodii* (=*Xanthomonas campestris* pv. *desmodii*), *Xanthomonas axonopodis* pv. *desmodiigangetici* (=*Xanthomonas campestris* pv. *desmodiigangetici*), *Xanthomonas axonopodis* pv. *desmodiilaxiflori* (=*Xanthomonas campestris* pv. *desmodiilaxiflori*), *Xanthomonas axonopodis* pv. *desmodiirotundifolii* (=*Xanthomonas campestris* pv. *desmodiirotundifolii*), *Xanthomonas axonopodis* pv. *dieffenbachiae* (=*Xanthomonas campestris* pv. *dieffenbachiae*), *Xanthomonas axonopodis* pv. *erythrinae* (=*Xanthomonas campestris* pv. *erythrinae*), *Xanthomonas axonopodis* pv. *fascicularis* (=*Xanthomonas campestris* pv. *fasciculari*), *Xanthomonas axonopodis* pv. *glycines* (=*Xanthomonas campestris* pv. *glycines*), *Xanthomonas axonopodis* pv. *khayae* (=*Xanthomonas campestris* pv. *khayae*), *Xanthomonas axonopodis* pv. *lespedezae* (=*Xanthomonas campestris* pv. *lespedezae*), *Xanthomonas axonopodis* pv. *maculifoliigardeniae* (=*Xanthomonas campestris* pv. *maculifoliigardeniae*), *Xanthomonas axonopodis* pv. *malvacearum* (=*Xanthomonas citri* subsp. *malvacearum*), *Xanthomonas axonopodis* pv. *manihotis* (=*Xanthomonas campestris* pv. *manihotis*), *Xanthomonas axonopodis* pv. *martyniicola* (=*Xanthomonas campestris* pv. *martyniicola*), *Xanthomonas axonopodis* pv. *melhusii* (=*Xanthomonas campestris* pv. *melhusii*), *Xanthomonas axonopodis* pv. *nakataecorchori* (=*Xanthomonas campestris* pv. *nakataecorchori*), *Xanthomonas axonopodis* pv. *passiflorae* (=*Xanthomonas campestris* pv. *passiflorae*), *Xanthomonas axonopodis* pv. *patelii* (=*Xanthomonas campestris* pv. *patelii*), *Xanthomonas axonopodis* pv. *pedalii* (=*Xanthomonas campestris* pv. *pedalii*), *Xanthomonas axonopodis* pv. *phaseoli* (=*Xanthomonas campestris* pv. *phaseoli, Xanthomonas phaseoli*), *Xanthomonas axonopodis* pv. *phaseoli* var. *fuscans* (=*Xanthomonas fuscans*), *Xanthomonas axonopodis* pv. *phyllanthi* (=*Xanthomonas campestris* pv. *phyllanthi*), *Xanthomonas axonopodis* pv. *physalidicola* (=*Xanthomonas campestris* pv. *physalidicola*), *Xanthomonas axonopodis* pv. *poinsettiicola* (=*Xanthomonas campestris* pv. *poinsettiicola*), *Xanthomonas axonopodis* pv. *punicae* (=*Xanthomonas campestris* pv. *punicae*), *Xanthomonas axonopodis* pv. *rhynchosiae* (=*Xanthomonas campestris* pv. *rhynchosiae*), *Xanthomonas axonopodis* pv. *ricini* (=*Xanthomonas campestris* pv. *ricini*), *Xanthomonas axonopodis* pv. *sesbaniae* (=*Xanthomonas campestris* pv. *sesbaniae*), *Xanthomonas axonopodis* pv. *tamarindi* (=*Xanthomonas campestris* pv. *tamarindi*), *Xanthomonas axonopodis* pv. *vasculorum* (=*Xanthomonas campestris* pv. *vasculorum*), *Xanthomonas axonopodis* pv. *vesicatoria* (=*Xanthomonas campestris* pv. *vesicatoria, Xanthomonas vesicatoria*), *Xanthomonas axonopodis* pv. *vignaeradiatae* (=*Xanthomonas campestris* pv. *vignaeradiatae*), *Xanthomonas axonopodis* pv. *vignicola* (=*Xanthomonas campestris* pv. *vignicola*), *Xanthomonas axonopodis* pv. *vitians* (=*Xanthomonas campestris* pv. *vitians*);

*Xanthomonas campestris* pv. *musacearum, Xanthomonas campestris* pv. *pruni* (=*Xanthomonas arboricola* pv. *pruni*), *Xanthomonas fragariae;*

*Xanthomonas translucens* (=*Xanthomonas campestris* pv. *hordei*) including e.g., *Xanthomonas translucens* pv. *arrhenatheri* (=*Xanthomonas campestris* pv. *arrhenatheri*), *Xanthomonas translucens* pv. *cerealis* (=*Xanthomonas campestris* pv. *cerealis*), *Xanthomonas translucens* pv. *graminis* (=*Xanthomonas campestris* pv. *graminis*), *Xanthomonas translucens* pv. *phlei* (=*Xanthomonas campestris* pv. *phlei*), *Xanthomonas translucens* pv. *phleipratensis* (=*Xanthomonas campestris* pv. *phleipratensis*), *Xanthomonas translucens* pv. *poae* (=*Xanthomonas campestris* pv. *poae*), *Xanthomonas translucens* pv. *secalis* (=*Xanthomonas campestris* pv. *secalis*), *Xanthomonas translucens* pv. *translucens* (=*Xanthomonas campestris* pv. *translucens*), *Xanthomonas translucens* pv. *undulosa* (=*Xanthomonas campestris* pv. *undulosa*).

*Xanthomonas oryzae, Xanthomonas oryzae* pv. *oryzae* (=*Xanthomonas campestris* pv. *oryzae*), *Xanthomonas oryzae* pv. *oryzicola* (=*Xanthomonas campestris* pv. *oryzicola*).

*Xylella fastidiosa* from the family of Xanthomonadaceae.

Preferably, the bacterial harmful organisms are selected from the group consisting of:

*Acidovorax avenae* subsp. *avenae* (=*Pseudomonas avenae* subsp. *avenae*), *Acidovorax avenae* subsp. *citrulli* (=*Pseudomonas pseudoalcaligenes* subsp. *citrulli, Pseudomonas avenae* subsp. *citrulli*), *Burkholderia glumae* (=*Pseudomonas glumae*), *Burkholderia solanacearum* (=*Ralstonia solanacearum*), *Corynebacterium michiganense* pv. *nebraskense, Erwinia amylovora, Erwinia carotovora* (=*Pectobacterium carotovorum*), *Erwinia carotovora* subsp. *atroseptica, Erwinia carotovora* subsp. *carotovora, Erwinia chrysanthemi, Erwinia chrysanthemi* pv. *zeae, Erwinia herbicola, Erwinia stewartiii, Erwinia uredovora, Liberibacter* spp., *Candidatus Liberibacter* spec. as defined above, *Pseudomonas syringae, Pseudomonas syringae* pv. *actinidiae* (Psa), *Pseudomonas syringae* pv. *glycinea, Pseudomonas syringae* pv. *lachrymans, Pseudomonas syringae* pv. *papulans, Pseudomonas syringae* pv. *syringae,*

*Pseudomonas syringae* pv. *tomato*, *Pseudomonas syringae* pv. *tabaci*, *Ralstonia* spp., *Streptomyces scabies*, *Xanthomonas axonopodis* pv. *citri*, *Xanthomonas axonopodis* pv. *glycines* (=*Xanthomonas campestris* pv. *glycines*), *Xanthomonas axonopodis* pv. *punicae* (=*Xanthomonas campestris* pv. *punicae*), *Xanthomonas axonopodis* pv. *vesicatoria* (=*Xanthomonas campestris* pv. *vesicatoria*, *Xanthomonas vesicatoria*), *Xanthomonas campestris*, *Xanthomonas campestris* pv. *musacearum*, *Xanthomonas campestris* pv. *pruni* (=*Xanthomonas arboricola* pv. *pruni*), *Xanthomonas fragariae*, *Xanthomonas translucens* pv. *translucens* (=*Xanthomonas campestris* pv. *translucens*), *Xanthomonas oryzae* pv. *oryzae* (=*Xanthomonas campestris* pv. *oryzae*), *Xylella fastidiosa*.

In a more preferred aspect of the present invention the bacterial harmful organisms are selected from the group consisting of:

*Acidovorax avenae* (=*Pseudomonas avenae*, *Pseudomonas avenae* subsp. *avenae*, *Pseudomonas rubrilineans*) as defined above, *Burkholderia* spec. as defined above, *Burkholderia glumae*, *Corynebacterium* as defined above, *Erwinia* spec. as defined above, *Erwinia amylovora*, *Erwinia carotovora* (=*Pectobacterium carotovorum*), *Erwinia carotovora* subsp. *atroseptica*, *Erwinia carotovora* subsp. *carotovora*, *Erwinia chrysanthemi*, *Erwinia chrysanthemi* pv. *zeae*, *Erwinia herbicola*, *Erwinia stewartiii*, *Erwinia uredovora*, *Liberibacter* spp., *Candidatus Liberibacter* spec. as defined above, *Pseudomonas syringae* as defined above, *Pseudomonas syringae* pv. *actinidae*, *Pseudomonas syringae* pv. *glycinea*, *Pseudomonas syringae* pv. *tomato*, *Pseudomonas syringae* pv. *lachrymans*, *Ralstonia* spp., *Streptomyces* spp., *Streptomyces scabies*, *Xanthomonas* spp., *Xanthomonas axonopodis* as defined above, *Xanthomonas axonopodis* pv. *citri*, *Xanthomonas axonopodis* pv. *glycines*, *Xanthomonas campestris*, *Xanthomonas campestris* pv. *musacearum*, *Xanthomonas campestris* pv. *pruni* (=*Xanthomonas arboricola* pv. *pruni*), *Xanthomonas fragariae*, *Xanthomonas translucens* (=*Xanthomonas campestris* pv. *hordei*), *Xanthomonas oryzae* pv. *oryzae* (=*Xanthomonas campestris* pv. *oryzae*) and *Xylella fastidiosa* as defined above.

Even more preferred is a selection consisting of:

*Acidovorax avenae*, *Burkholderia* spec., *Burkholderia glumae*, *Corynebacterium*, *Erwinia* spec., *Liberibacter* spp., *Candidatus Liberibacter* spec., *Pseudomonas syringae*, *Pseudomonas syringae* pv. *actinidae*, *Pseudomonas syringae* pv. *glycinea*, *Pseudomonas syringae* pv. *tomato*, *Pseudomonas syringae* pv. *lachrymans*, *Ralstonia* spp., *Streptomyces* spp., *Xanthomonas* spp., *Xanthomonas axonopodis*, *Xanthomonas axonopodis* pv. *citri*, *Xanthomonas axonopodis* pv. *glycines*, *Xanthomonas campestris*, *Xanthomonas campestris* pv. *musacearum*, *Xanthomonas campestris* pv. *pruni*, *Xanthomonas fragariae*, *Xanthomonas translucens*, *Xanthomonas oryzae* pv. *oryzae* (=*Xanthomonas campestris* pv. *oryzae*) and *Xylella fastidiosa*.

In an even more preferred aspect of the present invention the bacterial harmful organisms are selected from the group consisting of:

*Acidovorax avenae*, *Burkholderia* spec., *Burkholderia glumae*, *Corynebacterium*, *Erwinia amylovora*, *Erwinia carotovora*, *Erwinia carotovora* subsp. *atroseptica*, *Erwinia carotovora* subsp. *carotovora*, *Erwinia chrysanthemi*, *Erwinia chrysanthemi* pv. *zeae*, *Erwinia herbicola*, *Erwinia stewartiii*, *Erwinia uredovora*, *Liberibacter* spp., *Candidatus Liberibacter* spec., *Pseudomonas syringae*, *Pseudomonas syringae* pv. *actinidae*, *Pseudomonas syringae* pv. *glycinea*, *Pseudomonas syringae* pv. *lachrymans*, *Pseudomonas syringae* pv. *tomato*, *Ralstonia* spp., *Streptomyces scabies*, *Xanthomonas axonopodis*, *Xanthomonas axonopodis* pv. *citri*, *Xanthomonas axonopodis* pv. *glycines*, *Xanthomonas campestris*, *Xanthomonas campestris* pv. *musacearum*, *Xanthomonas campestris* pv. *pruni*, *Xanthomonas fragariae*, *Xanthomonas translucens*, *Xanthomonas oryzae* pv. *oryzae* (=*Xanthomonas campestris* pv. *oryzae*) and *Xylella fastidiosa*.

The most preferred selection comprises the group consisting of:

*Burkholderia glumae*, *Liberibacter* spp., *Candidatus Liberibacter* spec., *Xanthomonas axonopodis* pv. *citri*, *Pseudomonas syringae*, *Pseudomonas syringae* pv. *actinidae*, *Pseudomonas syringae* pv. *glycinea*, *Pseudomonas syringae* pv. *lachrymans*, *Pseudomonas syringae* pv. *tomato*, *Ralstonia* spp., *Streptomyces scabies*, *Xanthomonas axonopodis* pv. *glycines*, *Xanthomonas campestris* pv. *pruni*, *Xanthomonas campestris*, *Xanthomonas oryzae* pv. *oryzae* (=*Xanthomonas campestris* pv. *oryzae*) and *Xylella fastidiosa*.

In one embodiment, the present invention provides a composition comprising a synergistic fungicidal combination of a lipopeptide and a compound of formula (I):

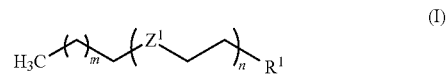

(I)

or a salt thereof, wherein
m is an integer between 0 and 18;
n is an integer between 1 and 10;
$Z^1$ is $CH_2$, S, O, or NH; and
$R^1$ is a sulfate, sulfonate, phosphate, or carboxylate.

In some implementations, $R^1$ is a sulfate, and in others $Z^1$ is O. In yet others, n is an integer between 1 and 5 while in others m is an integer between 8 and 16.

In another embodiment, the present invention provides a composition comprising a synergistic fungicidal combination of a lipopeptide and a compound of formula (II):

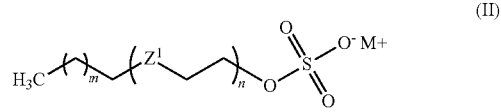

(II)

wherein
m is an integer between 0 and 18;
n is an integer between 1 and 10;
$Z^1$ is $CH_2$, S, O, or NH; and
when it is present, M+ is selected from the group consisting of H+, Li+, Na+, K+, and $NH_4$+.

In certain aspects, $Z^1$ is O. In other aspects, m is an integer between 8 and 16.

In another embodiment, the present invention provides a composition comprising a synergistic fungicidal combination of a lipopeptide and a compound of formula (III):

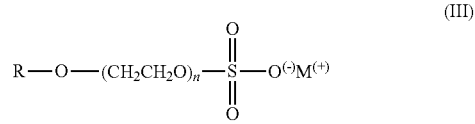

(III)

wherein

R is an alkyl group;

n is an integer of 1 to 10 and means the number of ethyleneoxy units in the (poly)ethyleneoxy bridge; and $M^{(+)}$ is a cation, preferably $H^{(+)}$ or a metal ion or an ammonium ion.

In certain aspects, the present invention provides a composition comprising a synergistic fungicidal combination of a lipopeptide and a compound of formula (I):

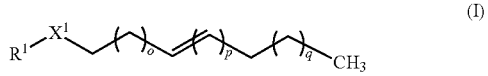

(I)

or a stereoisomer thereof, wherein o is an integer between 0 and 10;

p is an integer between 0 and 2;

q is an integer between 0 and 10;

$X^1$ is an ester bond or a glycosidic bond with an —OH from $R^1$; and $R^1$ is a pentose, a hexose, or a sorbitan substituent, optionally substituted with a pentose, hexose, sorbitan, $C_1$ to $C_{18}$ alkyl, or $C_1$ to $C_{18}$ alkenyl substituent.

The weight to weight ratio of the compound and the lipopeptide (or, alternatively, the lipopeptide component (e.g., a lipopeptide-producing fermentation broth, a crude extract containing lipopeptides; a purified or semi-purified lipopeptide extract; or chemically synthesized or derivatized pure lipopeptide(s)) is in the range of about 1000:1 to about 1:1000, preferably in the range of about 500:1 to about 1:500, more preferably in the range of about 100:1 to about 1:100. Other preferred ratios are between about 20:1 and about 1:20, between about 10:1 and about 1:10, between about 5:1 and about 1:5, and between about 3:1 and about 1:3.

A ratio of about 100:1 means about 100 weight parts of compound (e.g., sorbitan ester or alkyl glucoside) and about 1 weight part of the lipopeptide or lipopeptide component such as the *Bacillus subtilis* QST713 fermentation product are combined (either as a solo formulation, a combined formulation or by separate applications to plants so that the combination is formed on the plant).

In one embodiment, the weight ratio of compound of the present invention to pure lipopeptides comprised of one or more compounds from one or more of the following families of compounds, surfactin-type compounds, iturin-type compounds, fengycin-type compounds, and/or fusaricidins is in the range of about 1000:1 to about 1:1000, preferably in the range of about 500:1 to about 1:500, more preferably in the range of about 100:1 to about 1:100, in the range of about 50:1 to about 1:50, or in the range of about 25:1 to about 1:25. In some embodiments, the weight to weight ratio of any of the above-described combinations of the compound and the lipopeptide or lipopeptide component is about 100:1 to about 1:100; in others it is about 10:1 to about 1:10; in still others it is about 5:1 to about 1:5; in yet others it is about 3:1 to about 1:3; and in yet others it is about 1:1.

In another embodiment, the weight ratio of compound(s) of the present invention to lipopeptide-producing fermentation broth (e.g., *Bacillus subtilis* QST713 fermentation broth) is in the range of about 500:1 to about 1:500, more preferably in the range of about 100:1 to about 1:100, in the range of about 50:1 to about 1:50, or in the range of about 25:1 to about 1:25. In one aspect, the weight ratio of compound(s) of the present invention to lipopeptide-producing fermentation broth is in the range of 24:1 to 3:1 as shown in Example 2 where 3000 ppm of a mixture of SPAN® 20 (sorbitan monolaurate) and TWEEN® 20 (polyethylene glycol sorbitan monolaurate) was combined with between 1000 ppm and 125 ppm of the SERENADE® ASO fermentation broth containing (1.67%) dried *Bacillus subtilis* QST713.

In some embodiments, the weight to weight ratio of a) the compound and b) the lipopeptide (or, alternatively, the lipopeptide component (e.g., a lipopeptide-producing fermentation broth, a crude extract containing lipopeptides; a purified or semi-purified lipopeptide extract; or chemically synthesized or derivatized pure lipopeptide(s)) is about 1:5 to about 1:120. In certain aspects, this weight to weight ratio is about 1:5, about 1:10, about 1:15, about 1:19, about 1:20, about 1:24, about 1:25, about 1:30, about 1:50, about 1:60, about 1:75, or about 1:120.

The compound (e.g., sorbitan ester or alkyl glucoside) and the lipopeptide or lipopeptide component are used or employed in a synergistic weight ratio. The skilled person understands that these ratios refer to the ratio within a combined-formulation as well as to the calculative ratio of the compound (e.g., sorbitan ester or alkyl glucoside) described herein and the lipopeptide or lipopeptide component when both components are applied as mono-formulations to a plant to be treated. The skilled person can calculate this ratio by simple mathematics since the volume and the amount of the compound (e.g., sorbitan ester or alkyl glucoside) and the lipopeptide or lipopeptide component, respectively, in a mono-formulation is known to the skilled person.

The ratio can be calculated based on the amount of the compound (e.g., sorbitan ester or alkyl glucoside), at the time point of applying said component of a combination according to the invention to a plant or plant part and the amount of and the lipopeptide or lipopeptide component shortly prior (e.g., 48 h, 24 h, 12 h, 6 h, 2 h, 1 h) or at the time point of applying said component of a combination according to the invention to a plant or plant part. The application of the compound (e.g., sorbitan ester or alkyl glucoside) and the lipopeptide or lipopeptide component to a plant or a plant part can take place simultaneously or at different times as long as both components are present on or in the plant after the application(s).

In some aspects, the compound (e.g., sorbitan ester or alkyl glucoside) and the lipopeptide or lipopeptide component are heated for about 1hr, 2 hr, or 3 hr after being combined or mixed together. The mixture or combination may be heated to about 40° C., about 50° C., about 60° C., about 70° C., about 80° C., about 90° C., or about 100° C.

In other aspects, the compound (e.g., sorbitan ester or alkyl glucoside) and the lipopeptide or lipopeptide component are equilibrated for at least 12 hours, at least 24 hours, or at least 48 hours after mixing and/or heating.

In one embodiment, the synergistic fungicidal combination comprises a lipopeptide and an agriculturally acceptable detergent. The detergent may be any detergent known in the art for use in agricultural formulations having the purpose, for example, of causing the formulation to stick to the surface of the target plant. It is to be appreciated that preferred detergents are completely biodegradable and environmentally friendly.

In another embodiment, the synergistic fungicidal combination comprises a lipopeptide and an agriculturally acceptable nonionic amphiphile or surfactant. There are a number of nonionic amphiphiles or surfactants commonly used in biological situations such as, for example, polyoxyethylene sorbitan fatty acid ethers (e.g., sold under the trade name TWEEN®), and sorbitan fatty acid ethers (e.g., sold under the trade name SPAN®).

A particularly useful group of surfactants are the sorbitan-based non-ionic surfactants. These surfactants are prepared by dehydration of sorbitol to give 1,4-sorbitan which is then reacted with one or more equivalents of a fatty acid. The fatty-acid-substituted moiety may be further reacted with ethylene oxide to give a second group of surfactants. The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common names for these surfactants include, for example, sorbitan monolaurate, sorbitan monopalmitate, sorbitan monestearate, sorbitan monooleate, sorbitan sesguioleate, and sorbitan trioleate. These surfactants are commercially available under the name SPAN® or ARLACEL®, usually with a letter or number designation which distinguishes between the various mono, di- and triester substituted sorbitans.

SPAN® and ARLACEL® surfactants are hydrophilic and are generally soluble or dispersible in oil. They are also soluble in most organic solvents. In water they are generally insoluble but dispersible. Generally these surfactants will have hydrophilic-lipophilic balance (HLB) number between 1.8 and 8.6. Such surfactants can be readily made by means known in the art or are commercially available.

A related group of surfactants comprises polyoxyethylene sorbitan monoesters and polyoxyethylene sorbitan triesters. These materials are prepared by addition of ethylene oxide to a 1,4-sorbitan monoester or triester. The addition of polyoxyethylene converts the lipophilic sorbitan mono- or triester surfactant to a hydrophilic surfactant generally soluble or dispersible in water and soluble to varying degrees in organic liquids.

These materials, commercially available under the mark TWEEN®, are useful for preparing oil-in-water emulsions and dispersions, or for the solubilization of oils. The TWEEN® surfactants may be combined with a related sorbitan monoester or triester surfactants to promote emulsion stability. TWEEN® surfactants are commercially available from a number of manufacturers.

A third group of non-ionic surfactants which could be used alone or in conjunction with SPAN®, ARLACEL® and TWEEN® surfactants are the polyoxyethylene fatty acids made by the reaction of ethylene oxide with a long-chain fatty acid. The most commonly available surfactant of this type is sold under the name MYRJ® and is a polyoxyethylene derivative of stearic acid. MYRJ® surfactants are hydrophilic and soluble or dispersible in water like TWEEN® surfactants. The MYRJ® surfactants may be blended with TWEEN® surfactants or with TWEEN®/SPAN® or ARLACEL® surfactant mixtures for use in forming emulsions. MYRJ® surfactants can be made by methods known in the art or are available commercially.

A fourth group of polyoxyethylene-based non-ionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ®. BRIJ® surfactants may be hydrophilic or lipophilic depending on the size of the polyoxyethylene moiety in the surfactant. While the preparation of these compounds is available from the art, they are also readily available from commercial sources.

Other non-ionic surfactants which could be used in the practice of this invention include polyoxyethylene, polyol fatty acid esters, polyoxyethylene ether, polyoxypropylene fatty ethers, bee's wax derivatives containing polyoxyethylene, polyoxyethylene lanolin derivative, polyoxyethylene fatty acid glycerides, and glycerol fatty acid esters or other polyoxyethylene acid alcohol or ether derivatives of long-chain fatty acids.

In some aspects, the compound of formula (I) is an alkyl glycoside, and in others it is an alkyl glucoside. Examples of alkyl glucosides that may be used in the present invention are decyl glucoside, octyl glucoside, dodecyl glucoside and combinations thereof.

In other aspects, the compound of formula (I) is a sorbitan ester. Non-limiting examples of sorbitan esters include sorbitan monolaurate, polyoxyethylene sorbitan monooleate, sorbitan monopalmitate, sorbitan sesquioleate, sorbitan trioleate, sorbitan monostearate, and sorbitan tristearate.

In another aspect, the present invention is directed to a synergistic composition comprising a) a lipopeptide; and b) synthetic latex. In one aspect, the synthetic latex is STICMAN® (synthetic latex). In yet another aspect, the present invention provides a synergistic composition comprising a) a lipopeptide; and b) a quaternary amine. In one embodiment, the quaternary amine is cocoamidopropyl betaine.

In some embodiments, the present invention provides a synergistic composition comprising a) a lipopeptide; and b) an alkyl polyglycoside. In one aspect, the alkyl polyglycoside is a $C_{8-10}$ alkyl polyglycoside. In one embodiment, the alkyl polyglycoside is AGNIQUE® PG8107G ($C_{8-10}$ alkyl polyglycoside).

In certain embodiments, the present invention provides a synergistic composition comprising a) a lipopeptide; and b) rapeseed oil methyl ester; castor oil; paraffin mineral oil; an ethoxylated and/or propoxylated alcohol; or a polyalkyleneoxide modified with heptamethyltrisiloxane.

In some aspects, the present invention is directed to a composition comprising a synergistic fungicidal combination of a lipopeptide and an anionic surfactant. In certain aspects, the anionic surfactant is a polyalkylene compound. The polyalkylene compound can be selected from the group consisting of HORDAPHOS® 1306, GENAPOL® LRO, SILWET® L-77, SPAN® 20 and/or TWEEN® 20, MULTITROPE® 1214, SYNPERONIC® PE-L64 (ethoxylated/propoxylated alcohol), NIMBUS® (paraffinic mineral oil), MERO® (rapeseed methyl ester), and combinations thereof.

In other aspects, the present invention provides a composition comprising a synergistic fungicidal combination of a lipopeptide and a zwitterionic surfactant selected from the group consisting of cocamidopropyl betaine (C8-C18), C12-C14 lauryl dimethyl betaine, and coco betaine.

In other embodiments, the present invention is directed to a method of treating a plant to control a fungal disease and/or a bacterial disease, wherein the method comprises applying to the plant, to a part of the plant and/or to a locus of the plant a composition comprising an anionic surfactant or a salt thereof. In certain aspects, the anionic surfactant is a polyalkylene compound. The polyalkylene compound can be selected from the group consisting of HORDAPHOS® 1306, GENAPOL® LRO, SYNPERONIC® PE-L64, SILWET® L-77, SPAN® 20 and/or TWEEN® 20, MULTITROPE® 1214, NIMBUS®, MERO®, and combinations thereof.

Also provided is a method of treating a plant to control a fungal disease and/or a bacterial disease, wherein the method comprises applying to the plant, to a part of the plant and/or to a locus of the plant a composition comprising a zwitterionic surfactant. The zwitterionic surfactant may be a betaine with a quaternary ammonium. In some embodiments, the betaine is selected from the group consisting of cocamidopropyl betaine (C8-C18), C12-C14 lauryl dimethyl betaine, and coco betaine.

In yet other embodiments, the anionic surfactant is a compound of formula (I):

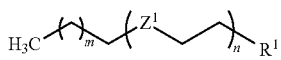
(I)

or a salt thereof, wherein
m is an integer between 0 and 18;
n is an integer between 1 and 10;
$Z^1$ is $CH_2$, S, O, or NH;
and $R^1$ is a sulfate, sulfonate, phosphate, or carboxylate.
In one aspect, $R^1$ is a sulfate. In another aspect, $Z^1$ is O. In one embodiment, n is an integer between 1 and 5. In another embodiment, m is an integer between 8 and 16. In some aspects, the composition comprises a compound selected from the group consisting of sodium lauryl ether sulfate (SLES), 3,6-dioxaeicosylsulfate, 3,6-dioxaoctadecylsulfate, a salt thereof, and combinations thereof.

In certain aspects, the lipopeptide component of the above-referenced compositions includes one or more of the following: iturin, bacillomycin, mycosubtilin, esperin, lichenysin, pumilacidin, surfactin, fengycin A, fengycin B, plipastatin A, plipastatin B, and/or agrastatin. In one instance of the aforementioned embodiment, the lipopeptide component includes one or more of the following: iturin, surfactin, fengycin and/or plipastatin. In another instance of the aforementioned embodiment, surfactin is excluded from the composition.

Lipopeptides include but are not limited to amphiphilic cyclic peptides obtainable from various bacteria, including *Bacillus* sp., *Paenibacillus* sp., and *Streptomyces* sp.

Amphiphilic cyclic lipopeptides are composed of six to ten α-amino acids linked to a β-amino or β-hydroxy fatty acid, including but not limited to fengycin-type compounds, iturin-type compounds, surfactin-type compounds and fusaricidins. The iturin-type compounds are composed of seven amino acids and are linked to a β-amino fatty acid. The length of the fatty acid chain may vary from C14 to C17. These compounds are obtainable from various species of *Bacillus*, including *subtilis* and *amyloliquefaciens*. The iturins and their variants are described in Ongena, et al., "*Bacillus* Lipopeptides: Versatile Weapons for Plant Disease Biocontrol," *Trends in Microbiology*, 16(3):115-125, (2007). Iturin-type compounds of the present invention include one or more of the following compounds: bacillomycin D, bacillyomycin F, bacillomycin L, bacillomycin LC (also known as bacillopeptin), mycosubtilin, iturin A, iturin $A_L$, and iturin C (with the latter three compounds referred to herein, collectively, as iturins).

Fengycin-type compounds are composed of ten amino acids linked to a β-hydroxy fatty acid with a chain that varies in length from C14 to C18. These compounds are obtainable from various species of *Bacillus*, including *subtilis*, *amyloliquefaciens*, *cereus* and *thuringiensis* and from *Streptomyces* sp. The fengycin-type compounds are described in Ongena, supra. Fengycin-type compounds suitable for the compositions described herein include fengycin A, fengycin B, plipastatin A, plipastatin B, the plipastatins from a *Streptomyces* sp. described in Kimura, et al., "SNA 60-367—New Peptide Enzyme Inhibitors Against Aromatase," *Journal of Antibiotics*, 50(6): 529-531, (1997), and agrastatins, as described in U.S. Pat. No. 6,291,426 (with the latter four listings referred to herein, collectively, as plipastatins).

Surfactin-type compounds are composed of seven amino acids linked to a β-hydroxy fatty acid with a chain that varies in length from C13 to C16. These compounds are obtainable from various species of *Bacillus*, including *subtilis*, *amyloliquefaciens*, *coagulans*, *pumilus* and *licheniformis*. The surfactin family of compounds is described in Ongena, supra. Surfactin-type compounds of the present invention include one or more of the following compounds: esperin, lichenysin, pumilacidin and surfactin.

Fusaricidins are composed of six amino acids linked to a 15-guanidino-3-hydroxypentadecanoic acid. Fusaricidins are obtainable from *Paenibacillus* sp., including *polymyxa*. The fusaricidin family of compounds is described in Choi, S-K, et al., "Identification and Functional Analysis of the Fusaricidin Biosynthetic Gene of *Paenibacillus polymyxa* E681," *Biochemical and Biophysical Research Communications*, 365:89-95, (2008). Fusaricidins of the present invention include one or more of the following compounds: fusaricidins A-D and fusaricidins LI-F03, LI-F04, LI-F05, LI-F06, LI-F07 and LI-F08.

Certain bacteria produce one or more lipopeptides, and combinations of various lipopeptides are known to have synergistic fungicidal activity. The lipopeptide component of the composition may comprise a combination of lipopeptides from at least two of the following lipopeptide classes: surfactin-type compounds, iturin-type compounds, and fengycin-type compounds. The combination may comprise two or more of the following compounds: iturin A, plipastatins A and B, fengycins A and B and surfactin. The combination may comprise one or more of the following compounds: iturin A, plipastatins A and B, fengycins A and B, surfactin and agrastatin.

In certain aspects, the compound of the present invention may be combined with or applied together with a depsipeptide. As used herein, a "depsipeptide" is a peptide in which one or more of the amide bonds are replaced by ester bonds. In certain embodiments, the depsipeptide is a cyclic depsipeptide. Non-limiting examples of depsipeptides that may be used with the present invention include fusaricidins A-D and fusaricidins LI-F03, LI-F04, LI-F05, LI-F06, LI-F07 and LI-F08.

Lipopeptides and depsipeptides of the present invention are produced by one or more bacteria, including but not limited to those described above, or are chemically synthesized. Methods of culturing bacteria are well known in the art. Conventional large-scale microbial culture processes include submerged fermentation, solid state fermentation, or liquid surface culture. For *Bacillus*, towards the end of fermentation, as nutrients are depleted, cells begin the transition from growth phase to sporulation phase, such that the final product of fermentation is largely spores, metabolites and residual fermentation medium. Sporulation is part of the natural life cycle of many Bacilli and is generally initiated by the cell in response to nutrient limitation. For this invention, fermentation is configured to obtain high levels of lipopeptides and to promote sporulation.

The bacterial cells, spores and metabolites in culture media resulting from fermentation (i.e., fermentation broth) may be used directly or concentrated (to make a fermentation solid) by conventional industrial methods, including but not limited to centrifugation, tangential-flow filtration, depth filtration, and evaporation. The concentrated fermentation solid is washed, for example, via a diafiltration process, to remove residual fermentation broth and metabolites.

The fermentation broth or fermentation solids can be dried with or without the addition of carriers using conventional drying processes or methods including but not limited to spray drying, freeze drying, tray drying, fluidized-bed drying, drum drying, or evaporation. The resulting dry fermentation solids may be further processed, including but not limited to by milling or granulation, to achieve a specific particle size or physical format. Carriers may also be added post-drying, as appropriate for the desired method of use.

Bacterially produced lipopeptides may be separated from bacterial cells or further purified from other bacterial components and, from each other. The term "cell-free preparation" refers to fermentation broth from which cells have been removed or substantially removed through means well known to those of skill in the art. Cell-free preparations of fermentation broth can be obtained by any means known in the art, including but not limited to extraction, centrifugation and/or filtration of fermentation broth. Those of skill in the art will appreciate that so-called cell-free preparations may not be devoid of cells but rather are largely cell-free or substantially cell-free, depending on the technique used (e.g., speed of centrifugation) to remove the cells. The resulting cell-free preparation may be dried and/or formulated with components that aid in its particular application. Concentration methods and drying techniques described above for fermentation broth are also applicable to cell-free preparations.

After a cell-free preparation is made by centrifugation of fermentation broth, the metabolites may be purified by size exclusion filtration including but not limited to the SEPHADEX® resins including LH-20, G10, and G15 and G25 that group metabolites into different fractions based on molecular weight cut-off, including but not limited to molecular weight of less than about 2000 daltons, less than about 1500 daltons, less than about 1000 daltons and so on, as the lipopeptides are between 800 daltons and 1600 daltons.

Lipopeptides of the present invention may be obtained from or are present in lipopeptide-producing fermentation products of *Bacillus subtilis*. In some embodiments, *Bacillus subtilis* QST713 or a fermentation product of *Bacillus subtilis* QST713 is used as the lipopeptide-producing component of the composition. *Bacillus subtilis* QST713, its mutants, its supernatants, and its lipopeptide metabolites, and methods for their use to control plant pathogens and insects are fully described in U.S. Pat. Nos. 6,060,051; 6,103,228; 6,291,426; 6,417,163 and 6,638,910. In these patents, the strain is referred to as AQ713, which is synonymous with QST713. *Bacillus subtilis* strain QST713 has been deposited with the NRRL on 7 May 1997, under the provisions of the Budapest Treaty on the International Recognition of the Deposit of Microorganisms for the Purpose of Patent Procedure under Accession Number B-21661. NRRL is the abbreviation for the Agricultural Research Service Culture Collection, an international depositary authority for the purposes of deposing microorganism strains under the Budapest Treaty on the International Recognition of the Deposit of Microorganisms for the Purposes of Patent Procedure, having the address National Center for Agricultural Utilization Research, Agricultural Research Service, U.S. Department of Agriculture, 1815 North University Street, Peoria, Ill. 61604, U.S.A. Any references in this specification to QST713 refer to *Bacillus subtilis* QST713. Particular variants of *Bacillus subtilis* QST713 (e.g., *Bacillus subtilis* AQ30002 and AQ30004, deposited as Accession Numbers NRRL B-50421 and NRRL B-50455) that would also be suitable for the present invention are described in U.S. Patent Publication No. 2012/0231951.

Any references in this specification to QST713 refer to *Bacillus subtilis* QST713 (aka AQ713) as present in the SERENADE® products, deposited under NRRL Accession No. B-21661, or prepared in bioreactors under conditions that simulate production of the SERENADE® product.

The microorganisms and particular strains described herein, unless specifically noted otherwise, are all separated from nature (i.e., isolated) and grown under artificial conditions such as in shake flask cultures or through scaled-up manufacturing processes, such as in bioreactors to maximize bioactive metabolite production, for example.

In certain aspects of the invention, a mutant strain of *Bacillus subtilis* QST713 is provided. The term "mutant" refers to a genetic variant derived from *Bacillus subtilis* QST713. In one embodiment, the mutant has one or more or all the identifying (functional) characteristics of *Bacillus subtilis* QST713. In a particular instance, the mutant or a fermentation product thereof controls (as an identifying functional characteristic) fungi, Oomycetes and/or bacteria at least as well as the parent *Bacillus subtilis* QST713. Such mutants may be genetic variants having a genomic sequence that has greater than about 85%, greater than about 90%, greater than about 95%, greater than about 98%, or greater than about 99% sequence identity to *Bacillus subtilis* QST713. Mutants may be obtained by treating *Bacillus subtilis* QST713 cells with chemicals or irradiation or by selecting spontaneous mutants from a population of *Bacillus subtilis* QST713 cells (such as phage resistant or antibiotic resistant mutants) or by other means well known to those practiced in the art.

The mutant strain can be any mutant strain that has one or more or all the identifying characteristics of *Bacillus subtilis* QST713 and in particular fungicidal activity that is comparable or better than that of *Bacillus subtilis* QST713.

At the time of filing U.S. patent application Ser. No. 09/074,870, in 1998, which corresponds to the above patents, the strain was designated as *Bacillus subtilis* based on classical, physiological, biochemical and morphological methods. Taxonomy of the *Bacillus* species has evolved since then, especially in light of advances in genetics and sequencing technologies, such that species designation is based largely on DNA sequence rather than the methods used in 1998. After aligning protein sequences from *B. amyloliquefaciens* FZB42, *B. subtilis* 168 and QST713, approximately 95% of proteins found in *B. amyloliquefaciens* FZB42 are 85% or greater identical to proteins found in QST713; whereas only 35% of proteins in *B. subtilis* 168 are 85% or greater identical to proteins in QST713. However, even with the greater reliance on genetics, there is still taxonomic ambiguity in the relevant scientific literature and regulatory documents, reflecting the evolving understanding of *Bacillus* taxonomy over the past 15 years. For example, a pesticidal product based on *B. subtilis* strain FZB24, which is as closely related to QST713 as FZB42, is classified in documents of the U.S. EPA as *B. subtilis* var. *amyloliquefaciens*. Due to these complexities in nomenclature, this particular *Bacillus* species is variously designated, depending on the document, as *B. subtilis*, *B. amyloliquefaciens*, and *B. subtilis* var. *amyloliquefaciens*. Therefore, we have retained the *B. subtilis* designation of QST713 rather than changing it to *B. amyloliquefaciens*, as would be expected currently based solely on sequence comparison and inferred taxonomy.

Suitable formulations of the *Bacillus subtilis* strain QST713 are commercially available under the trade names SERENADE®, SERENADE® ASO, SERENADE SOIL® and SERENADE® MAX from Bayer CropScience LP, North Carolina, U.S.A.

The SERENADE® product (U.S. EPA Registration No. 69592-12) contains a patented strain of Bacillus subtilis (strain QST713) and many different lipopeptides that work synergistically to destroy disease pathogens and provide superior antimicrobial activity. The SERENADE® product is used to protect plants such as vegetables, fruit, nut and vine crops against diseases such as Fire Blight, Botrytis, Sour Rot, Rust, Sclerotinia, Powdery Mildew, Bacterial Spot and White Mold. The SERENADE® products are available as either liquid or dry formulations which can be applied as a foliar and/or soil treatment. Copies of U.S. EPA Master Labels for the SERENADE® products, including SERENADE® ASO, SERENADE® MAX, and SERENADE SOIL®, are publicly available through National Pesticide Information Retrieval System's (NPIRS®) US EPA/OPP Pesticide Product Label System (PPLS).

SERENADE® ASO (Aqueous Suspension-Organic) contains 1.34% of dried QST713 as an active ingredient and 98.66% of other ingredients. SERENADE® ASO is formulated to contain a minimum of $1\times10^9$ cfu/g of QST713 while the maximum amount of QST713 has been determined to be $3.3\times10^{10}$ cfu/g. Alternate commercial names for SERENADE® ASO include SERENADE® BIOFUNGICIDE, SERENADE SOIL® and SERENADE® GARDEN DISEASE. For further information, see the U.S. EPA Master Labels for SERENADE® ASO dated Jan. 4, 2010, and SERENADE SOIL®, each of which is incorporated by reference herein in its entirety.

SERENADE® MAX contains 14.6% of dried QST713 as an active ingredient and 85.4% of other ingredients. SERENADE® MAX is formulated to contain a minimum of $7.3\times10^9$ cfu/g of QST713 while the maximum amount of QST713 has been determined to be $7.9\times10^{10}$ cfu/g. For further information, see the U.S. EPA Master Label for SERENADE® MAX, which is incorporated by reference herein in its entirety.

Other Bacillus strains capable of producing lipopeptides may be used as a source of lipopeptides for the present invention. For example, Bacillus amyloliquefaciens strain D747 (available as BACSTAR® from Etec Crop Solutions, NZ and also available as DOUBLE NICKEL55™ from Certis, US); Bacillus subtilis MBI600 (available as SUBTILEX® from Becker Underwood, US EPA Reg. No. 71840-8); Bacillus subtilis Y1336 (available as BIOBAC® WP from Bion-Tech, Taiwan, registered as a biological fungicide in Taiwan under Registration Nos. 4764, 5454, 5096 and 5277); Bacillus amyloliquefaciens, in particular strain FZB42 (available as RHIZOVITAL® from ABiTEP, DE); Bacillus subtilis var. amyloliquefaciens FZB24 is available from Novozymes Biologicals Inc. (Salem, Va.) or Syngenta Crop Protection, LLC (Greensboro, N.C.) as the fungicide TAEGRO® or TAEGRO® ECO (EPA Registration No. 70127-5), and Bacillus subtilis EA-CB0015 and Bacillus amyloliquefaciens EA-CB0959 (described in International Publication No. WO/2014/178032) are all Bacillus strains capable of producing lipopeptides that may be used as a source of lipopeptides for the present invention.

A mutant of FZB24 that was assigned Accession No. NRRL B-50349 by the Agricultural Research Service Culture Collection is also described in U.S. Patent Publication No. 2011/0230345. Bacillus amyloliquefaciens FZB42 is available from ABiTEP GMBH, Germany, as the plant strengthening product RHIZOVITAL®; FZB42 is also described in European Patent Publication No. EP2179652 and also in Chen, et al., "Comparative Analysis of the Complete Genome Sequence of the Plant Growth-Promoting Bacterium Bacillus amyloliquefaciens FZB42," Nature Biotechnology, Volume 25, Number 9 (September 2007). Mutants of FZB42 are described in International Publication No. WO 2012/130221, including Bacillus amyloliquefaciens ABI01, which was assigned Accession No. DSM 10-1092 by the DSMZ—German Collection of Microorganisms and Cell Cultures.

As described above, fermentation broth or extracts from fermentation broth may be used as the lipopeptide-producing component of the synergistic fungicidal combination of the present invention. Obtaining lipopeptides from fermentation broth of Bacillus bacteria, in general, and analyzing fermentation broths for presence of lipopeptides is well known to those of skill in the art, such that other bacterial strains suitable for the present invention could be readily identified by the skilled artisan. Bacillus strains that produce various lipopeptides are described in Ongena, Trends in Microbiology (2007) Vol. 16, No. 3. Other articles describe lipopeptide-producing Bacillus strains and methods for extracting lipopeptides from fermentation broths of such strains: see, e.g., Alvarez, et al., Journal of Applied Microbiology (2011) 112: 159-174; Ongena, et al., Applied Microbiology.

In certain embodiments, the synergistic fungicidal combination comprises a lipopeptide and a $C_8$-$C_{20}$-alkyl polyglycol ether sulfate such as sodium $C_{12}/C_{14}$-fatty alcohol diglycol ether sulfate (trade name GENAPOL® LRO, Clariant GmbH). In certain aspects, synergistic fungicidal combination comprises a lipopeptide and a $C_8$-$C_{20}$-alkyl polyglycol ether sulfate, a $C_{10}$-$C_{18}$-alkyl polyglycol ether sulfate, a salt thereof, for example, alkali metal salts such as sodium salts or potassium salts, and/or ammonium salts, but also alkaline earth metal salts such as magnesium salts. In some embodiments, the alkyl polyglycol ether sulfate has 2 to 5 ethylene oxide units present in the polyglycol moiety. In one embodiment, the alkyl polyglycol ether sulfate is sodium $C_{12}/C_{14}$-fatty alcohol diglycol ether sulfate (trade name GENAPOL® LRO, Clariant GmbH).

The weight to weight ratio of the compound and the lipopeptide (or, alternatively, the lipopeptide component (e.g., a lipopeptide-producing fermentation broth, a crude extract containing lipopeptides; a purified or semi-purified lipopeptide extract; or chemically synthesized or derivatized pure lipopeptide(s)) is in the range of about 1000:1 to about 1:1000, preferably in the range of about 500:1 to about 1:500, more preferably in the range of about 100:1 to about 1:100. Other preferred ratios are between about 20:1 and about 1:20, between about 10:1 and about 1:10, between about 5:1 and about 1:5, and between about 3:1 and about 1:3.

A ratio of about 100:1 means about 100 weight parts of compound (e.g., alkyl ether sulfate) and about 1 weight part of the lipopeptide or lipopeptide component such as the Bacillus subtilis QST713 fermentation product are combined (either as a solo formulation, a combined formulation or by separate applications to plants so that the combination is formed on the plant).

In one embodiment, the weight ratio of compound of the present invention to pure lipopeptides comprised of one or more compounds from one or more of the following families of compounds, surfactin-type compounds, iturin-type compounds, fengycin-type compounds, and/or fusaricidins is in the range of about 1000:1 to about 1:1000, preferably in the range of about 500:1 to about 1:500, more preferably in the range of about 100:1 to about 1:100, in the range of about 50:1 to about 1:50, or in the range of about 25:1 to about 1:25. In some embodiments, the weight to weight ratio of any of the above-described combinations of the compound and the lipopeptide or lipopeptide component is about 100:1 to about 1:100; in others it is about 10:1 to about 1:10; in still others it is about 5:1 to about 1:5; in yet others it is about 3:1 to about 1:3; and in yet others it is about 1:1.

In another embodiment, the weight ratio of compound(s) of the present invention to lipopeptide-producing fermentation broth (e.g., *Bacillus subtilis* QST713 fermentation broth) is in the range of about 500:1 to about 1:500, more preferably in the range of about 100:1 to about 1:100, in the range of about 50:1 to about 1:50, or in the range of about 25:1 to about 1:25. In one aspect, the weight ratio of compound(s) of the present invention to lipopeptide-producing fermentation broth is in the range of 24:1 to 3:1 as shown in Example 2 where 3000 ppm GENAPOL® LRO (sodium $C_{12}/C_{14}$-fatty alcohol diglycol ether sulfate) was combined with between 1000 ppm and 125 ppm of the SERENADE® ASO fermentation broth containing (1.67%) dried *Bacillus subtilis* QST713.

The compound (e.g., alkyl ether sulfate) and the lipopeptide or lipopeptide component are used or employed in a synergistic weight ratio. The skilled person understands that these ratios refer to the ratio within a combined-formulation as well as to the calculative ratio of the compound (e.g., alkyl ether sulfate) described herein and the lipopeptide or lipopeptide component when both components are applied as mono-formulations to a plant to be treated. The skilled person can calculate this ratio by simple mathematics since the volume and the amount of the compound (e.g., alkyl ether sulfate) and the lipopeptide or lipopeptide component, respectively, in a mono-formulation is known to the skilled person.

The ratio can be calculated based on the amount of the compound (e.g., alkyl ether sulfate), at the time point of applying said component of a combination according to the invention to a plant or plant part and the amount of and the lipopeptide or lipopeptide component shortly prior (e.g., 48 h, 24 h, 12 h, 6 h, 2 h, 1 h) or at the time point of applying said component of a combination according to the invention to a plant or plant part. The application of the compound (e.g., alkyl ether sulfate) and the lipopeptide or lipopeptide component to a plant or a plant part can take place simultaneously or at different times as long as both components are present on or in the plant after the application(s).

In some aspects, the compound (e.g., alkyl ether sulfate) and the lipopeptide or lipopeptide component are heated for about 1 hr, 2 hr, or 3 hr after being combined or mixed together. The mixture or combination may be heated to about 40° C., about 50° C., about 60° C., about 70° C., about 80° C., about 90° C., or about 100° C.

In one embodiment, the synergistic fungicidal combination comprises a lipopeptide and an agriculturally acceptable detergent. The detergent may be any detergent known in the art for use in agricultural formulations having the purpose, for example, of causing the formulation to stick to the surface of the target plant. It is to be appreciated that preferred detergents are completely biodegradable and environmentally friendly.

Compositions of the present invention may include carriers, which are inert formulation ingredients added to compositions comprising a lipopeptide-producing fermentation product, cell-free preparations of lipopeptides or purified, semi-purified or crude extracts of lipopeptides to improve recovery, efficacy, or physical properties and/or to aid in packaging and administration. Such carriers may be added individually or in combination.

The compositions of the present invention may be used for various purposes, including protection of crops and of post-harvest fruits, vegetables and plants; as preservatives for cosmetics, processed foods, animal feed, or timber; and for pharmaceutical and veterinary applications. Depending on the particular application, the compositions will be formulated with appropriate carriers to aid in their application or administration. The carriers may be anti-caking agents, anti-oxidation agents, bulking agents, and/or protectants. Examples of useful carriers include polysaccharides (starches, maltodextrins, methylcelluloses, proteins, including but not limited to whey protein, peptides, gums), sugars (lactose, trehalose, sucrose), lipids (lecithin, vegetable oils, mineral oils), salts (sodium chloride, calcium carbonate, sodium citrate), silicates (clays, amorphous silica, fumed/precipitated silicas, silicate salts), waxes, oils, alcohol and surfactants.

The compositions of the present invention further comprising a formulation inert or other formulation ingredient, including but not limited to polysaccharides, including but not limited to starches, maltodextrins, and methylcelluloses; proteins, including but not limited to whey protein, peptides, and gums; sugars, including but not limited to lactose, trehalose, and sucrose; lipids including but not limited to lecithin, vegetable oils, and mineral oils; salts including but not limited to sodium chloride, calcium carbonate, and sodium citrate; and silicates including but not limited to clays, amorphous silica, fumed/precipitated silicas, and silicate salts. The compositions of the present invention may also comprise a carrier, including but not limited to water or a mineral or organic material. The composition may be used for seed treatment or as a root dip, the carrier is a binder or sticker that facilitates adherence of the composition to the seed or root. The compositions can be used as a seed treatment the formulation ingredient is a colorant. In other compositions, the formulation may further comprise a preservative.

Compositions of the present invention may further comprise formulation inerts added to compositions comprising cells, cell-free preparations or metabolites to improve efficacy, stability, and usability and/or to facilitate processing, packaging and end-use application. Such formulation inerts and ingredients may include carriers, stabilization agents, nutrients, or physical property modifying agents, which may be added individually or in combination. The carriers may include liquid materials including but not limited to water, oil, and other solvents and solid materials including but not limited to minerals, polymers, or polymer complexes derived biologically or by chemical synthesis. The carrier is a binder or adhesive that facilitates adherence of the composition to a plant part, including but not limited to a seed or root. See, for example, Taylor, et al., "Concepts and Technologies of Selected Seed Treatments," Annu. Rev. Phytopathol., 28: 321-339 (1990). The stabilization agents include but are not limited to anti-caking agents, anti-oxidation agents, desiccants, protectants or preservatives. The nutrients may be carbon, nitrogen, and phosphors sources including but not limited to sugars, polysaccharides, oil, proteins, amino acids, fatty acids and phosphates. The physical property modifiers may be bulking agents, wetting agents, thickeners, pH modifiers, rheology modifiers, dispersants, adjuvants, surfactants, antifreeze agents, or colorants.

The composition as described herein may additionally comprising at least one auxiliary including but not limited to extenders, solvents, spontaneity promoters, carriers, emulsifiers, dispersants, frost protectants, thickeners and adjuvants. Those compositions may be referred to as formulations.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by CropLife International and in "Pesticide Specifications, Manual on Development and Use of FAO" and "WHO Specifications for Pesticides," "FAO Plant Production and Protection Papers"—173, prepared by the FAO/WHO Joint Meeting on Pesticide Specifications, 2004, ISBN: 9251048576. The formulations may comprise active agrochemical compounds other than one or more active compounds of the invention.

The formulations or application forms may comprise auxiliaries, including but not limited to extenders, solvents, spontaneity promoters, carriers, emulsifiers, dispersants, frost protectants, biocides, thickeners and/or other auxiliaries, including but not limited to adjuvants, for example. An adjuvant in this context is a component which enhances the biological effect of the formulation, without the component itself having a biological effect. Examples of adjuvants are agents which promote the retention, spreading, attachment to the leaf surface, or penetration.

These formulations are produced in a known manner, for example by mixing the active compounds with auxiliaries including but not limited to, for example, extenders, solvents and/or solid carriers and/or further auxiliaries, including but not limited to surfactants. The formulations are prepared either in suitable plants or else before or during the application.

Suitable for use as auxiliaries are substances which are suitable for imparting to the formulation of the active compound or the application forms prepared from these formulations (including but not limited to, e.g., usable crop protection agents, including but not limited to spray liquors or seed dressings) particular properties including but not limited to certain physical, technical and/or biological properties.

Stabilizers, including but not limited to low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers including but not limited to carboxymethylcellulose, natural and synthetic polymers in powder, granule or latex form, including but not limited to gum arabic, polyvinyl alcohol, polyvinyl acetate, and also natural phospholipids, including but not limited to cephalins and lecithins, and synthetic phospholipids.

Further possible auxiliaries include mineral and vegetable oils. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Suitable retention promoters include all those substances which reduce the dynamic surface tension, including but not limited to dioctyl sulphosuccinate, or increase the viscoelasticity, including but not limited to hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur, et al., 1997, Pesticide Science, 51, 131-152). Examples include alcohol alkoxylates including but not limited to coconut fatty ethoxylate (10) or isotridecyl ethoxylate (12), fatty acid esters including but not limited to rapeseed or soybean oil methyl esters, fatty amine alkoxylates including but not limited to tallowamine ethoxylate (15), or ammonium and/or phosphonium salts including but not limited to ammonium sulphate or diammonium hydrogen phosphate, for example.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1. Formula for the Efficacy of the Combination of Two Compounds

The advanced fungicidal activity of the active compound combinations according to the invention is evident from the example below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually. The expected activity for a given combination of two active compounds can be calculated as follows (cf. Colby, S. R., "Calculating Synergistic and Antagonistic Responses of Herbicide Combinations," Weeds, 1967, 15, 20-22):

If
X is the efficacy when active compound A is applied at an application rate of m ppm (or g/ha),
Y is the efficacy when active compound B is applied at an application rate of n ppm (or g/ha),
E is the efficacy when the active compounds A and B are applied at application rates of m and n ppm (or g/ha), respectively,
then $$E = X + Y - \frac{X \cdot Y}{100}.$$

The degree of efficacy, expressed in % is denoted. 0% means an efficacy which corresponds to that of the control while an efficacy of 100% means that no disease is observed.

If the actual fungicidal activity exceeds the calculated value, then the activity of the combination is super additive, i.e., a synergistic effect exists. In this case, the efficacy which was actually observed must be greater than the value for the expected efficacy (E) calculated from the above-mentioned formula.

A further way of demonstrating a synergistic effect is the method of Tammes (cf. "Isoboles, A Graphic Representation of Synergism in Pesticides," *Neth. J. Plant Path.,* 1964, 70, 73-80).

An additional method to identify synergistic interactions with antimicrobial agents is described by Scribner, et. al., (1982, Antimicrobial Agents and Chemotherapy 21(6):939-943) and in Goodman & Gilman (1980, The Pharmacological Basis of Therapeutics, Sixth Edition, pp. 1097-1098) and is referred to as the checkerboard assay. This assay involves serial two-fold dilutions of the antimicrobial agents individually and in combination, which are then inoculated with the microorganism(s) to be tested. After incubation, the minimum inhibitory concentration (MIC) of each antimicrobial agent used individually and in combination is determined. The MIC is the lowest concentration that inhibits growth of the microorganism. The MIC values are then used to calculate fractional inhibitory concentrations (i.e., $FIC_a$ and $FIC_b$), and the Fractional Inhibitory Concentration Index (FICI) is the sum of $FIC_a$ and $FIC_b$ as shown in the following equation:

$$FICI = FIC_a + FIC_b = \frac{MIC_a(\text{combination})}{MIC_a(\text{alone})} + \frac{MIC_b(\text{combination})}{MIC_b(\text{alone})}$$

A calculated FICI less than 1.0 suggests a synergistic interaction with an FICI less than or equal to 0.5 highly suggestive of synergy. See F. C. Odds, "Synergy, Antagonism, and What the Chequerboard Puts Between Them," *J. Antimicrob. Chemother.* 2003 52 (1), 1.

Example 2. Efficacy Against Plant Pathogens of an Alkyl Ether Sulfate Alone and in Combination with *Bacillus subtilis* QST713

The present study investigated the efficacy against a variety of plant pathogens of the commercial product, SERENADE® ASO (*Bacillus subtilis* QST713 fermentation product), with and without GENAPOL® LRO (sodium $C_{12}/C_{14}$-fatty alcohol diglycol ether sulfate). The application rates of SERENADE® ASO refer to the amount of (1.67%) *Bacillus subtilis* QST713 contained in the product SERENADE® ASO.

SERENADE® ASO was diluted in water to concentrations of 1000 ppm, 500 ppm, 250 ppm, and 125 ppm and applied to plants with or without GENAPOL® LRO applied at a concentration of 3000 ppm. Subsequently, the plants were inoculated with the various plant pathogens and scored for percent disease control with the following eight plant pathogen bioassays: (1) tomato late blight, *Phytophthora infestans* ("Late Blight"); (2) grape downy mildew, *Plasmopara viticola* ("Downy Mildew"); (3) cucumber powdery mildew, *Sphaerotheca fuliginea* ("Powdery Mildew"); (4) apple scab, *Venturia inaequalis* ("Scab"); (5) tomato early blight, *Alternaria solani* ("Early Blight"); (6) brown rust of snap bean, *Uromyces appendiculatus* ("Bean Rust"); (7) Asian soybean rust, *Phakopsora pachyrhizi* ("Soy Rust"); and (8) *Botrytis* grey mould on snap beans, *Botrytis cinerea* ("Grey Mould").

Results

The results of the eight plant pathogen assays are shown in Tables 2 through 6.

TABLE 2

Percent Disease Control Observed with Plants Treated with GENAPOL ® LRO, SERENADE ® ASO, or SERENADE ® ASO + GENAPOL ® LRO

| Plant Treatment | ppm | Late Blight | Downy Mildew | Powdery Mildew | Scab | Early Blight | Bean Rust | Soy Rust | Grey Mould |
|---|---|---|---|---|---|---|---|---|---|
| Uninfected (positive control) | 0 | 100 | 93 | 100 | 100 | 93 | 100 | 100 | 100 |
| H₂O (negative control) | 0 | 0 | 0 | 0 | 0 | 0 | 0 | 0 | 0 |
| GENAPOL ® LRO | 3000 | 0 | 59 | 20 | 84 | 0 | 40 | 30 | 23 |
| SERENADE ® ASO | 1000 | 0 | 24 | 37 | 28 | 92 | 70 | 73 | 53 |
|  | 500 | 0 | 0 | 30 | 11 | 68 | 70 | 70 | 35 |
|  | 250 | 0 | 0 | 0 | 11 | 24 | 50 | 15 | 0 |
|  | 125 | 0 | 0 | 0 | 0 | 16 | 30 | 8 | 0 |
| SERENADE ® ASO + GENAPOL ® LRO | 1000 | 68 | 76 | 30 | 93 | 91 | 75 | 73 | 95 |
|  | 500 | 15 | 65 | 30 | 87 | 81 | 70 | 75 | 88 |
|  | 250 | 23 | 78 | 30 | 83 | 24 | 40 | 40 | 60 |
|  | 125 | 0 | 91 | 30 | 72 | 16 | 60 | 15 | 50 |

TABLE 3

Comparison of Observed and Calculated Efficacies with Late Blight

| Active Compounds | Application Rate of Active Compound (ppm) | Efficacy in % Found* | Calc.** |
|---|---|---|---|
| GENAPOL ® LRO | 3000 | 0 | |
| SERENADE ® ASO | 1000 | 0 | |
| GENAPOL ® LRO + SERENADE ® ASO | 3000 + 1000 | 68 | 0 |

*Found = activity observed
**Calc. = activity calculated using Colby's formula

TABLE 4

Comparison of Observed and Calculated Efficacies with Downy Mildew

| Active Compounds | Application Rate of Active Compound (ppm) | Efficacy in % Found* | Calc.** |
|---|---|---|---|
| GENAPOL ® LRO | 3000 | 59 | |
| SERENADE ® ASO | 1000 | 24 | |
| GENAPOL ® LRO + SERENADE ® ASO | 3000 + 1000 | 76 | 69 |

*Found = activity observed
**Calc. = activity calculated using Colby's formula

TABLE 5

Comparison of Observed and Calculated Efficacies with Scab

| Active Compounds | Application Rate of Active Compound (ppm) | Efficacy in % Found* | Calc.** |
|---|---|---|---|
| GENAPOL ® LRO | 3000 | 84 | |
| SERENADE ® ASO | 1000 | 28 | |
| GENAPOL ® LRO + SERENADE ® ASO | 3000 + 1000 | 93 | 88 |

*Found = activity observed
**Calc. = activity calculated using Colby's formula

TABLE 6

Comparison of Observed and Calculated Efficacies with Grey Mould

| Active Compounds | Application Rate of Active Compound (ppm) | Efficacy in % Found* | Calc.** |
|---|---|---|---|
| GENAPOL ® LRO | 3000 | 23 | |
| SERENADE ® ASO | 1000 | 53 | |
| GENAPOL ® LRO + SERENADE ® ASO | 3000 + 1000 | 95 | 64 |

*Found = activity observed
**Calc. = activity calculated using Colby's formula

Conclusions

Application of both GENAPOL® LRO and SERENADE® ASO to the plants generally enhanced control of the plant pathogens over application of SERENADE® ASO alone. The combination of GENAPOL® LRO and SERENADE® ASO produced a synergistic effect when applied to plants infected with Late Blight, Downy Mildew, Scab, and Grey Mould.

Example 3. Efficacy of *Bacillus subtilis* QST713 Formulated with GENAPOL® LRO in a Field Trial with Tomatoes Infected with *Alternaria solani*

A whole broth culture (WB) of *Bacillus subtilis* QST713 was prepared by growing the strain in a soy-based medium. The WB was then mixed with 3% GENAPOL® LRO (sodium $C_{12}/C_{14}$-fatty alcohol diglycol ether sulfate) or 5% GENAPOL® LRO (sodium $C_{12}/C_{14}$-fatty alcohol diglycol ether sulfate) and allowed to equilibrate for at least 24 hours prior to use. The commercial product, SERENADE® ASO (*Bacillus subtilis* QST713) and the chemical fungicides ORTIVA® TOP (azoxystrobin and difenoconazole) and DITHANE® M 45 80 WP (mancozeb) were included for comparison.

The field trial was conducted with tomato plants that were artificially inoculated with a spore suspension of *Alternaria solani*. After inoculation, the tomato plants were treated beginning at growth stage BBCH 72 every 6-10 days as outlined in Table 8. The percent disease control shown in Table 7 is the average of 4 evaluations of disease severity on the mid leaves of the plants assessed throughout the course of the treatments with the last evaluation made 8 days after the final application.

TABLE 7

Average Disease Control in Tomato Plants Inoculated with *Alternaria solani*

| Treatment | Application Code | Disease Control [%] |
|---|---|---|
| Untreated, Non-Inoculated Control | — | 0 |
| SERENADE ® ASO (2 L/HA) | ABCDE | 35 |
| SERENADE ® ASO (4 L/HA) | ABCDE | 33 |
| QST713 WB + 5% GENAPOL ® LRO (1 L/HA) | ABCDE | 32 |
| QST713 WB + 5% GENAPOL ® LRO (2 L/HA) | ABCDE | 41 |
| QST713 WB + 3% GENAPOL ® LRO (1 L/HA) | ABCDE | 45 |
| QST713 WB + 3% GENAPOL ® LRO (2 L/HA) | ABCDE | 57 |
| ORTIVA ® TOP (azoxystrobin and difenoconazole) (1 L/HA) | ABCDE | 65 |
| DITHANE ® M 45 80 WP (mancozeb) (2000 G/HA) | ABCDE | 70 |

TABLE 8

Application Schedule for Treatments

| Application Code | Application Date | Growth Stage |
|---|---|---|
| A | December 26 | 72 |
| B | January 5 | 79 |
| C | January 13 | 79 |
| D | January 19 | 79 |
| E | January 26 | 79 |

The *Bacillus subtilis* QST713 WB mixed and equilibrated with GENAPOL® LRO (sodium $C_{12}/C_{14}$-fatty alcohol diglycol ether sulfate) generally demonstrated superior disease control at lower application rates than did the commercial product, SERENADE® ASO (*Bacillus subtilis* QST713).

Example 4. Efficacy of *Bacillus subtilis* QST713 Formulated with GENAPOL® LRO in a Field Trial with Apple Trees Infected with *Venturia inaequalis*

A field trial was conducted with apple trees that were naturally infected with the causal agent of scab, *Venturia inaequalis*. 10 treatments with an application volume of 1000 L/ha at 2 m cph were done between April 23 and June 30 at a growth stage of BBCH62 to BBCH77 in 5 to 11 days interval as outlined in Table 10. The percent disease control shown in Table 9 is the result of the last evaluation made 11 days after the final application, done by visual observation of disease symptoms. 0% means an efficacy which corresponds to that of the untreated control while an efficacy of 100% means that no disease was observed.

TABLE 9

Average Disease Control in Apple Trees Infected with *Venturia inaequalis*

| Product | Dosage | Application Code | Disease Control [%] Found* | Disease Control [%] Calc** |
|---|---|---|---|---|
| Untreated Control | | | 0 | |
| GENAPOL ® LRO | 0.3% | ABCDEFGHIJ | 11 | |
| SERENADE ® ASO | 12 l/ha | ABCDEFGHIJ | 27 | |
| SERENADE ® ASO | 8 L/ha | ABCDEFGHIJ | 31 | |
| SERENADE ® ASO + GENAPOL ® LRO | 12 L/ha + 0.3% | ABCDEFGHIJ | 75 | 35 |
| SERENADE ® ASO + GENAPOL ® LRO | 8 L/ha + 0.3% | ABCDEFGHIJ | 54 | 39 |

*found = activity found
**calc. = activity calculated using Colby's formula

TABLE 10

Application Schedule for Treatments

| Application Code | Application Date | Growth Stage |
|---|---|---|
| A | April 23 | 62 |
| B | April 28 | 63 |
| C | May 5 | 67 |
| D | May 12 | 71 |
| E | May 19 | 72 |
| F | May 26 | 73 |
| G | June 2 | 74 |
| H | June 11 | 75 |
| I | June 19 | 76 |
| J | June 30 | 77 |

The results in Table 9 clearly show that the observed activity of the combination of SERENADE® ASO and GENAPOL® LRO (sodium $C_{12}/C_{14}$-fatty alcohol diglycol ether sulfate) is greater than the calculated activity, i.e., a synergistic effect is present.

Example 5. Efficacy of *Bacillus subtilis* QST713 Formulated with GENAPOL® LRO in Field Trial with Bean Plants Infected with *Uromyces appendiculatus*

Two field trials were conducted with dry beans that were artificially inoculated with *Uromyces appendiculatus*. 5 treatments and 2 inoculations were done between July 1 and July 22 at a growth stage of BBCH29 to BBCH63 in 5 to 6 days interval as outlined in Table 12. The percent disease control shown in Table 11 is the result of the last evaluation made 20 days after the final application, done by visual observation of disease symptoms. 0% means an efficacy which corresponds to that of the untreated control while an efficacy of 100% means that no disease was observed.

TABLE 11

Average Disease Control in Bean Plants Infected with *Uromyces appendiculatus*

| Product | Dosage | Application Code | Disease Control [%] Mean of 2 Trials Found* | Disease Control [%] Calc** |
|---|---|---|---|---|
| Untreated Control | | | 0 | |
| GENAPOL ® LRO | 0.3% | ABCDE | 5 | |
| SERENADE ® ASO | 12 L/ha | ABCDE | 58 | |
| SERENADE ® ASO | 8 L/ha | ABCDE | 48 | |
| SERENADE ® ASO + GENAPOL ® LRO | 12 L/ha + 0.3% | ABCDE | 64 | 60 |
| SERENADE ® ASO + GENAPOL ® LRO | 8 L/ha + 0.3% | ABCDE | 61 | 51 |

*found = activity found
**calc. = activity calculated using Colby's formula

TABLE 12

Inoculation and Application Schedules for Field Trials

| Application Code | Application Date | Growth Stage |
|---|---|---|
| A | July 1 | 29 |
| Inoculation | July 2 | 29 |
| B | July 7 | 51 |
| Inoculation | July 7 | 51 |
| C | July 12 | 59 |
| D | July 17 | 61 |
| E | July 22 | 63 |

The results in Table 11 clearly show that the observed activity of the combination of SERENADE® ASO and GENAPOL® LRO (sodium $C_{12}/C_{14}$-fatty alcohol diglycol ether sulfate) is greater than the calculated activity, i.e., a synergistic effect is present.

Example 6. Efficacy Against Plant Pathogens of *Bacillus subtilis* QST713 in Combination with Different Adjuvants The present study investigated the efficacy against a variety of plant pathogens of the commercial product, SERENADE® ASO (*Bacillus subtilis* QST713 fermentation product), with and without one of several different adjuvants/surfactants listed in Table 13. These adjuvants/surfactants when applied in combination with SERENADE® ASO (*Bacillus subtilis* QST713 fermentation product) demonstrated synergistic effects against various plant pathogens while other adjuvants/surfactants did not.

TABLE 13

List of Adjuvants

| Adjuvant | Manufacturer | Chemical Composition |
| --- | --- | --- |
| GEROPON ® DOS/PG | Solvay/Rhodia | sodium-2-ethylhexylsulfosuccinate; sodium di-2-ethylhexyl sulphosuccinate; docusate sodium |
| SILWET ® L77 | Momentive | polyalkyleneoxide modified heptamethyltrisiloxane |
| AGNIQUE ® PG8107G | Cognis | C8-10 alkyl polyglycoside, oligomeric D-glucopyranose decyl octyl glycosides, alkylated polyglycoside |
| GENAPOL ® LRO | Clariant | alcohols, C12-14, ethoxylated, sulfates, sodium salts; sodium alkyl ether sulfate; sodium lauryl ether sulfate |
| SPAN ®20 + TWEEN ®20 (62.5:37.5) | Croda | sorbitan monolaurate/ethoxy (20) sorbitan monolaurate; POE-(20)-sorbitan monolaurate; sorbitan monododecanoate, poly(oxy-1,2-ethanediyl) derivatives |
| SYNPERONIC ® PE-L64 | Croda | non-ionic surfactant - ethoxylated/propoxylated alcohol |
| STICMAN ® | De Sangosse | synthetic latex |
| NIMBUS ® | Syngenta | emulsifiable crop oil (paraffin mineral oil-based) |
| SC-TankMix | Bayer | rapeseed oil methyl ester; castor oil ethoxylated |
| MERO ® | Bayer | rapeseed oil methyl ester EC 733 |

Example 7. In Vivo Preventive Test on *Phytophthora* (Tomatoes)

SERENADE® ASO (*Bacillus subtilis* QST713 fermentation product) and the adjuvant GENAPOL® LRO (sodium $C_{12}/C_{14}$-fatty alcohol diglycol ether sulfate) were diluted in water to the desired concentrations and applied separately and in combination to young tomato plants. After the spray coating had dried on, the plants were inoculated with an aqueous spore suspension of *Phytophthora infestans*. Subsequently the plants were placed in an incubation cabinet at approximately 20° C. and a relative atmospheric humidity of 100%. The test was evaluated 3 days after the inoculation. 0% means an efficacy which corresponds to that of the untreated control, while an efficacy of 100% means that no disease is observed. The table below (Table 14) clearly shows that the observed activity of SERENADE® ASO (*Bacillus subtilis* QST713 fermentation product) in combination with GENAPOL® LRO (sodium $C_{12}/C_{14}$-fatty alcohol diglycol ether sulfate) is greater than the calculated activity, i.e. a synergistic effect is present.

TABLE 14

In vivo Preventive Test on *Phytophthora* (Tomatoes)

| Active Compounds | Application Rate of Compound | Efficacy in % Found* | Calc.** |
| --- | --- | --- | --- |
| SERENADE ® ASO | 6% | 0 | |
| GENAPOL ® LRO | 0.3% | 0 | |
| SERENADE ® ASO + GENAPOL ® LRO | 6% + 0.3% | 68 | 0 |

*found = activity found
**calc. = activity calculated using Colby's formula

Example 8. In Vivo Preventive Test on *Plasmopara* (Grapevines)

SERENADE® ASO (*Bacillus subtilis* QST713 fermentation product) and the adjuvants GENAPOL® LRO (sodium $C_{12}/C_{14}$-fatty alcohol diglycol ether sulfate), SPAN®20+TWEEN®20 (sorbitan monolaurate; sorbitan monododecanoate) or STICMAN® (synthetic latex) were diluted in water to the desired concentrations and applied separately and in combination to young grape plants. After the spray coating had dried on, the plants were inoculated with an aqueous spore suspension of *Plasmopara viticola* and remained for 1 day in an incubation cabinet at approximately 20° C. and a relative atmospheric humidity of 100%. Subsequently the plants were placed for 4 days in a greenhouse at approximately 21° C. and a relative atmospheric humidity of approximately 90%. The plants were then misted and placed for 1 day in an incubation cabinet.

The test was evaluated 6 days after the inoculation. 0% means an efficacy which corresponds to that of the untreated control, while an efficacy of 100% means that no disease is observed. The table below (Table 15) clearly shows that the observed activity of SERENADE® ASO (*Bacillus subtilis* QST713 fermentation product) in combination with GENAPOL® LRO (sodium $C_{12}/C_{14}$-fatty alcohol diglycol ether sulfate), SPAN®20+TWEEN®20 (sorbitan monolaurate; sorbitan monododecanoate) or STICMAN® (synthetic latex) is greater than the calculated activity, i.e., a synergistic effect is present.

TABLE 15

In vivo Preventive Test on *Plasmopara* (Grapevines)

| Active Compounds | Application Rate of Compound | Efficacy in % Found* | Calc.** |
| --- | --- | --- | --- |
| SERENADE ® ASO | 6% | 24 | |
| | 3% | 0 | |
| | 1.5% | 0 | |
| | 0.75% | 0 | |
| GENAPOL ® LRO | 0.3% | 59 | |
| SPAN ®20 + TWEEN ®20 | 0.3% | 16 | |
| STICMAN ® | 0.3% | 0 | |
| SERENADE ® ASO + GENAPOL ® LRO | 1.5% + 0.3% | 78 | 59 |
| SERENADE ® ASO + GENAPOL ® LRO | 0.75% + 0.3% | 91 | 59 |
| SERENADE ® ASO + SPAN ®20 + TWEEN ®20 | 6% + 0.3% | 77 | 36 |
| SERENADE ® ASO + SPAN ®20 + TWEEN ®20 | 3% + 0.3% | 41 | 16 |
| SERENADE ® ASO + SPAN ®20 + TWEEN ®20 | 1.5% + 0.3% | 59 | 16 |

TABLE 15-continued

In vivo Preventive Test on *Plasmopara* (Grapevines)

| Active Compounds | Application Rate of Compound | Efficacy in % Found* | Calc.** |
|---|---|---|---|
| SERENADE ® ASO + SPAN ®20 + TWEEN ®20 | 0.75% + 0.3% | 51 | 16 |
| SERENADE ® ASO + STICMAN ® | 6% + 0.3% | 73 | 24 |

*found = activity found
**calc. = activity calculated using Colby's formula

Example 9. In Vivo Preventive Test on *Sphaerotheca* (Cucumbers)

SERENADE® ASO (*Bacillus subtilis* QST713 fermentation product) and the adjuvants SILWET® L-77 (polyalkyleneoxide modified heptamethyltrisiloxane), STICMAN® (synthetic latex), NIMBUS® (paraffin mineral oil), SC-TankMix (rapeseed oil methyl ester; castor oil ethoxylated) or MERO® (rapeseed oil methyl ester) were diluted in water to the desired concentrations and applied separately and in combination to young cucumber plants. After the spray coating had dried on, the plants were inoculated with an aqueous spore suspension of *Sphaerotheca fuliginea*. Subsequently the plants were placed in a greenhouse at approximately 23° C. and a relative atmospheric humidity of approximately 70%. The test was evaluated 7 days after the inoculation. 0% means an efficacy which corresponds to that of the untreated control, while an efficacy of 100% means that no disease is observed. The table below (Table 16) clearly shows that the observed activity of SERENADE® ASO (*Bacillus subtilis* QST713 fermentation product) in combination with SILWET® L-77 (polyalkyleneoxide modified heptamethyltrisiloxane), STICMAN® (synthetic latex), NIMBUS® (paraffin mineral oil), SC-TankMix (rapeseed oil methyl ester; castor oil ethoxylated) or MERO® (rapeseed oil methyl ester) is greater than the calculated activity, i.e., a synergistic effect is present.

TABLE 16

In vivo Preventive Test on *Sphaerotheca* (Cucumbers)

| Active Compounds | Application Rate of Compound | Efficacy in % Found* | Calc.** |
|---|---|---|---|
| SERENADE ® ASO | 6% | 37 | |
|  | 3% | 30 | |
|  | 1.5% | 0 | |
| SILWET ® L-77 | 0.05% | 0 | |
| STICMAN ® | 0.3% | 0 | |
| NIMBUS ® | 0.3% | 0 | |
| SC-TankMix | 0.2% | 0 | |
| MERO ® | 0.3% | 0 | |
| SERENADE ® ASO + SILWET ® L-77 | 6% + 0.05% | 57 | 37 |
| SERENADE ® ASO + STICMAN ® | 6% + 0.3% | 63 | 37 |
| SERENADE ® ASO + NIMBUS ® | 6% + 0.3% | 77 | 37 |
| SERENADE ® ASO + NIMBUS ® | 3% + 0.3% | 73 | 30 |
| SERENADE ® ASO + NIMBUS ® | 1.5% + 0.3% | 50 | 0 |
| SERENADE ® ASO + SC-TankMix | 6% + 0.2% | 82 | 37 |
| SERENADE ® ASO + SC-TankMix | 3% + 0.2% | 85 | 37 |
| SERENADE ® ASO + MERO ® | 6% + 0.3% | 95 | 37 |

*found = activity found
**calc. = activity calculated using Colby's formula

Example 10. In Vivo Preventive Test on *Venturia* (Apples)

SERENADE® ASO (*Bacillus subtilis* QST713 fermentation product) and the adjuvants SILWET® L-77 (polyalkyleneoxide modified heptamethyltrisiloxane), SPAN®20+TWEEN®20 (sorbitan monolaurate; sorbitan monododecanoate), NIMBUS® (paraffin mineral oil) or MERO® (rapeseed oil methyl ester) were diluted in water to the desired concentrations and applied separately and in combination to young apple tree plants. After the spray coating had dried on, the plants were inoculated with an aqueous conidia suspension of the causal agent of apple scab (*Venturia inaequalis*) and then kept for 1 day in an incubation cabinet at approximately 20° C. and a relative atmospheric humidity of 100%. Subsequently the plants were placed in a greenhouse at approximately 21° C. and a relative atmospheric humidity of approximately 90%. The test was evaluated 10 days after the inoculation. 0% means an efficacy which corresponds to that of the untreated control, while an efficacy of 100% means that no disease is observed. The table below (Table 17) clearly shows that the observed activity of SERENADE® ASO (*Bacillus subtilis* QST713 fermentation product) in combination with SILWET® L-77 (polyalkyleneoxide modified heptamethyltrisiloxane), SPAN®20+TWEEN®20 (sorbitan monolaurate; sorbitan monododecanoate), NIMBUS® (paraffin mineral oil) or MERO® (rapeseed oil methyl ester) is greater than the calculated activity, i.e., a synergistic effect is present.

TABLE 17

In vivo Preventive Test on *Venturia* (Apples)

| Active Compounds | Application Rate of Compound | Efficacy in % Found* | Calc.** |
|---|---|---|---|
| SERENADE ® ASO | 6% | 28 | |
|  | 3% | 11 | |
|  | 1.5% | 11 | |
|  | 0.75% | 0 | |
| SILWET ® L-77 | 0.05% | 0 | |
| SPAN ®20 + TWEEN ®20 | 0.3% | 23 | |
| NIMBUS ® | 0.3% | 0 | |
| MERO ® | 0.3% | 0 | |
| SERENADE ® ASO + SILWET ® L-77 | 6% + 0.05% | 63 | 28 |
| SERENADE ® ASO + SILWET ® L-77 | 3% + 0.05% | 69 | 28 |
| SERENADE ® ASO + SPAN ®20 + TWEEN ®20 | 6% + 0.3% | 91 | 45 |
| SERENADE ® ASO + SPAN ®20 + TWEEN ®20 | 3% + 0.3% | 78 | 31 |
| SERENADE ® ASO + SPAN ®20 + TWEEN ®20 | 1.5% + 0.3% | 79 | 31 |
| SERENADE ® ASO + SPAN ®20 + TWEEN ®20 | 0.75% + 0.3% | 67 | 23 |
| SERENADE ® ASO + NIMBUS ® | 6% + 0.3% | 77 | 28 |
| SERENADE ® ASO + NIMBUS ® | 3% + 0.3% | 78 | 11 |
| SERENADE ® ASO + NIMBUS ® | 1.5% + 0.3% | 77 | 11 |
| SERENADE ® ASO + NIMBUS ® | 0.75% + 0.3% | 61 | 0 |
| SERENADE ® ASO + MERO ® | 6% + 0.3% | 83 | 28 |
| SERENADE ® ASO + MERO ® | 3% + 0.3% | 71 | 11 |
| SERENADE ® ASO + MERO ® | 1.5% + 0.3% | 46 | 11 |
| SERENADE ® ASO + MERO ® | 0.75% + 0.3% | 51 | 0 |

*found = activity found
**calc. = activity calculated using Colby's formula

Example 11. In Vivo Preventive Test on *Alternaria* (Tomatoes)

SERENADE® ASO (*Bacillus subtilis* QST713 fermentation product) and the adjuvants GEROPON® DOS-PG (sodium-2-ethylhexylsulfosuccinate), SILWET® L-77 (polyalkyleneoxide modified heptamethyltrisiloxane), GENAPOL® LRO (sodium $C_{12}/C_{14}$-fatty alcohol diglycol ether sulfate), SYNPERONIC® PE-L64 (ethoxylated/propoxylated alcohol), NIMBUS® (paraffin mineral oil) or SC-TankMix (rapeseed oil methyl ester; castor oil ethoxylated) were diluted in water to the desired concentrations and applied separately and in combination to young tomato plants. After the spray coating had dried on, the plants were inoculated with an aqueous spore suspension of *Alternaria solani*. Subsequently the plants were placed in an incubation cabinet at approximately 20° C. and a relative atmospheric humidity of 100%. The test was evaluated 3 days after the inoculation. 0% means an efficacy which corresponds to that of the untreated control while an efficacy of 100% means that no disease is observed. The table below (Table 18) clearly shows that the observed activity of SERENADE® ASO in combination with GEROPON® DOS-PG (sodium-2-ethylhexylsulfosuccinate), SILWET® L-77 (polyalkyleneoxide modified heptamethyltrisiloxane), GENAPOL® LRO (sodium $C_{12}/C_{14}$-fatty alcohol diglycol ether sulfate), SYNPERONIC® PE-L64 (ethoxylated/propoxylated alcohol), NIMBUS® (paraffin mineral oil) or SC-TankMix (rapeseed oil methyl ester; castor oil ethoxylated) is greater than the calculated activity, i.e., a synergistic effect is present.

Example 12. In Vivo Preventive Test on *Phakopsora* (Soybeans)

SERENADE® ASO (*Bacillus subtilis* QST713 fermentation product) and the adjuvants GEROPON® DOS-PG (sodium-2-ethylhexylsulfosuccinate), SILWET® L-77 (polyalkyleneoxide modified heptamethyltrisiloxane), SYNPERONIC® PE-L64 (ethoxylated/propoxylated alcohol) or NIMBUS® (paraffin mineral oil) were diluted in water to the desired concentrations and applied separately and in combination to young soybean plants. After the spray coating had dried on, the plants were inoculated with an aqueous spore suspension of the causal agent of soybean rust (*Phakopsora pachyrhizi*) and were placed for 24 h without light in an incubation cabinet at approximately 24° C. and a relative atmospheric humidity of 95%. The plants remained in the incubation cabinet at approximately 24° C. and a relative atmospheric humidity of approximately 80% and a day/night interval of 12 h. The test was evaluated 7 days after the inoculation. 0% means an efficacy which corresponds to that of the untreated control, while an efficacy of 100% means that no disease is observed. The table below (Table 19) clearly shows that the observed activity of SERENADE® ASO (*Bacillus subtilis* QST713 fermentation product) in combination with GEROPON® DOS-PG (sodium-2-ethylhexylsulfosuccinate), SILWET® L-77 (polyalkyleneoxide modified heptamethyltrisiloxane), SYNPERONIC® PE-L64 (ethoxylated/propoxylated alcohol) or NIMBUS® (paraffin mineral oil) is greater than the calculated activity, i.e., a synergistic effect is present.

TABLE 18

In vivo Preventive Test on *Alternaria* (Tomatoes)

| Active Compounds | Application Rate of Compound | Efficacy in % Found* | Calc.** |
|---|---|---|---|
| SERENADE ® ASO | 3% | 68 | |
|  | 1.5% | 24 | |
| GEROPON ® DOS-PG | 0.05% | 35 | |
| SILWET ® L-77 | 0.05% | 16 | |
| GENAPOL ® LRO | 0.3% | 0 | |
| SYNPERONIC ® PE-L64 | 0.3% | 8 | |
| NIMBUS ® | 0.3% | 0 | |
| SC-TankMix | 0.2% | 0 | |
| SERENADE ® ASO + GEROPON ® DOS-PG | 1.5% + 0.05% | 65 | 51 |
| SERENADE ® ASO + SILWET ® L-77 | 1.5% + 0.05% | 70 | 36 |
| SERENADE ® ASO + GENAPOL ® LRO | 3% + 0.3% | 81 | 68 |
| SERENADE ® ASO + SYNPERONIC ® PE-L64 | 3% + 0.3% | 86 | 71 |
| SERENADE ® ASO + SYNPERONIC ® PE-L64 | 1.5% + 0.3% | 46 | 30 |
| SERENADE ® ASO + NIMBUS ® | 3% + 0.3% | 78 | 68 |
| SERENADE ® ASO + NIMBUS ® | 1.5% + 0.3% | 51 | 24 |
| SERENADE ® ASO + SC-TankMix | 3% + 0.2% | 81 | 68 |
| SERENADE ® ASO + SC-TankMix | 1.5% + 0.2% | 62 | 24 |

*found = activity found
**calc. = activity calculated using Colby's formula

TABLE 19

**In vivo Preventive Test on *Phakopsora* (Soybeans)**

| Active Compounds | Application Rate of Compound | Efficacy in % Found* | Calc.** |
|---|---|---|---|
| SERENADE ® ASO | 6% | 73 | |
|  | 3% | 70 | |
|  | 1.5% | 15 | |
|  | 0.75% | 8 | |
| GEROPON ® DOS-PG | 0.05% | 0 | |
| SILWET ® L-77 | 0.05% | 0 | |
| SYNPERONIC ® PE-L64 | 0.3% | 0 | |
| NIMBUS ® | 0.3% | 0 | |
| SERENADE ® ASO + GEROPON ® DOS-PG | 6% + 0.05% | 80 | 73 |
| SERENADE ® ASO + GEROPON ® DOS-PG | 6% + 0.05% | 80 | 70 |
| SERENADE ® ASO + GEROPON ® DOS-PG | 1.5% + 0.05% | 73 | 15 |
| SERENADE ® ASO + GEROPON ® DOS-PG | 0.75% + 0.05% | 55 | 8 |
| SERENADE ® ASO + SILWET ® L-77 | 1.5% + 0.05% | 53 | 15 |
| SERENADE ® ASO + SYNPERONIC ® PE-L64 | 1.5% + 0.3% | 63 | 15 |
| SERENADE ® ASO + NIMBUS ® | 6% + 0.3% | 83 | 73 |

*found = activity found
**calc. = activity calculated using Colby's formula

Example 13. In Vivo Preventive Test on *Uromyces* (Beans)

SERENADE® ASO (*Bacillus subtilis* QST713 fermentation product) and the adjuvants GEROPON® DOS-PG (sodium-2-ethylhexylsulfosuccinate), SILWET® L-77 (polyalkyleneoxide modified heptamethyltrisiloxane), SYNPERONIC® PE-L64 (ethoxylated/propoxylated alcohol), STICMAN® (synthetic latex), NIMBUS® (paraffin mineral oil) or MERO® (rapeseed oil methyl ester) were diluted in water to the desired concentrations and applied separately and in combination to young bean plants. After the spray coating had dried on, the plants were inoculated with an aqueous spore suspension of the causal agent of bean rust (*Uromyces appendiculatus*) and then remained for 1 day in an incubation cabinet at approximately 20° C. and a relative atmospheric humidity of 100%. Subsequently the plants were placed in a greenhouse at approximately 21° C. and a relative atmospheric humidity of approximately 90%. The test was evaluated 10 days after the inoculation. 0% means an efficacy which corresponds to that of the untreated control, while an efficacy of 100% means that no disease is observed. The table below (Table 20) clearly shows that the observed activity of SERENADE® ASO (*Bacillus subtilis* QST713 fermentation product) in combination with GEROPON® DOS-PG (sodium-2-ethylhexylsulfosuccinate), SILWET® L-77 (polyalkyleneoxide modified heptamethyltrisiloxane), SYNPERONIC® PE-L64 (ethoxylated/propoxylated alcohol), STICMAN® (synthetic latex), NIMBUS® (paraffin mineral oil) or MERO® (rapeseed oil methyl ester) is greater than the calculated activity, i.e., a synergistic effect is present.

TABLE 20

**In vivo Preventive Test on *Uromyces* (Beans)**

| Active Compounds | Application Rate of Compound | Efficacy in % Found* | Calc.** |
|---|---|---|---|
| SERENADE ® ASO | 6% | 70 | |
|  | 3% | 70 | |
|  | 1.5% | 50 | |
| GEROPON ® DOS-PG | 0.05% | 0 | |
| SILWET ® L-77 | 0.05% | 0 | |
| SYNPERONIC ® PE-L64 | 0.3% | 0 | |
| STICMAN ® | 0.3% | 0 | |
| NIMBUS ® | 0.3% | 0 | |
| MERO ® | 0.3% | 0 | |
| SERENADE ® ASO + GEROPON ® DOS-PG | 6% + 0.05% | 80 | 70 |
| SERENADE ® ASO + GEROPON ® DOS-PG | 3% + 0.05% | 75 | 70 |
| SERENADE ® ASO + GEROPON ® DOS-PG | 1.5% + 0.05% | 60 | 50 |
| SERENADE ® ASO + SILWET ® L-77 | 3% + 0.05% | 75 | 70 |
| SERENADE ® ASO + SILWET ® L-77PG | 1.5% + 0.05% | 70 | 50 |
| SERENADE ® ASO + SYNPERONIC ® PE-L64 | 6% + 0.3% | 93 | 70 |
| SERENADE ® ASO + STICMAN ® | 6% + 0.3% | 95 | 70 |

TABLE 20-continued

In vivo Preventive Test on *Uromyces* (Beans)

| Active Compounds | Application Rate of Compound | Efficacy in % Found* | Calc.** |
|---|---|---|---|
| SERENADE ® ASO + NIMBUS ® | 6% + 0.3% | 85 | 70 |
| SERENADE ® ASO + NIMBUS ® | 3% + 0.3% | 75 | 70 |
| SERENADE ® ASO + NIMBUS ® | 1.5% + 0.3% | 60 | 50 |
| SERENADE ® ASO + MERO ® | 6% + 0.3% | 85 | 70 |
| SERENADE ® ASO + MERO ® | 3% + 0.3% | 80 | 70 |

*found = activity found
**calc. = activity calculated using Colby's formula

Example 14. In Vivo Preventive Test on *Botrytis* (Beans)

SERENADE® ASO (*Bacillus subtilis* QST713 fermentation product) and the adjuvants AGNIQUE® PG8107G ($C_{8-10}$ alkyl polyglycoside), GENAPOL® LRO (sodium $C_{12}/C_{14}$-fatty alcohol diglycol ether sulfate), SC-TankMix (rapeseed oil methyl ester; castor oil ethoxylated) or MERO® (rapeseed oil methyl ester) were diluted in water to the desired concentrations and applied separately and in combination to young bean plants. After the spray coating had dried on, 2 small pieces of agar covered with growth of *Botrytis cinerea* were placed on each leaf. The inoculated plants were placed in a darkened chamber at 14° C. and a relative atmospheric humidity of 100%. 3 days after the inoculation, the size of the lesions on the leaves was evaluated. 0% means an efficacy which corresponds to that of the untreated control, while an efficacy of 100% means that no disease is observed. The table below (Table 21) clearly shows that the observed activity of SERENADE® ASO (*Bacillus subtilis* QST713 fermentation product) in combination with AGNIQUE® PG8107G ($C_{8-10}$ alkyl polyglycoside), GENAPOL® LRO (sodium $C_{12}/C_{14}$-fatty alcohol diglycol ether sulfate), SC-TankMix (rapeseed oil methyl ester; castor oil ethoxylated) or MERO® (rapeseed oil methyl ester) is greater than the calculated activity, i.e. a synergistic effect is present.

TABLE 21

In vivo Preventive Test on *Botrytis* (Beans)

| Active Compounds | Application Rate of Compound | Efficacy in % found* | calc.** |
|---|---|---|---|
| SERENADE ® ASO | 6% | 53 | |
| | 3% | 35 | |
| | 1.5% | 0 | |
| | 0.75% | 0 | |

TABLE 21-continued

In vivo Preventive Test on *Botrytis* (Beans)

| Active Compounds | Application Rate of Compound | Efficacy in % found* | calc.** |
|---|---|---|---|
| AGNIQUE ® PG8107G | 0.2% | 0 | |
| GENAPOL ® LRO | 0.3% | 23 | |
| SC-TankMix | 0.2% | 0 | |
| MERO ® | 0.3% | 26 | |
| SERENADE ® ASO + AGNIQUE ® PG8107G | 3% + 0.2% | 64 | 35 |
| SERENADE ® ASO + GENAPOL ® LRO | 6% + 0.3% | 95 | 64 |
| SERENADE ® ASO + GENAPOL ® LRO | 3% + 0.3% | 88 | 50 |
| SERENADE ® ASO + GENAPOL ® LRO | 1.5% + 0.3% | 60 | 23 |
| SERENADE ® ASO + GENAPOL ® LRO | 0.75% + 0.3% | 50 | 23 |
| SERENADE ® ASO + SC-TankMix | 3% + 0.2% | 55 | 35 |
| SERENADE ® ASO + MERO ® | 6% + 0.3% | 93 | 65 |

*found = activity found
**calc. = activity calculated using Colby's formula

Example 15. Screening to Identify Additional Surfactants that Increase Antifungal Activity of *Bacillus subtilis* QST713 Fermentation Product in SERENADE® ASO Additional surfactants were selected and identified for their enhancement of the antifungal activity of SERENADE® ASO (*Bacillus subtilis* QST713 fermentation product) as depicted in Table 22. These adjuvants/surfactants when applied in combination with SERENADE® ASO (*Bacillus subtilis* QST713 fermentation product) demonstrated synergistic effects against various plant pathogens while other adjuvants/surfactants did not.

TABLE 22

Selected Surfactants for Biological Screening

| Surfactant | Manufacturer | Chemical Composition |
|---|---|---|
| GENAGEN ® CAB 818 | Clariant | cocoamidopropyl betaine (C8-C18) 1-propanaminium, 3-amino-N-(carboxymethyl)-N,N-dimethyl-, N-coco acyl derivatives, hydroxides, inner salts |
| GENAGEN ® KB | Clariant | coco betaine C12-C14 lauryl dimethyl betaine betaines, C12-14-alkyldimethyl |

TABLE 22-continued

Selected Surfactants for Biological Screening

| Surfactant | Manufacturer | Chemical Composition |
|---|---|---|
| GENAPOL ® LRO | Clariant | alcohols, C12-14, ethoxylated, sulfates, sodium salts<br>sodium alkyl ether sulfate; sodium lauryl ether sulfate |
| GEROPON ® DOS/PG | Solvay | sodium-2-ethylhexylsulfosuccinate;<br>sodium di-2ethylhexyl sulphosuccinate<br>docusate sodium |
| HORDAPHOS ® 1306 | Clariant | alkyl polyethylene glycol ether phosphoric acid mono-/diester (50/50), acid form<br>isotridecyl polyethoxy (6 EO) phosphoric acid mono-/diester;<br>poly(oxy-1,2-ethanediyl), α-isotridecyl-ω-hydroxy-phosphate |
| LOXANOL ® CA 5912<br>(aka LOXANOL ® K12 P) | Cognis | sodium dodecyl sulfate<br>sulfuric acid monododecyl ester sodium salt (1:1) |

Example 16. In Vivo Preventive Test on Sphaerotheca (Cucumbers)

Solutions of SERENADE® ASO (Bacillus subtilis QST713 fermentation product) alone, HORDAPHOS® 1306 (alkyl polyethylene glycol ether phosphoric acid mono/diester) alone, and combinations that had been mixed and then equilibrated for at least 24 hours were prepared in water in the desired concentrations and applied to young cucumber plants. After the spray coating had dried on, the plants were inoculated with an aqueous spore suspension of Sphaerotheca fuliginea. Subsequently the plants were placed in a greenhouse at approximately 23° C. and a relative atmospheric humidity of approximately 70%. The test was evaluated 7 days after the inoculation. 0% means an efficacy which corresponds to that of the untreated control, while an efficacy of 100% means that no disease is observed. The table below (Table 23) clearly shows that the observed activity of the SERENADE® ASO (Bacillus subtilis QST713 fermentation product) solution with HORDAPHOS® 1306 (alkyl polyethylene glycol ether phosphoric acid mono/diester) is greater than the calculated activity, i.e., a synergistic effect is present.

TABLE 23

In vivo Preventive Test on Sphaerotheca (Cucumbers)

| Active Compounds | Application Rate of Compound | Efficacy in % Found* | Calc.** |
|---|---|---|---|
| SERENADE ® ASO | 0.375% | 0 | |
| HORDAPHOS ® 1306 | 0.015% | 0 | |
| SERENADE ® ASO +<br>HORDAPHOS ® 1306 | 0.375% + 0.015% | 70 | 0 |

*found = activity found
**calc. = activity calculated using Colby's formula

Interpretation of the dose response curve of these formulations in terms of a fractional inhibitory concentration index, or CI, resulted in an estimated CI value of 0.8 for the HORDAPHOS® 1306 (alkyl polyethylene glycol ether phosphoric acid mono/diester) and SERENADE® ASO (Bacillus subtilis QST713 fermentation product) combination with regards to Sphaerotheca efficacy.

A critical level of efficacy for the CI calculation was chosen at 50%. CI values <1 imply synergistic action as discussed in e.g., H. Patel et al., Biophysical Journal Volume 106, May 2014, 2115-2125.

Example 17. In Vivo Preventive Test on Venturia (Apples)

Solutions of SERENADE® ASO (Bacillus subtilis QST713 fermentation product) alone, the surfactant alone, and combinations that had been mixed and then equilibrated for at least 24 hours were prepared in water in the desired concentrations and applied to young apple tree plants. After the spray coating had dried on, the plants were inoculated with an aqueous conidia suspension of the causal agent of apple scab (Venturia inaequalis) and then kept for 1 day in an incubation cabinet at approximately 20° C. and a relative atmospheric humidity of 100%. Subsequently, the plants were placed in a greenhouse at approximately 21° C. and a relative atmospheric humidity of approximately 90%. The test was evaluated 10 days after the inoculation. 0% means an efficacy which corresponds to that of the untreated control, while an efficacy of 100% means that no disease is observed. The table below (Table 24) clearly shows that the observed activity of the SERENADE® ASO (Bacillus subtilis QST713 fermentation product) solution with GEROPON® DOS/PG (sodium-2-ethylhexylsulfosuccinate), GENAPOL® LRO (sodium $C_{12}/C_{14}$-fatty alcohol diglycol ether sulfate), HORDAPHOS® 1306 (alkyl polyethylene glycol ether phosphoric acid mono/diester), LOXANOL® K12P (sodium dodecyl sulfate; sulfuric acid monododecyl ester sodium salt), GENAGEN® CAB 818 (cocamidopropyl betaine (C8-C18)) or GENAGEN® KB (C12-C14 lauryl dimethyl betaine) is greater than the calculated activity, i.e., a synergistic effect is present.

TABLE 24

In vivo Preventive Test on *Venturia* (Apples)

| Active Compounds | Application Rate of Compound | Efficacy in % Found* | Calc.** |
|---|---|---|---|
| SERENADE ® ASO | 3% | 61 | |
| | 1.5% | 15 | |
| | 0.75% | 0 | |
| | 0.375% | 0 | |
| GEROPON ® DOS/PG | 0.12% | 28 | |
| | 0.06% | 15 | |
| | 0.03% | 38 | |
| GENAPOL ® LRO | 0.06% | 53 | |
| | 0.03% | 33 | |
| HORDAPHOS ® 1306 | 0.06% | 19 | |
| LOXANOL ® K12P | 0.12% | 73 | |
| | 0.06% | 41 | |
| | 0.03% | 11 | |
| GENAGEN ® CAB 818 | 0.06% | 56 | |
| | 0.03% | 68 | |
| | 0.015% | 4 | |
| GENAGEN ® KB | 0.015% | 15 | |
| SERENADE ® ASO + GEROPON ® DOS/PG | 3% + 0.12% | 95 | 72 |
| SERENADE ® ASO + GEROPON ® DOS/PG | 1.5% + 0.06% | 74 | 28 |
| SERENADE ® ASO + GEROPON ® DOS/PG | 0.75% + 0.03% | 79 | 38 |
| SERENADE ® ASO + GENAPOL ® LRO | 1.5% + 0.06% | 77 | 60 |
| SERENADE ® ASO + GENAPOL ® LRO | 0.75% + 0.03% | 81 | 33 |
| SERENADE ® ASO + HORDAPHOS ® 1306 | 1.5% + 0.06% | 87 | 31 |
| SERENADE ® ASO + LOXANOL ® K12P | 3% + 0.12% | 94 | 89 |
| SERENADE ® ASO + LOXANOL ® K12P | 1.5% + 0.06% | 91 | 50 |
| SERENADE ® ASO + LOXANOL ® K12P | 0.75% + 0.03% | 74 | 11 |
| SERENADE ® ASO + GENAGEN ® CAB 818 | 1.5% + 0.06% | 88 | 63 |
| SERENADE ® ASO + GENAGEN ® CAB 818 | 0.75% + 0.03% | 80 | 68 |
| SERENADE ® ASO + GENAGEN ® CAB 818 | 0.375% + 0.015% | 66 | 4 |
| SERENADE ® ASO + GENAGEN ® KB | 0.375% + 0.015% | 81 | 15 |

*found = activity found
**calc. = activity calculated using Colby's formula

Interpretation of the dose response curve of these formulations in terms of a fractional inhibitory concentration index, or CI, resulted in the estimated CI values shown in Table 25 with regards to *Venturia* efficacy.

A critical level of efficacy for the CI calculation was chosen at 50%. CI values <1 imply synergistic action as discussed in e.g., H. Patel, et al., Biophysical Journal Volume 106, May 2014, 2115-2125.

TABLE 25

Estimated CI Values for SERENADE ® ASO
(*Bacillus subtilis* QST713 Fermentation product)
Adjuvant Combinations

| Adjuvant in Combination | CI |
|---|---|
| GEROPON ® DOS/PG | 0.32 |
| GENAPOL ® LRO | 0.54 |
| HORDAPHOS ® 1306 | 0.52 |
| LOXANOL ® K12 P | 0.52 |
| GENAGEN ® CAB 818 | ~0.8$^a$ |
| GENAGEN ® KB | ~0.7$^a$ |

$^a$The data only allowed for a rough estimation of the CI values for these combinations.

Example 18. In Vivo Preventive Test on *Alternaria* (Tomatoes)

Solutions of SERENADE® ASO (*Bacillus subtilis* QST713 fermentation product) alone, the surfactant alone, and combinations that had been mixed and then equilibrated for at least 24 hours were prepared in water in the desired concentrations and applied to young tomato plants. After the spray coating had dried on, the plants were inoculated with an aqueous spore suspension of *Alternaria solani*. Subsequently the plants were placed in an incubation cabinet at approximately 20° C. and a relative atmospheric humidity of 100%. The test was evaluated 3 days after the inoculation. 0% means an efficacy which corresponds to that of the untreated control while an efficacy of 100% means that no disease is observed. The table below (Table 26) clearly shows that the observed activity of the SERENADE® ASO (*Bacillus subtilis* QST713 fermentation product) solution with GENAPOL® LRO (sodium $C_{12}/C_{14}$-fatty alcohol diglycol ether sulfate), HORDAPHOS® 1306 (alkyl polyethylene glycol ether phosphoric acid mono/diester), or LOXANOL® K12P (sodium dodecyl sulfate; sulfuric acid monododecyl ester sodium salt) is greater than the calculated activity, i.e., a synergistic effect is present.

TABLE 26

In vivo Preventive Test on *Alternaria* (Tomatoes)

| Active Compounds | Application Rate of compound | Efficacy in % Found* | Calc.** |
|---|---|---|---|
| SERENADE ® ASO | 3% | 71 | |
|  | 1.5% | 59 | |
|  | 0.75% | 29 | |
|  | 0.375% | 8 | |
| GENAPOL ® LRO | 0.12% | 27 | |
| HORDAPHOS ® 1306 | 0.03% | 32 | |
|  | 0.015% | 30 | |
| LOXANOL ® K12P | 0.12% | 30 | |
|  | 0.06% | 23 | |
|  | 0.03% | 0 | |
|  | 0.015% | 8 | |
| SERENADE ® ASO + GENAPOL ® LRO | 3% + 0.12% | 85 | 78 |
| SERENADE ® ASO + HORDAPHOS ® 1306 | 0.75% + 0.03% | 73 | 51 |
| SERENADE ® ASO + HORDAPHOS ® 1306 | 0.375% + 0.015% | 68 | 36 |
| SERENADE ® ASO + LOXANOL ® K12P | 3% + 0.12% | 89 | 79 |
| SERENADE ® ASO + LOXANOL ® K12P | 1.5% + 0.06% | 86 | 68 |
| SERENADE ® ASO + LOXANOL ® K12P | 0.75% + 0.03% | 68 | 29 |
| SERENADE ® ASO + LOXANOL ® K12P | 0.375% + 0.015% | 45 | 15 |

*found = activity found
**calc. = activity calculated using Colby's formula

Interpretation of the dose response curve of these formulations in terms of a fractional inhibitory concentration index, or CI, resulted in the estimated CI values shown in Table 25 with regards to *Alternaria* efficacy.

A critical level of efficacy for the CI calculation was chosen at 50%. CI values <1 imply synergistic action as discussed in e.g., H. Patel et al., Biophysical Journal Volume 106, May 2014, 2115-2125.

TABLE 27

Estimated CI Values for SERENADE ® ASO
(*Bacillus subtilis* FQST713 ermentation Product) Adjuvant Combinations

| Adjuvant in Combination | CI |
|---|---|
| GENAPOL ® LRO | 0.87 |
| HORDAPHOS ® 1306 | 0.57 |
| LOXANOL ® K12 P | 0.41 |

Example 19. In Vivo Preventive Test on *Botrytis* (Beans)

SERENADE® ASO (*Bacillus subtilis* QST713 fermentation product) and the adjuvants were diluted in water to the desired concentrations and applied separately and in combination to young bean plants. After the spray coating had dried on, two small pieces of agar covered with growth of *Botrytis cinerea* were placed on each leaf. The inoculated plants were placed in a darkened chamber at 14° C. and a relative atmospheric humidity of 100%. 3 days after the inoculation, the size of the lesions on the leaves was evaluated. 0% means an efficacy which corresponds to that of the untreated control, while an efficacy of 100% means that no disease is observed. The table below (Table 28) clearly shows that the observed activity of SERENADE® ASO (*Bacillus subtilis* QST713 fermentation product) with GENAPOL® LRO (sodium $C_{12}/C_{14}$-fatty alcohol diglycol ether sulfate), HORDAPHOS® 1306 (alkyl polyethylene glycol ether phosphoric acid mono/diester), LOXANOL® K12P (sodium dodecyl sulfate; sulfuric acid monododecyl ester sodium salt), GENAGEN® CAB 818 (cocamidopropyl betaine (C8-C18)) or GENAGEN® KB (C12-C14 lauryl dimethyl betaine) is greater than the calculated activity, i.e., a synergistic effect is present.

TABLE 28

In vivo Preventive Test on *Botrytis* (Beans)

| Active Compounds | Application Rate of Compound | Efficacy in % Found* | Calc.** |
|---|---|---|---|
| SERENADE ® ASO | 6% | 63 | |
|  | 3% | 43 | |
|  | 1.5% | 14 | |
|  | 0.75% | 4 | |
| GENAPOL ® LRO | 0.25% | 55 | |
|  | 0.12% | 43 | |
|  | 0.06% | 39 | |
|  | 0.03% | 39 | |
| HORDAPHOS ® 1306 | 0.25% | 14 | |
|  | 0.12% | 0 | |
| LOXANOL ® K12P | 0.12% | 0 | |
| GENAGEN ® CAB 818 | 0.12% | 32 | |
|  | 0.06% | 29 | |
| GENAGEN ® KB | 0.12% | 39 | |
|  | 0.06% | 18 | |
| SERENADE ® ASO + GENAPOL ® LRO | 6% + 0.25% | 93 | 83 |
| SERENADE ® ASO + GENAPOL ® LRO | 3% + 0.12% | 97 | 68 |
| SERENADE ® ASO + GENAPOL ® LRO | 1.5% + 0.06% | 81 | 48 |
| SERENADE ® ASO + GENAPOL ® LRO | 0.75% + 0.03% | 69 | 41 |
| SERENADE ® ASO + HORDAPHOS ® 1306 | 6% + 0.25% | 76 | 68 |
| SERENADE ® ASO + HORDAPHOS ® 1306 | 3% + 0.12% | 57 | 43 |
| SERENADE ® ASO + LOXANOL ® K12P | 3% + 0.12% | 82 | 43 |
| SERENADE ® ASO + GENAGEN ® CAB 818 | 3% + 0.12% | 80 | 61 |
| SERENADE ® ASO + GENAGEN ® CAB 818 | 1.5% + 0.06% | 64 | 39 |
| SERENADE ® ASO + GENAGEN ® KB | 3% + 0.12% | 86 | 65 |

TABLE 28-continued

In vivo Preventive Test on *Botrytis* (Beans)

| Active Compounds | Application Rate of Compound | Efficacy in % Found* | Calc.** |
|---|---|---|---|
| SERENADE ® ASO + GENAGEN ® KB | 1.5% + 0.06% | 59 | 29 |

*found = activity found
**calc. = activity calculated using Colby's formula

Interpretation of the dose response curve of these formulations in terms of a fractional inhibitory concentration index, or CI, resulted in the estimated CI values shown in Table 25 with regards to *Botrytis* efficacy.

A critical level of efficacy for the CI calculation was chosen at 50%. CI values <1 imply synergistic action as discussed in e.g., H. Patel et al., Biophysical Journal Volume 106, May 2014, 2115-2125.

TABLE 29

Estimated CI Values for SERENADE ® ASO (*Bacillus subtilis* QST713 Fermentation Product) Adjuvant Combinations

| Adjuvant in Combination | CI |
|---|---|
| GENAPOL ® LRO | 0.34 |
| HORDAPHOS ® 1306 | 0.65 |
| GENAGEN ® CAB 818 | 0.42 |
| GENAGEN ® KB | 0.63 |

Example 20. Identification of Additional Surfactants that Increase Antifungal Activity of *Bacillus subtilis* QST713 Fermentation Product in SERENADE® ASO In separate screening experiments several other surfactants were evaluated for their effect on the antifungal activity of *Bacillus subtilis* QST713 whole broth. Among the surfactants tested were several formulations of sodium dioctyl sulfosuccinate including MONAWET™ MO-75E (also designated herein as "MO75E") and MULTIWET™ MO-70R (also designated herein as "MO70R") and a formulation of alpha olefin sulphonate known as TERWET® 1004 (also designated herein as "TERWET").

A *Bacillus subtilis* QST713 whole broth (WB) was prepared by culturing the strain in a soy-based medium. The WB was then mixed and equilibrated for at least 24 hours with 15% MONAWET™ MO-75E (sodium dioctyl sulphosuccinate); MULTIWET™ MO-70R (sodium dioctyl sulphosuccinate); TERWET® 1004 (alpha olefin sulphonate); or GENAPOL® LRO (sodium $C_{12}/C_{14}$-fatty alcohol diglycol ether sulfate). A negative control of WB without any surfactant and a positive control of an alternative formulation of *Bacillus subtilis* QST713 with increased antifungal activity were included in the experiment.

Each of the treatments was applied to plants at the rates indicated in Table 30. Subsequently, the plants were inoculated with a spore suspension of *Botrytis cinerea*. Several days later when disease was evident in the untreated control plants the plants were evaluated for percent disease control. The results shown in Table 30 are the average values of three independent measurements. Each of the mixtures of WB and surfactant was prepared in duplicate (designated "#1" and "#2"), and the duplicate mixtures were assessed independently.

The mixtures of WB with MONAWET™ MO-75E (dioctyl sodium sulphosuccinate); MULTIWET™ MO-70R (sodium dioctyl sulphosuccinate); or TERWET® 1004 (alpha olefin sulphonate) had increased antifungal activity similar to that observed with WB mixed with GENAPOL® LRO (sodium Cy/Cm-fatty alcohol diglycol ether sulfate) and the positive control. These data suggest that a synergistic effect results from mixing and equilibrating the WB with sodium dioctyl sulphosuccinate or alpha olefin sulphonate similar to that observed with WB mixed and equilibrated with GENAPOL® LRO.

TABLE 30

Average Disease Control Observed with *Bacillus subtilis* QST713 Whole Broth Mixed with Various Surfactants Applied to Plants Infected with *Botrytis cinerea*

| Sample Name | Rate | Average % Disease Control |
|---|---|---|
| WB + MONAWET ™ MO-75E #1 | 2% | 90 |
| WB + MONAWET ™ MO-75E #1 | 4% | 100 |
| WB + MONAWET ™ MO-75E #2 | 2% | 90 |
| WB + MONAWET ™ MO-75E #2 | 4% | 95 |
| WB + MULTIWET ™ MO-70R #1 | 2% | 90 |
| WB + MULTIWET ™ MO-70R #1 | 4% | 100 |
| WB + MULTIWET ™ MO-70R #2 | 2% | 80 |
| WB + MULTIWET ™ MO-70R #2 | 4% | 100 |
| WB + TERWET ® 1004 #1 | 2% | 70 |
| WB + TERWET ® 1004 #1 | 4% | 90 |
| WB + TERWET ® 1004 #2 | 2% | 83 |
| WB + TERWET ® 1004 #2 | 4% | 88 |
| WB + GENAPOL ® LRO #1 | 2% | 67 |
| WB + GENAPOL ® LRO #1 | 4% | 88 |
| WB + GENAPOL ® LRO #2 | 2% | 77 |
| WB + GENAPOL ® LRO #2 | 4% | 77 |
| WB without surfactant | 2% | 0 |
| WB without surfactant | 4% | 25 |
| WB without surfactant | 8% | 67 |
| WB without surfactant | 16% | 67 |
| WB Positive Control | 1% | 75 |
| WB Positive Control | 2% | 93 |
| WB Positive Control | 4% | 100 |
| Untreated Control | — | 0 |

Example 21. Efficacy Against Plant Pathogens of a Sorbitan Ester in Combination with *Bacillus subtilis* QST713

The present study investigated the efficacy against a variety of plant pathogens of the commercial product, SERENADE® ASO (*Bacillus subtilis* QST713 fermentation product), with and without a mixture of SPAN® 20 (sorbitan monolaurate) and TWEEN® 20 (polyethylene glycol sorbitan monolaurate). The mixture contained 62.5% SPAN® 20 and 37.5% TWEEN® 20 by weight. The application rates of SERENADE® ASO refer to the amount of (1.67%) *Bacillus subtilis* QST713 contained in the product SERENADE® ASO.

SERENADE® ASO was diluted in water to concentrations of 1000 ppm, 500 ppm, 250 ppm, and 125 ppm and applied to plants with or without the mixture of SPAN® 20 and TWEEN® 20 ("SPAN® 20+TWEEN® 20") at a concentration of 3000 ppm. Subsequently, the plants were inoculated with the various plant pathogens and scored for percent disease control with the following eight plant pathogen bioassays: (1) tomato late blight, *Phytophthora infestans* ("Late Blight"); (2) grape downy mildew, *Plasmopara viticola* ("Downy Mildew"); (3) cucumber powdery mildew, *Sphaerotheca fuliginea* ("Powdery Mildew"); (4) apple scab, *Venturia inaequalis* ("Scab"); (5) tomato early blight, *Alternaria solani* ("Early Blight"); (6) brown rust of snap bean, *Uromyces appendiculatus* ("Bean Rust"); (7) Asian soybean rust, *Phakopsora pachyrhizi* ("Soy Rust"); and (8) *Botrytis* grey mould on snap beans, *Botrytis cinerea* ("Grey Mould").

Results

The results of the eight plant pathogen assays are shown in Tables 31 through 34.

TABLE 31

Percent Disease Control Observed with Plants Treated with SPAN ® 20 + TWEEN ® 20, SERENADE ® ASO, or SERENADE ® ASO + SPAN ® 20 + TWEEN ® 20

| Plant Treatment | ppm | Late Blight | Downy Mildew | Powdery Mildew | Scab | Early Blight | Bean Rust | Soy Rust | Grey Mould |
|---|---|---|---|---|---|---|---|---|---|
| Uninfected (positive control) | 0 | 100 | 93 | 100 | 100 | 93 | 100 | 100 | 100 |
| H₂O (negative control) | 0 | 0 | 0 | 0 | 0 | 0 | 0 | 0 | 0 |
| SPAN ® 20 + TWEEN ® 20 | 3000 | 0 | 16 | 0 | 23 | 0 | 0 | 0 | 15 |
| SERENADE ® ASO | 1000 | 0 | 24 | 37 | 28 | 92 | 70 | 73 | 53 |
|  | 500 | 0 | 0 | 30 | 11 | 68 | 70 | 70 | 35 |
|  | 250 | 0 | 0 | 0 | 11 | 24 | 50 | 15 | 0 |
|  | 125 | 0 | 0 | 0 | 0 | 16 | 30 | 8 | 0 |
| SERENADE ® ASO + SPAN ® 20 + TWEEN ® 20 | 1000 | 8 | 77 | 43 | 91 | 73 | 50 | 70 | 59 |
|  | 500 | 0 | 41 | 37 | 78 | 51 | 60 | 60 | 53 |
|  | 250 | 0 | 59 | 30 | 79 | 35 | 50 | 45 | 0 |
|  | 125 | 0 | 51 | 0 | 67 | 30 | 25 | 30 | 0 |

TABLE 32

Comparison of Observed and Calculated Efficacies with Downy Mildew

| Active Compounds | Application Rate of Active Compound (ppm) | Efficacy in % Found* | Calc.** |
|---|---|---|---|
| SPAN ® 20 + TWEEN ® 20 | 3000 | 16 | |
| SERENADE ® ASO | 1000 | 24 | |
| SPAN ® 20 + TWEEN ® 20 + SERENADE ® ASO | 3000 + 1000 | 77 | 36 |

*Found = activity observed
**Calc. = activity calculated using Colby's formula

TABLE 33

Comparison of Observed and Calculated Efficacies with Powdery Mildew

| Active Compounds | Application Rate of Active Compound (ppm) | Efficacy in % Found* | Calc.** |
|---|---|---|---|
| SPAN ® 20 + TWEEN ® 20 | 3000 | 0 | |
| SERENADE ® ASO | 1000 | 37 | |
| SPAN ® 20 + TWEEN ® 20 + SERENADE ® ASO | 3000 + 1000 | 43 | 37 |

*Found = activity observed
**Calc. = activity calculated using Colby's formula

TABLE 34

Comparison of Observed and Calculated Efficacies with Scab

| Active Compounds | Application Rate of Active Compound (ppm) | Efficacy in % Found* | Calc.** |
|---|---|---|---|
| SPAN ® 20 + TWEEN ® 20 | 3000 | 23 | |
| SERENADE ® ASO | 1000 | 28 | |
| SPAN ® 20 + TWEEN ® 20 + SERENADE ® ASO | 3000 + 1000 | 91 | 45 |

*Found = activity observed
**Calc. = activity calculated using Colby's formula

Conclusions

Application of SERENADE® ASO with the mixture of SPAN® 20 and TWEEN® 20 to the plants enhanced control of several of the pathogens over application of SERENADE® ASO alone. The combination produced a synergistic effect when applied to plants infected with Downy Mildew, Powdery Mildew, and Scab.

Example 22. Efficacy of SPAN® 20 in Combination with *Bacillus subtilis* QST713 Whole Broth Against *Botrytis cinerea*

To obtain whole broth cultures of *Bacillus subtilis* QST713, seed flasks containing Luria Broth (LB) were inoculated with *Bacillus subtilis* QST713 and grown overnight at 30° C. The next day, aliquots from each seed flask were inoculated into 200 mL of a soy-based medium in a 1 L shake flask and grown until sporulation. Briefly, the shake flask culture was maintained at a temperature between 30° C. and 32° C. and at a shaker setting of 200 to 220 rpm. After approximately 3 days of incubation, when cell growth and metabolite production had stopped, the culture broth was harvested.

SPAN® 20 (sorbitan monolaurate) was applied alone or in combination with *Bacillus subtilis* QST713 Whole Broth ("QST713 Whole Broth") to plants infected with *Botrytis cinerea* and the percent disease control was determined SPAN® 20 and QST713 Whole Broth were both applied at 0.5 weight %.

The SPAN® 20 and QST713 Whole Broth combinations were heated to 40° C., 50° C., 60° C., 70° C., or 80° C. for one hour and allowed to cool to room temperature prior to application to the plants. The results shown in FIG. 1 demonstrate that heat activation is required for optimal control of *Botrytis cinerea*. Heat activation at 60° C., 70° C., or 80° C. produced the highest efficacies with the percent control achieved with these combinations having a synergistic effect as compared to the SPAN® 20 and QST713 Whole Broth treatments applied separately.

Example 23. SPAN® 20 Fungicidal Activity Against Tomato Late Blight and Pepper *Botrytis*

Figure 2A:
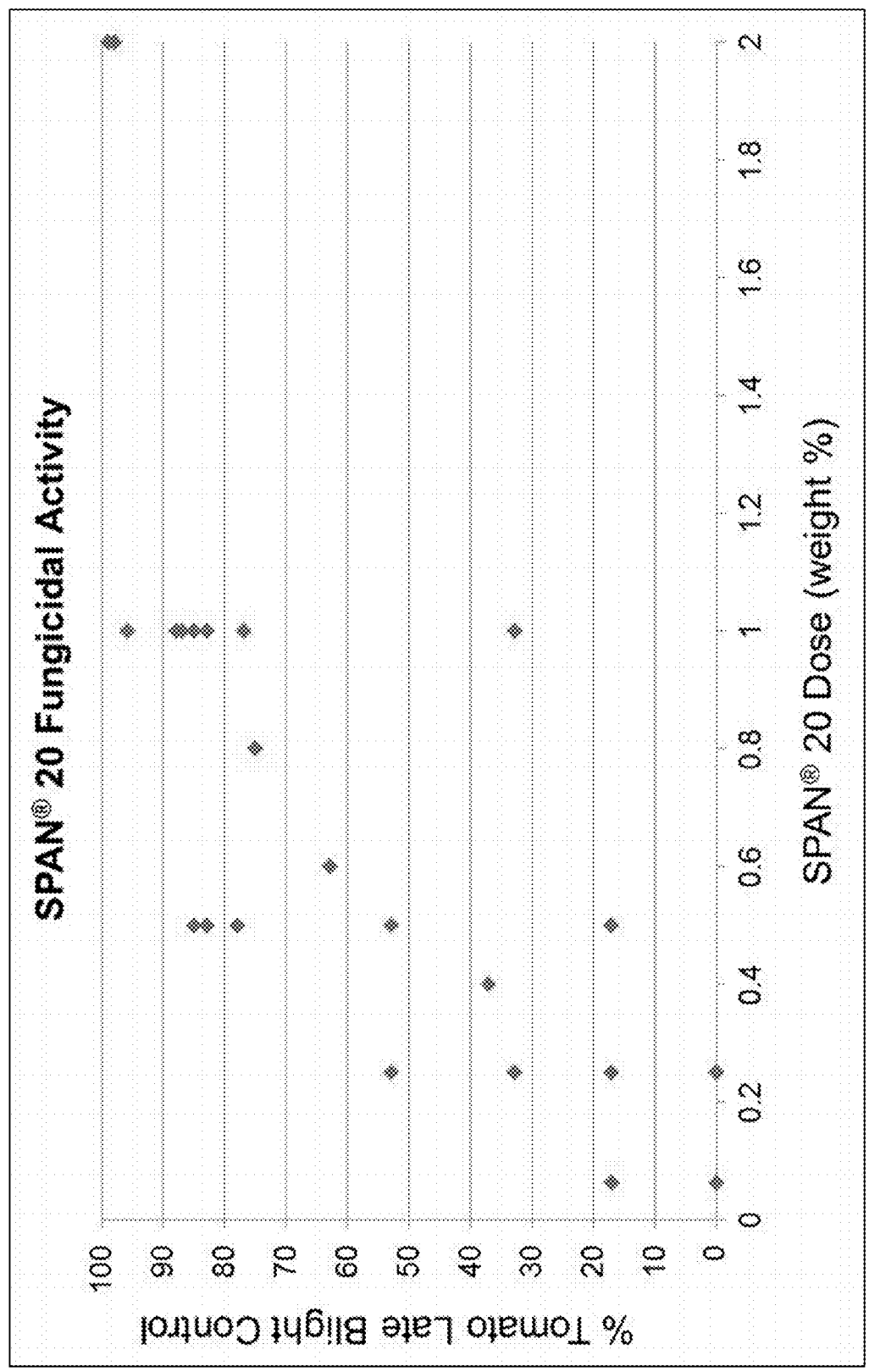
FIG. 2A depicts fungicidal activity of SPAN® 20 (sorbitan monolaurate) at various doses applied to tomato plants infected with *Phytophthora infestans* (Late Blight).
Figure 2B:
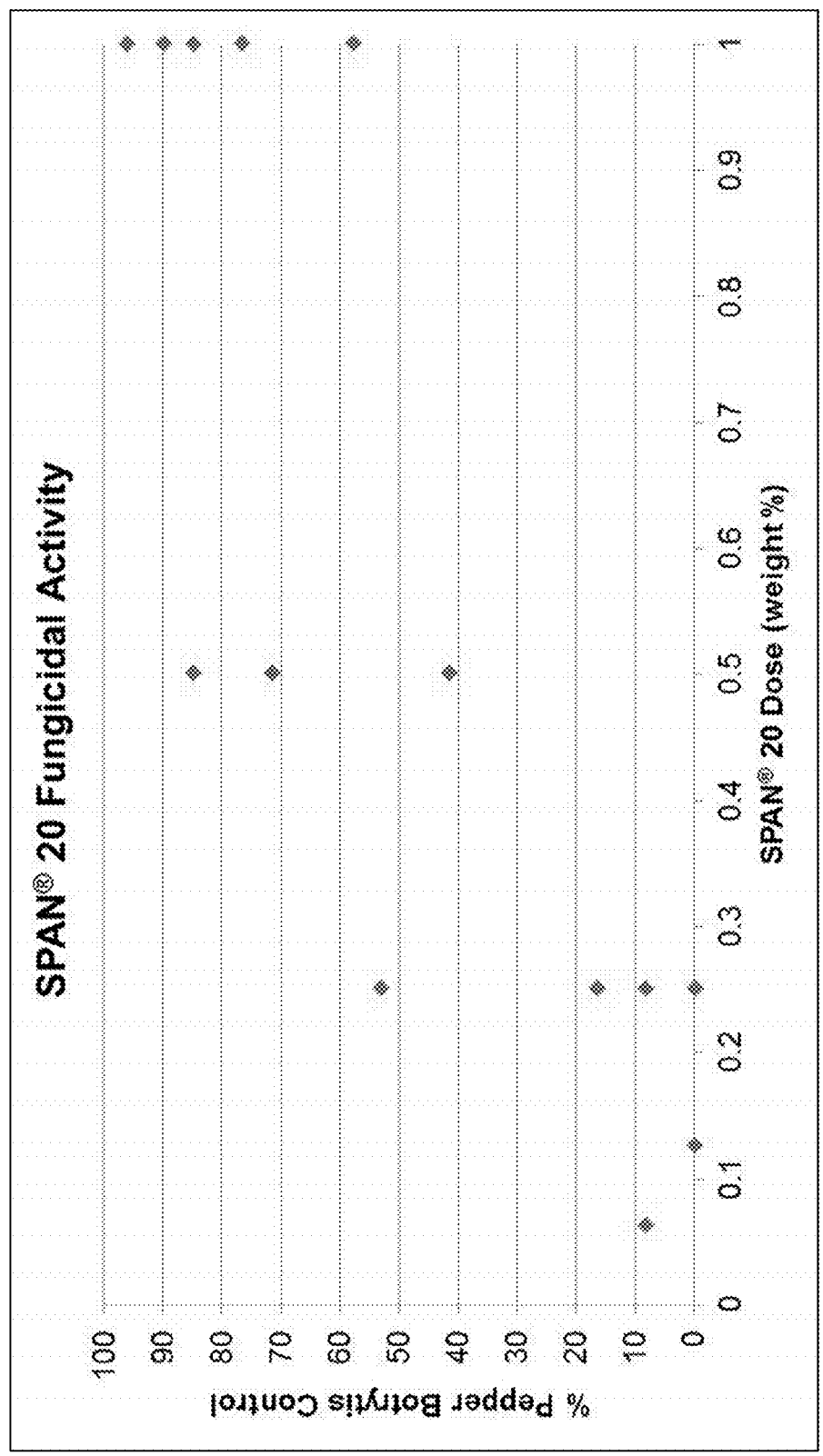
FIG. 2B depicts fungicidal activity of SPAN® 20 (sorbitan monolaurate) at various doses applied to pepper plants infected with *Botrytis cinerea* (Grey Mould). Each diamond (♦) in FIGS. 2A and 2B represents a replicate.
Figure 3:
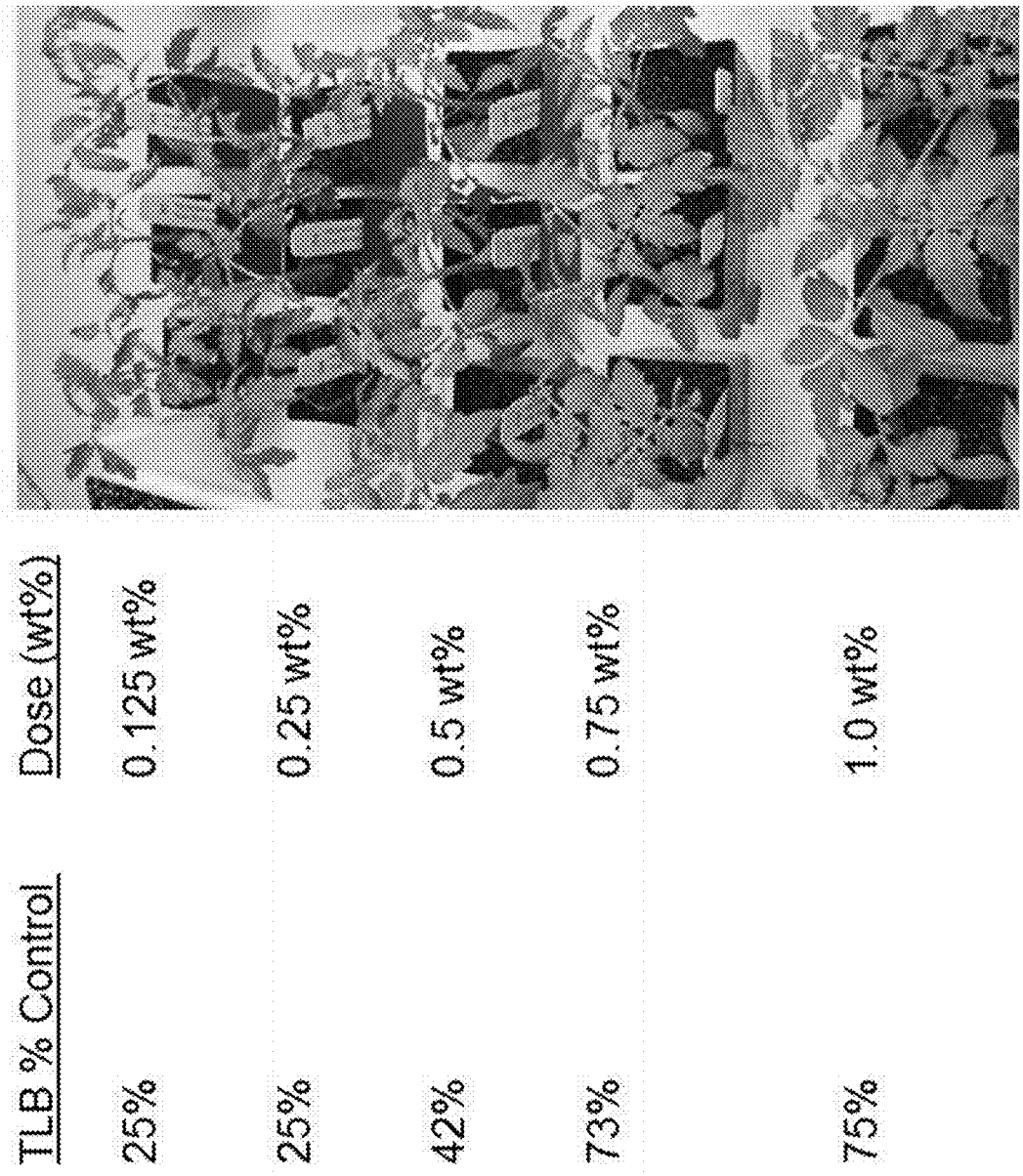
FIG. 3 depicts a representative experiment with SPAN® 20 (sorbitan monolaurate) applied to tomato plants infected with *Phytophthora infestans* (Late Blight or TLB) and the resulting percent control of the disease at various application rates.

A series of experiments was conducted to test the fungicidal activity of SPAN® 20 against Tomato Late Blight (*Phytophthora infestans*) and Pepper Grey Mould (*Botrytis cinerea*) at differing application rates. SPAN® 20 was applied at rates between 0.0625 weight % and 2.0 weight % to tomato plants infected with *Phytophthora infestans*. Successively greater control was observed with increasing application rates, and the highest level of control was observed at 1.0 and 2.0 weight % (see FIG. 2A and FIG. 3, which shows the results of one representative experiment). Similarly, SPAN® 20 was applied at rates between 0.0625 weight % and 1.0 weight % to pepper plants infected with *Botrytis cinerea*, and increasing control of the plant pathogen was observed as higher rates were applied (see FIG. 2B).

Figure 4:
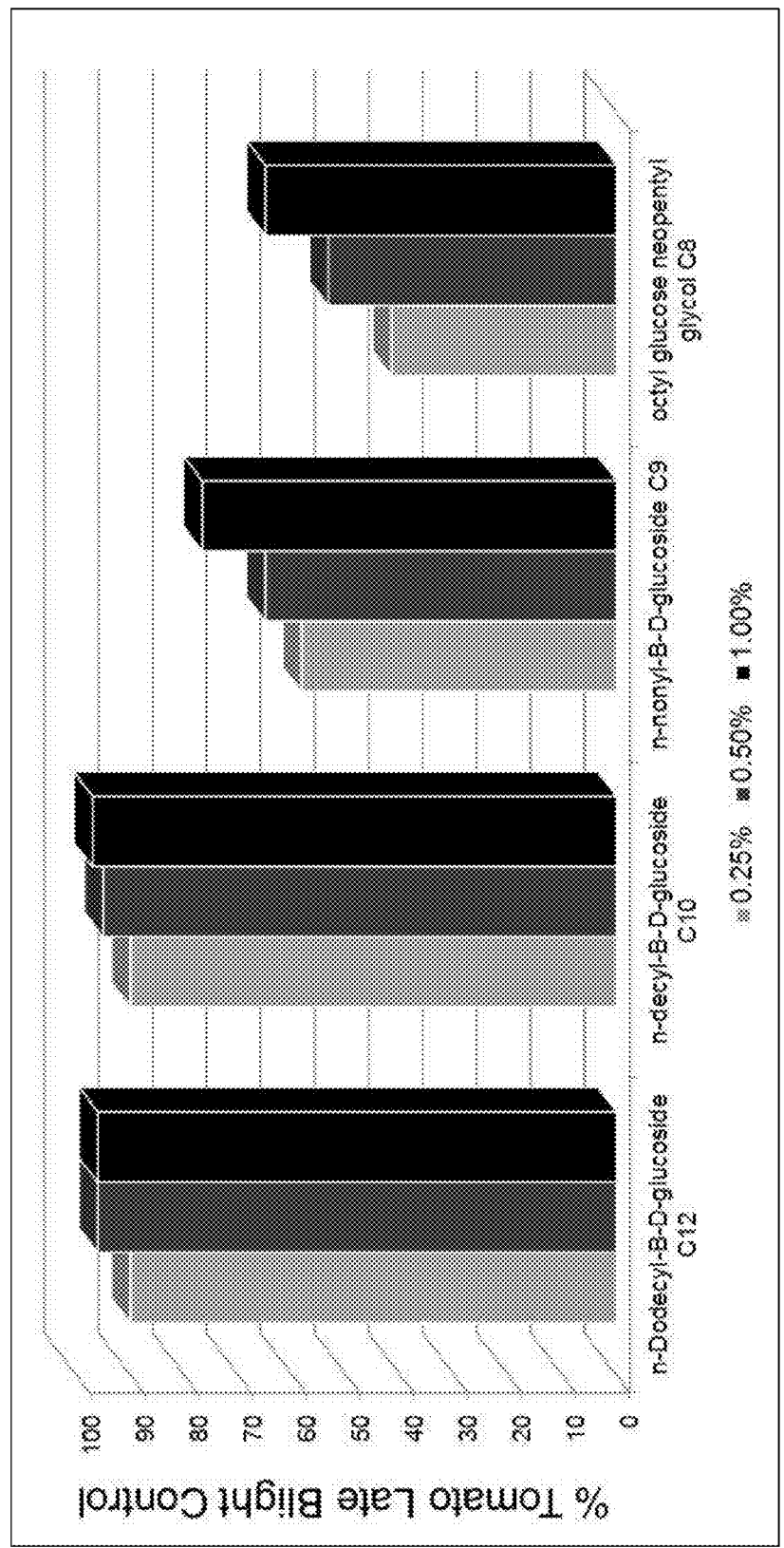
FIG. 4 depicts fungicidal activity of n-dodecyl-B-D-glucoside, n-decyl-B-D-glucoside, n-nonyl-B-D-glucoside, and octyl glucose neopentyl glycol applied at several rates to tomato plants infected with *Phytophthora infestans* (Tomato Late Blight).

Example 24. Activity of Other Nonionic Amphiphiles Against Tomato Late Blight Having observed fungicidal activity with SPAN® 20, other nonionic amphiphilic compounds were also investigated for similar activity. The alkyl glucosides, n-dodecyl-B-D-glucoside, n-decyl-B-D-glucoside, and n-nonyl-B-D-glucoside, and the related compound, octyl glucose neopentyl glycol were each applied to infected tomato plants at 0.25 weight %, 0.50 weight percent, and 1.00 weight %. At each application rate, fungicidal activity was observed for all four compounds (see FIG. 4). The compounds with $C_{10}$- and $C_{12}$-alkyl chains had higher activity against Tomato Late Blight than did those with the shorter $C_9$- and $C_8$-alkyl chains.

In additional experiments, the fungicidal activities of SPAN® 20 (sorbitan monolaurate), SPAN® 90 (sorbitan oleate), SPAN® 85 (sorbitan trioleate), sucrose monodecanoate, n-dodecyl-B-D-glucoside, n-decyl-B-D-glucoside, and n-nonyl-B-D-glucoside were determined when applied at 1.0 weight % in 50% ethanol to tomato plants infected with *Phytophthora infestans*. The results are shown in Table 35.

TABLE 35

Control of Tomato Late Blight (*Phytophthora infestans*) Resulting from Application of Sorbitan Esters or Alykyl Glucosides to Infected Tomato Plants

| Plant Treatment | Percent Control of Tomato Late Blight |
|---|---|
| SPAN ® 20 (sorbitan monolaurate) | 75% |
| SPAN ® 80 (sorbitan oleate) | 50% |
| SPAN ® 85 (sorbitan trioleate) | 0% |
| sucrose monodecanoate | 25% |
| n-dodecyl-B-D-glucoside | 96% |
| n-decyl-B-D-glucoside | 97% |
| n-nonyl-B-D-glucoside | 77% |

Example 25. In Vitro Control of *Xanthomonas campestris* pv. *vesicatoria*

A whole broth culture of *Bacillus subtilis* QST713 was prepared in a soy-based medium as described above. *Bacillus subtilis* cells were removed from the whole broth culture by centrifugation. The adjuvant alone, cell-free whole broth solution alone, and a mixture of 95% cell-free whole broth with 5% adjuvant were each diluted in water to various final concentrations and applied to 96-well plates containing bacterial suspensions of *Xanthomonas campestris* pv. *vesicatoria*. After several hours, the $OD_{600}$ in each well was measured and compared to the initial $OD_{600}$ to determine the relative bacterial growth compared to that of the bacterial suspension in the untreated well. An efficacy for each treatment was determined 0% means an efficacy with bacterial growth corresponding to or better than that of the untreated control, while an efficacy of 100% means that no bacterial growth was observed.

The table below (Table 36) clearly shows that the observed antibacterial activity of *Bacillus subtilis* QST713 cell-free whole broth with GENAPOL® LRO (sodium $C_{12}/C_{14}$-fatty alcohol diglycol ether sulfate) or HOSTAPHAT® 1306 (alkyl polyethylene glycol ether phosphoric acid mono/diester) is greater than the calculated activity, i.e., a synergistic effect is present.

TABLE 36

In vitro Control of *Xanthomonas campestris* pv. *vesicatoria*

| Active Compounds | Application Rate of Compound | Efficacy in % Found* | Calc.** |
|---|---|---|---|
| *Bacillus subtilis* QST713 cell-free whole broth | 0.11% | 7 | |
| | 0.22% | 0 | |
| | 0.44% | 50 | |
| | 0.88% | 77 | |
| GENAPOL ® LRO | 0.11% | 57 | |
| | 0.22% | 63 | |
| | 0.44% | 41 | |
| | 0.88% | 53 | |
| HOSTAPHAT ® 1306 | 0.11% | 43 | |
| | 0.22% | 37 | |
| | 0.44% | 27 | |
| *Bacillus subtilis* QST713 cell-free whole broth + GENAPOL ® LRO | 0.11% | 70 | 60 |
| | 0.22% | 75 | 63 |
| | 0.44% | 93 | 70 |
| | 0.88% | 100 | 89 |

TABLE 36-continued

In vitro Control of *Xanthomonas campestris* pv. *vesicatoria*

| Active Compounds | Application Rate of Compound | Efficacy in % Found* | Calc.** |
|---|---|---|---|
| *Bacillus subtilis* QST713 cell-free whole broth + HOSTAPHAT ® 1306 | 0.11% 0.22% 0.44% | 59 58 90 | 47 37 64 |

*found = activity found
**calc. = activity cal

GENAPOL® LRO (sodium $C_{12}/C_{14}$-fatty alcohol diglycol ether sulfate) were prepared as described in Example 20. Separate mixtures with 5% (0.05), 10% (0.10), and 15% (0.15) surfactant were prepared for each surfactant except for GENAPOL® LRO which only had a 5% (0.05) mixture.

The relative concentrations of iturins and surfactins in the supernatants were determined in the WB-surfactant mixtures and in WB without surfactant. Pellet and supernatant fractions were separated by centrifuging each sample. The samples were extracted with acetonitrile to isolate the lipophilic material, and the relative quantities of iturins and surfactins in the supernatants were determined with analytical HPLC chromatography. Each value of total iturins and surfactins was normalized by the amount of WB present in the related extracted sample. The results appear in FIG. 5 with lipopeptide concentrations reported as percent total iturins and surfactins in the supernatants normalized to the amount of WB.

Figure 5:
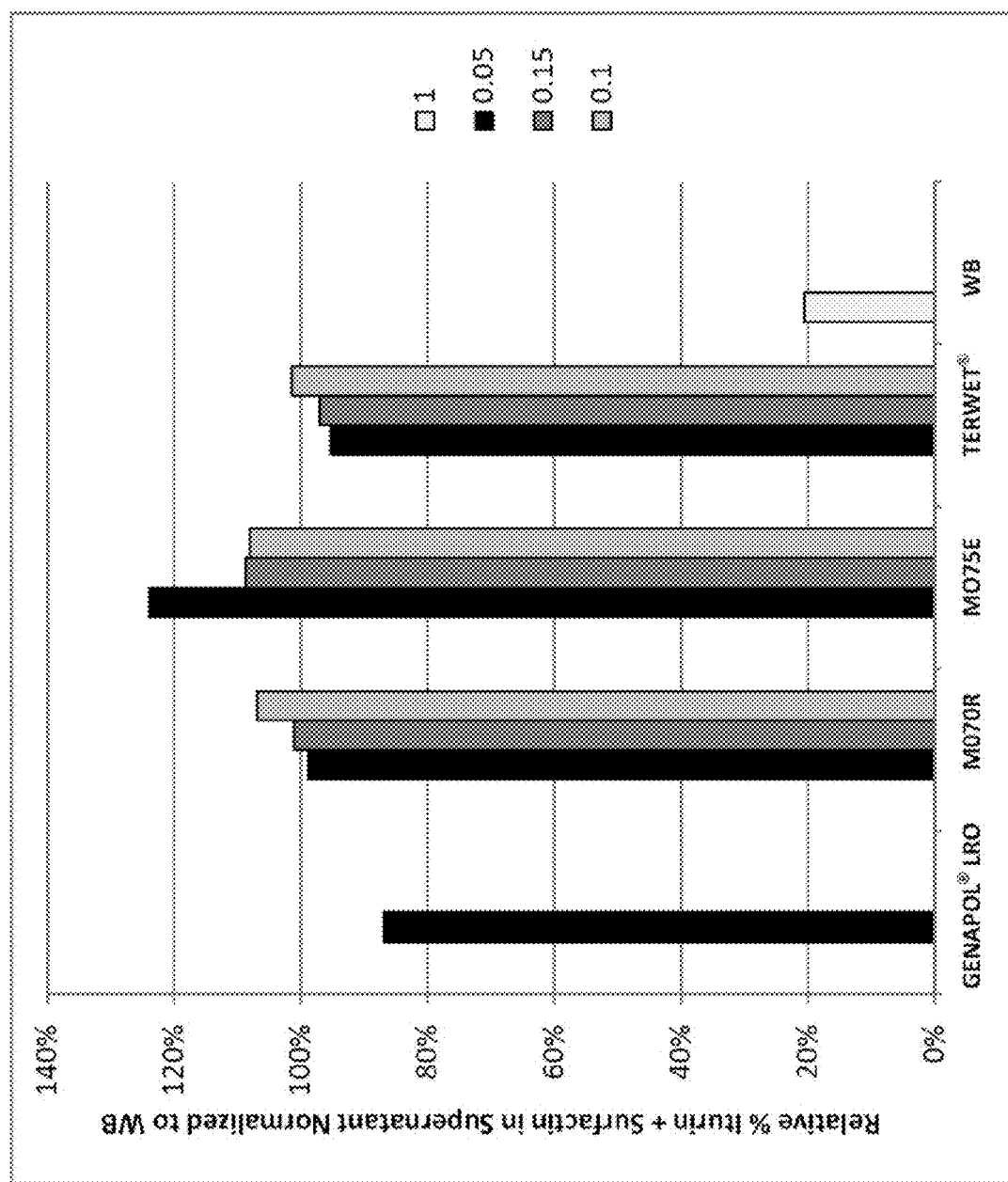
FIG. 5 depicts the relative amounts of iturins and surfactins in the supernatants remaining after centrifugation of *Bacillus subtilis* QST713 whole broth ("WB") alone and WB mixed with MONAWET™ MO-75E (sodium dioctyl sulphosuccinate; "MO-75E"); MULTIWET™ MO-70R (sodium dioctyl sulphosuccinate; "MO-70R"); TERWET® 1004 (alpha olefin sulphonate; "TERWET®"); or GENAPOL® LRO (sodium Cy/Cm-fatty alcohol diglycol ether sulfate). Each value was normalized to the amount of WB present in the sample.

As shown in FIG. 5, only about 20% of the total iturins and surfactins were present in the supernatant of WB without surfactant added. In contrast, between about 85% and about 100% of the total iturins and surfactins were present in the samples containing WB mixed and equilibrated with MONAWET™ MO-75E (sodium dioctyl sulphosuccinate); MULTIWET™ MO-70R (sodium dioctyl sulphosuccinate); TERWET® 1004 (alpha olefin sulphonate); or GENAPOL® LRO (sodium $C_{12}/C_{14}$-fatty alcohol diglycol ether sulfate). Without wishing to be bound to any theory, the data suggest that addition of the surfactants to the WB followed by equilibration results in movement of the lipopeptides with antifungal activity from the pellet fraction to the supernatant fraction where they may have increased bioavailability and enhanced activity against plant pathogens.

Example 29. Quantification of *Bacillus subtilis* QST713 Lipopeptides in Supernatant of SERENADE® ASO Mixed and Equilibrated with Surfactants SERENADE® ASO (*Bacillus subtilis* QST713 fermentation product) was mixed with an adjuvant selected from Table 39 and water to produce a homogenous formulation consisting of 85% SERENADE® ASO, 3.5% adjuvant, and 11.5% water. The formulations were equilibrated for 3 h at 54° C. and then stored at room temperature.

TABLE 39

Selected Surfactants for Lipopeptide Solubilization

| Surfactant | Manufacturer | Chemical Composition |
| --- | --- | --- |
| GERONOL ® CFAR | Solvay | alkylethoxyphosphate amine salt; a blend of mono- and di-C4-10-alkyl phosphates |
| GENAGEN ® CAB 818 | Clariant | cocamidopropyl betaine (C8-C18) 1-propanaminium, 3-amino-N-(carboxymethyl)-N,N-dimethyl-, N-coco acyl derivatives, hydroxides, inner salts |
| SYNERGEN ® GL 5 | Clariant | copolymer of glycerol/coconut fatty acid/phthalic acid anhydride |
| MULTITROPE ™ 1213 | Croda | PEG-4 decyl phosphate poly(oxy-1,2-ethanediyl), α-hydro-ω-hydroxy-, mono-C8-10-alkyl ethers, phosphates |
| GEROPON ® DOS/PG | Solvay | sodium-2-ethylhexylsulfosuccinate; sodium di-2ethylhexyl sulphosuccinate docusate sodium |
| GENAGEN ® KB | Clariant | coco betaine C12-C14 lauryl dimethyl betaine betaines, C12-14-alkyldimethyl |
| HORDAPHOS ® 1306 | Clariant | alkyl polyethylene glycol ether phosphoric acid mono/diester (50/50), acid form isotridecyl polyethoxy (6 EO) phosphoric acid mono-/diester; poly(oxy-1,2-ethanediyl), α-isotridecyl-ω-hydroxy- phosphate |
| LOXANOL ® CA 5912 (aka LOXANOL ® K12 P) | Cognis | sodium dodecyl sulfate sulfuric acid monododecyl ester sodium salt (1:1) |
| GENAPOL ® LRO | Clariant | alcohols, C12-14, ethoxylated, sulfates, sodium salts sodium alkyl ether sulfate; sodium lauryl ether sulfate |

To quantify the solubilization of lipopeptides in the supernatants of SERENADE® ASO (*Bacillus subtilis* QST713 fermentation product) alone and mixed with each surfactant the total amount of lipopeptide and the amount of lipopeptide in the supernatant after centrifugation were measured for each sample. Lipopeptides were extracted with an acetonitrile solution, and the quantities of iturins, surfactins, and agrastatins were determined with liquid chromatography-mass spectrometry (LC-MS). The relative amount of lipopeptide in the supernatant was determined as a percentage calculated by dividing the amount of lipopeptide in the supernatant after centrifugation by the total amount of lipopeptide.

Figure 6:
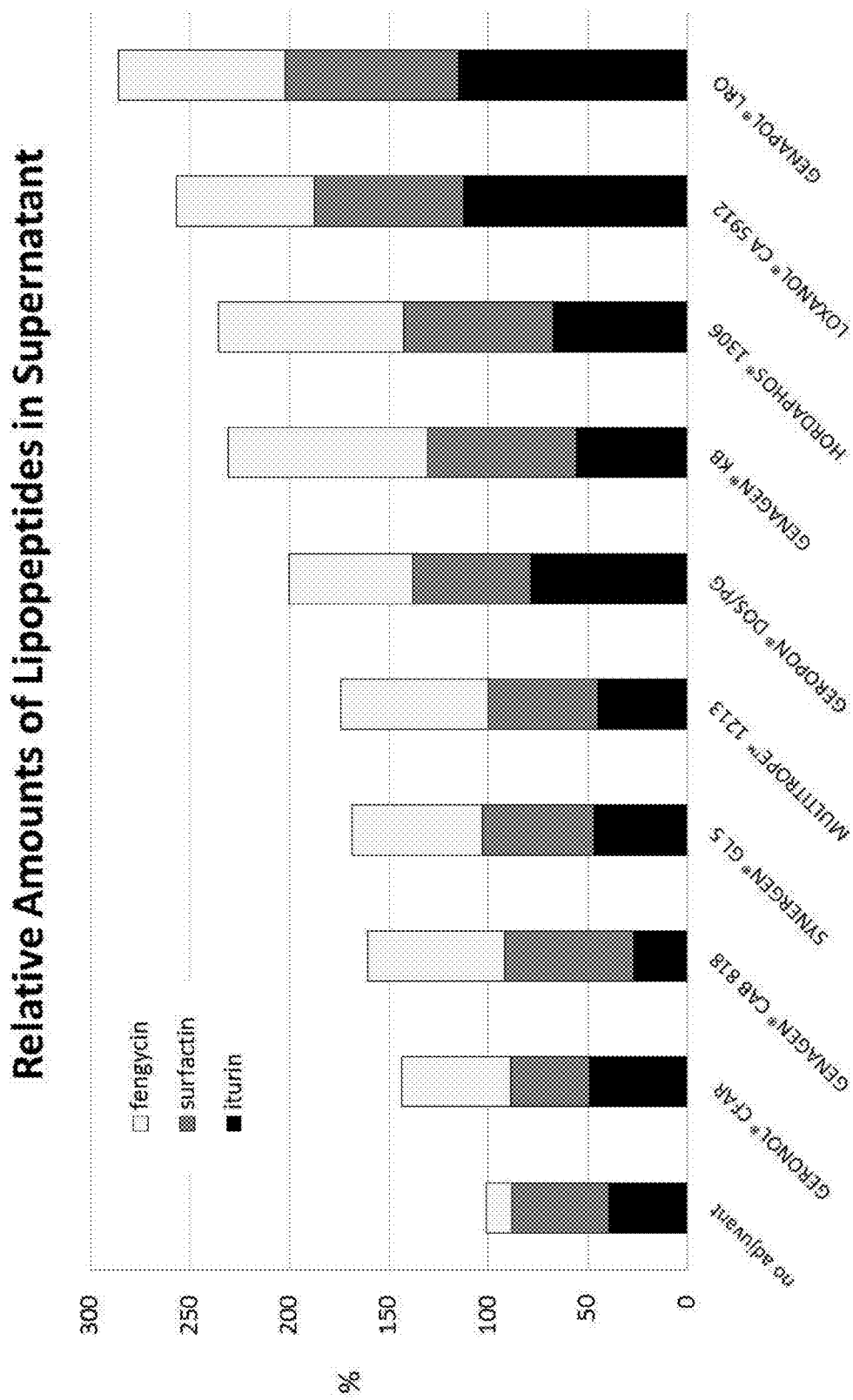
FIG. 6 depicts the relative amounts of fengycins (including plipastatins and agrastatins), surfactins, and iturins in the supernatants remaining after centrifugation of SERENADE® ASO (*Bacillus subtilis* QST713 fermentation product) alone ("no adjuvant") or mixed with one of several surfactants.

The results are shown in FIG. 6 as a stacked bar graph. Complete solubilization of the lipopeptides by the surfactant would result in a stacked bar rising to 300%. Several surfactants that had previously demonstrated synergistic antifungal activity when mixed with *Bacillus subtilis* QST713 fermentation product (e.g., GENAPOL® LRO (sodium $C_{12}/C_{14}$-fatty alcohol diglycol ether sulfate); LOXANOL® K12P (sodium dodecyl sulfate; sulfuric acid monododecyl ester sodium salt); and HORDAPHOS® 1306

(alkyl polyethylene glycol ether phosphoric acid mono/diester)) demonstrated the greatest effect on solubilization of the lipopeptides.

Example 30. In Vivo Control of *Erwinia amylovora*

Apple blossoms were placed in a sugar solution and inoculated with a Fire Blight (*Erwinia amylovora*) bacterial suspension. The blossoms were then sprayed with the treatments shown in Table 40 at the indicated concentrations diluted in water. Streptomycin sulfate was included as a positive control. The blossoms were incubated at 23-25° C. and a relative humidity of 100%. After 6-7 days, the number of blossoms with bacterial ooze was determined, and the efficacy of each treatment was calculated. The efficacy was determined by the reduction in infected blossoms compared to the control blossoms treated with water. The test was carried out at least four times for each treatment, and the average disease control was reported.

TABLE 40

In vivo control of *Erwinia amylovora*

| Blossom Treatment | Concentration (%) Applied to Blossoms | Efficacy in % |
|---|---|---|
| Streptomycin sulfate | 0.025 | 89 |
| SERENADE ® ASO | 0.50 | 7 |
| (*B. subtilis* QST713 fermentation product) | 1 | 8 |
|  | 5 | 57 |
| 5% sodium lauryl ether sulfate (SLES) | 0.5 | 15 |
|  | 1 | 8 |
| *B. subtilis* QST713 WB + 5% SLES (suspension concentrate) | 0.5 | 79 |
|  | 1 | 69 |
|  | 5 | 85 |

The combination of *B. subtilis* QST713 WB with 5% SLES demonstrated significantly greater control of *Erwinia amylovora* on the apple blossoms than did the SERENADE® ASO (*Bacillus subtilis* QST713 fermentation product) or 5% SLES treatments suggesting a synergistic antibacterial effect with the combination.

The tradename "GENAPOL® LRO", as used herein, is synonymous with the terms "sodium laureth sulfate" and "sodium lauryl ether sulfate" ("SLES").

Example 31. In Vivo Control of *Pseudomonas syringae* pv. *tomato*

A whole broth culture of *Bacillus subtilis* QST713 was prepared in a soy-based medium. 5% adjuvant alone (GENAPOL® LRO (sodium $C_{12}/C_{14}$-fatty alcohol diglycol ether sulfate)), 95% whole broth alone, and a mixture of 95% whole broth with 5% adjuvant were each diluted in deionized ("DI") water to the final concentrations shown in Table 41. The mixtures were allowed to equilibrate at least four hours prior to application. The treatments were applied to tomato plants and allowed to dry. The next day, the plants were inoculated with a bacterial suspension of *Pseudomonas syringae* pv. *tomato*. After bacterial disease was evident in the untreated controls the plants were evaluated for efficacy of disease control. Each efficacy value represents the average of three measurements. 0% means an efficacy which corresponds to that of the untreated control, while an efficacy of 100% means that no disease is observed.

The mixture of 95% whole broth with 5% adjuvant consistently produced the greatest disease control at each rate tested (see Table 41). At the 0.25% application rate, the mixture demonstrated a super additive effect suggesting a synergistic bactericidal effect.

TABLE 41

In vivo control of *Pseudomonas syringae* pv. *tomato*

| Treatment | Rate (% v/v) | Efficacy in % |
|---|---|---|
| Untreated Control | — | 0 |
| 95% *B. subtilis* QST713 Whole Broth | 4% | 78 |
|  | 2% | 78 |
|  | 1% | 60 |
|  | 0.50% | 40 |
|  | 0.25% | 30 |
| 5% GENAPOL ® LRO | 4% | 66 |
|  | 2% | 74 |
|  | 1% | 60 |
|  | 0.50% | 50 |
|  | 0.25% | 10 |
| 95% *B. subtilis* QST713 Whole Broth + 5% GENAPOL ® LRO | 4% | 84 |
|  | 2% | 88 |
|  | 1% | 78 |
|  | 0.50% | 58 |
|  | 0.25% | 60 |

Example 32. Effect of Equilibration on Mixtures of Adjuvant and SERENADE® ASO

The objective of this experiment was to test the effect of equilibration for 24 hours on the mixtures of adjuvant and SERENADE® ASO (*Bacillus subtilis* QST713 fermentation product) and to better understand the interaction of the components in the mixture over time. 95% SERENADE® ASO (*Bacillus subtilis* QST713 fermentation product) was mixed with 5% GENAPOL® LRO (sodium $C_{12}/C_{14}$-fatty alcohol diglycol ether sulfate) using a homogenizer. The mixture was diluted in DI water and applied to plants as soon as possible afterwards ("T=0" treatment) or allowed to equilibrate for 24 hours prior to dilution in DI water and application to plants ("T=24" treatment). A third treatment was prepared by adding 95% SERENADE® ASO (*Bacillus subtilis* QST713 fermentation product) and 5% GENAPOL® LRO (sodium $C_{12}/C_{14}$-fatty alcohol diglycol ether sulfate) separately to DI water and applying the mixture immediately thereafter to plants ("Tank Mix" treatment). The preparation of the third treatment is similar to that of tank mixes of adjuvants and antifungal agents commonly used by growers.

Control treatments with 95% SERENADE® ASO (*Bacillus subtilis* QST713 fermentation product) alone and 5% GENAPOL® LRO (sodium $C_{12}/C_{14}$-fatty alcohol diglycol ether sulfate) alone were included for purposes of comparison. Each treatment was diluted in DI water to the concentrations shown in Table 42. The treatments were applied to plants and allowed to dry. The next day, the plants were inoculated with a suspension of *Botrytis cinerea*. After disease was evident in the untreated controls the plants were evaluated for efficacy of disease control. Each efficacy value represents the average of three measurements. 0% means an efficacy which corresponds to that of the untreated control, while an efficacy of 100% means that no disease is observed.

The results are presented in Table 42. The T=24 treatment demonstrated the highest level of efficacy at each of the application rates tested. There was a clear benefit from mixing the concentrated SERENADE® ASO (*Bacillus subtilis* QST713 fermentation product) and GENAPOL® LRO (sodium $C_{12}/C_{14}$-fatty alcohol diglycol ether sulfate) together and equilibrating for 24 hours before dilution in DI water and application to plants as compared to mixing, diluting, and applying to plants immediately. Without wishing to be bound to any theory, the equilibration time may allow for effective solubilization of the lipopeptides to produce a more active antifungal mixture.

TABLE 42

Effect of equilibration on mixtures of adjuvant and SERENADE ® ASO on the in vivo control of *Botrytis cinerea*

| Treatment | Rate (% v/v) | Efficacy in % |
|---|---|---|
| Untreated Control | — | 0 |
| 95% SERENADE ® ASO | 8% | 63 |
| (*Bacillus subtilis* QST713 fermentation product) | 4% | 7 |
| | 2% | 0 |
| | 1% | 0 |
| | 0.50% | 0 |
| 5% GENAPOL ® LRO | 8% | 50 |
| (sodium $C_{12}/C_{14}$-fatty alcohol diglycol ether sulfate) | 4% | 30 |
| | 2% | 0 |
| | 1% | 0 |
| | 0.50% | 0 |
| 95% *B. subtilis* QST713 Whole Broth + | 8% | 78 |
| 5% GENAPOL ® LRO | 4% | 60 |
| T = 0 | 2% | 53 |
| | 1% | 13 |
| | 0.50% | 0 |
| 95% *B. subtilis* QST713 Whole Broth + | 8% | 90 |
| 5% GENAPOL ® LRO | 4% | 77 |
| T = 24 | 2% | 57 |
| | 1% | 30 |
| | 0.50% | 27 |
| 95% *B. subtilis* QST713 Whole Broth + | 8% | 77 |
| 5% GENAPOL ® LRO | 4% | 50 |
| Tank Mix | 2% | 17 |
| | 1% | 10 |
| | 0.50% | 0 |

Example 33. In Vivo Preventive Test of *Bacillus* Products on *Botrytis* (Pepper)

Several commercially available *Bacillus* products formulated as wettable powders (WP) were mixed with GENAPOL® LRO (sodium $C_{12}/C_{14}$-fatty alcohol diglycol ether sulfate). The *Bacillus* products included SERENADE® MAX (*Bacillus subtilis* QST713), DOUBLE NICKEL55™ (*Bacillus amyloliquefaciens* strain D747), SUBTILEX® (*Bacillus subtilis* MBI600), and TAEGRO® (*Bacillus subtilis* var. *amyloliquefaciens* FZB24).

The treatments were prepared by mixing 20% *Bacillus* product (WP) with 5% GENAPOL® LRO (sodium $C_{12}/C_{14}$-fatty alcohol diglycol ether sulfate) and diluting the mixture in DI water. Control treatments included 20% *Bacillus* product (WP) without GENAPOL® LRO (sodium $C_{12}/C_{14}$-fatty alcohol diglycol ether sulfate) in DI water and 5% GENAPOL® LRO (sodium $C_{12}/C_{14}$-fatty alcohol diglycol ether sulfate) in DI water.

Each treatment was further diluted in DI water to the concentrations shown in Table 43. The concentrations indicated in the table represent dilution of the 5% GENAPOL® LRO, 20% *Bacillus* product (WP), or 20% *Bacillus* product (WP)+5% GENAPOL® LRO to the percentages (v/v) shown. The treatments were applied to pepper plants and allowed to dry. The next day, the pepper plants were inoculated with a suspension of *Botrytis cinerea*. After disease was evident in the untreated controls the plants were evaluated for efficacy of disease control. Each efficacy value represents the average of three measurements. 0% means an efficacy which corresponds to that of the untreated control, while an efficacy of 100% means that no disease is observed.

The experimental data presented in Table 43 represent the average values of three measurements. These results clearly show that the observed activity of each *Bacillus* product mixed with GENAPOL® LRO (sodium $C_{12}/C_{14}$-fatty alcohol diglycol ether sulfate) is greater than the calculated activity, i.e., a synergistic effect is present.

TABLE 43

In vivo Preventive Test on *Botrytis* (Pepper)

| Active Compounds | Application Rate of Compound | Efficacy in % | |
|---|---|---|---|
| | | Found* | Calc.** |
| GENAPOL ® LRO | 4% | 69 | |
| | 2% | 24 | |
| | 1% | 10 | |
| SERENADE ® MAX | 2% | 31 | |
| | 1% | 7 | |
| DOUBLE NICKEL55 ™ | 4% | 4 | |
| | 2% | 14 | |
| SUBTILEX ® | 2% | 14 | |
| | 1% | 7 | |
| TAEGRO ® | 1% | 17 | |
| SERENADE ® MAX + | 2% + 2% | 79 | 48 |
| GENAPOL ® LRO | 1% + 1% | 45 | 16 |
| DOUBLE NICKEL55 ™ + | 4% + 4% | 79 | 70 |
| GENAPOL ® LRO | 2% + 2% | 59 | 35 |
| SUBTILEX ® + | 2% + 2% | 48 | 35 |
| GENAPOL ® LRO | 1% + 1% | 48 | 16 |
| TAEGRO ® + | 1% + 1% | 38 | 26 |
| GENAPOL ® LRO | | | |

*found = activity found
**calc. = activity calculated using Colby's formula

Unless defined otherwise, all technical and scientific terms herein have the same meaning as commonly understood by one of ordinary skill in the art to which this invention belongs. All publications, patents, and patent publications cited are incorporated by reference herein in their entirety for all purposes.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:
1. A fungicidal composition comprising:
a) a lipopeptide-producing strain of *Bacillus subtilis* or *Bacillus amyloliquefaciens* selected from the group consisting of *Bacillus subtilis* QST713, *Bacillus amyloliquefaciens* strain D747, *Bacillus subtilis* MBI600, and *Bacillus subtilis* var. *amyloliquefaciens* FZB24; and
b) a compound of formula (I):

$$H_3C \left( \phantom{x} \right)_m Z^1 \left( \phantom{x} \right)_n R^1 \quad (I)$$

wherein m is an integer between 1 and 20;

n is an integer between 1 and 5;

$Z^1$ is O; and $R^1$ is a sulfate;

or a geometrical isomer, optical isomer, enantiomer, diastereoisomer, tautomer, or an agriculturally acceptable salt thereof;

in a synergistically effective amount.

2. The fungicidal composition of claim 1, wherein m is an integer between 8 and 16.

3. The fungicidal composition of claim 2, wherein the compound is 3,6-dioxaoctadecylsulfate with the formula:

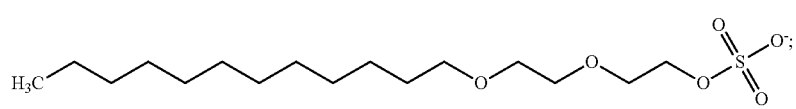

or an agriculturally acceptable salt thereof.

4. The fungicidal composition of claim 2, wherein the compound is 3,6-dioxaeicosylsulfate with the formula:

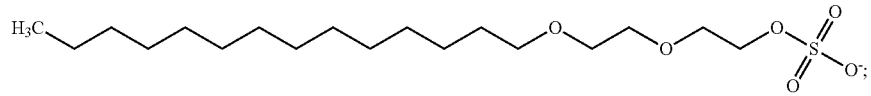

or an agriculturally acceptable salt thereof.

5. The fungicidal composition of claim 1, wherein a weight to weight ratio of the lipopeptide-producing strain of *Bacillus subtilis* or *Bacillus amyloliquefaciens* and the compound of formula (I) is about 500:1 to about 1:500.

6. The fungicidal composition of claim 5, wherein the weight to weight ratio of the lipopeptide-producing strain of *Bacillus subtilis* or *Bacillus amyloliquefaciens* and the compound of formula (I) is about 100:1 to about 1:100.

7. The fungicidal composition of claim 6, wherein the weight to weight ratio of the lipopeptide-producing strain of *Bacillus subtilis* or *Bacillus amyloliquefaciens* and the compound of formula (I) is about 25:1 to about 1:25.

8. The fungicidal composition of claim 1, wherein the strain of *Bacillus subtilis* or *Bacillus amyloliquefaciens* is part of a fermentation product.

9. The fungicidal composition of claim 8, wherein a concentration of lipopeptides in the fermentation product is at least 1 mg/g.

10. The fungicidal composition of claim 1, wherein the lipopeptide from the lipopeptide-producing strain of *Bacillus subtilis* or *Bacillus amyloliquefaciens* is an iturin-type compound, a surfactin-type compound, a fengycin-type compound, or a combination thereof.

11. The fungicidal composition of claim 10, wherein the lipopeptide is the iturin-type compound.

12. The fungicidal composition of claim 11, wherein the iturin-type compound is bacillomycin D, bacillomycin F, bacillomycin L, bacillomycin LC (bacillopeptin), mycosubtilin, iturin A, iturin $A_L$, or iturin C.

13. The fungicidal composition of claim 10, wherein the lipopeptide is a fengycin-type compound.

14. The fungicidal composition of claim 13, wherein the fengycin-type compound is fengycin A, fengycin B, plipastatin A, plipastatin B, or an agrastatin.

15. The fungicidal composition of claim 10, wherein the lipopeptide is a surfactin-type compound.

16. The fungicidal composition of claim 15, wherein the surfactin-type compound is esperin, lichenysin, pumilacidin, or surfactin.

17. The fungicidal composition of claim 1, wherein the fungicidal composition is formulated as a suspension concentrate (SC), an oil dispersion (OD), or water-dispersible granules (WG).

18. A plant or plant part coated with the fungicidal composition according to claim 1.

19. A seed treated with the fungicidal composition according to claim 1.

20. A method of controlling fungal harmful organisms and/or bacterial harmful organisms in a plant, the method comprising applying an effective amount of the fungicidal composition of claim 1 to the plant, to a part of the plant and/or to a locus on which the plant or plant part grows or is to be planted.

21. The method of claim 20, wherein the fungal harmful organisms are *Phytophthora infestans* and/or *Botrytis cinerea* and/or *Plasmopara viticola* and/or *Sphaerotheca fuliginea* and/or *Venturia inaequalis* and/or *Alternaria solani* and/or *Uromyces appendiculatus* and/or *Phakopsora pachyrhizi*.

22. The method of claim 20, wherein the bacterial harmful organisms are *Acidovorax avenae*, *Burkholderia glumae* and/or *Xanthomonas campestris* pv. *oryzae* in rice, *Candidatus Liberibacter* spec and/or *Xanthomonas axonopodis* pv. *citri* and/or *Xanthomonas campestris* pv. *vesicatoria* and/or *Xylella fastidiosa* in citrus, *Pseudomonas syringae* pv. *actinidae* in Kiwi, *Xanthomonas campestris* and/or *Xanthomonas campestris* pv. *pruni* in peaches, *Pseudomonas syringae* pv. *glycinea* and/or *Xanthomonas axonopodis* pv. *glycines* in soybeans, *Burkholderia* spec and/or *Xanthomonas transluscens* in cereals, *Pseudomonas syringae*, *Pseudomonas syringae* pv. *tomato* and/or *Xanthomonas campestris* in tomatoes, *Pseudomonas syringae* and/or *Pseudomonas syringae* pv. *lachrymans* in cucumbers, *Erwinia atroseptica*, *Erwinia carotovora* and/or *Streptomyces scabies* in potatoes.

23. The method of claim 20, wherein the plant is apples, bananas, citrus, kiwi, melons, peaches, pears, pineapple, pome fruit, pomegranate, cabbage, cauliflower, cucumbers, cucurbits, tomatoes, potatoes, wheat, rice or soybeans.

24. The method of claim 20, wherein the fungicidal composition is applied as a foliar treatment.

25. The method of claim 20, wherein the fungicidal composition is applied as a soil treatment.

26. The method of claim 20, wherein the fungicidal composition is applied as a suspension concentrate (SC), an oil dispersion (OD), or water-dispersible granules (WG).

27. A method for treating powdery mildew, rust, leaf blotch diseases, leaf wilt diseases, root and stem diseases, ear and panicle diseases, smut fungi diseases, fruit rot, seed and soilborne decay, mould, wilt, rot and damping-off diseases, cancers galls and witches' broom, wilt diseases, leaf blister or leaf curl diseases in a plant, the method comprising applying to the plant or to a plant part the fungicidal composition of claim 1.

* * * * *